US010815200B2

(12) United States Patent
Cardinale et al.

(10) Patent No.: US 10,815,200 B2
(45) Date of Patent: Oct. 27, 2020

(54) 18F—TAGGED INHIBITORS OF PROSTATE SPECIFIC MEMBRANE ANTIGEN (PSMA) AND THEIR USE AS IMAGING AGENTS FOR PROSTATE CANCER

(71) Applicants: DEUTSCHES KREBSFORSCHUNGSZENTRUM, Heidelberg (DE); RUPRECHT-KARLS-UNIVERSITAET HEIDELBERG, Heidelberg (DE)

(72) Inventors: Jens Cardinale, Vienna (AT); Martin Schaefer, Neckarsteinach (DE); Klaus Kopka, Dossenheim (DE); Matthias Eder, Freiburg (DE); Ulrike Bauder-Wuest, Schriesheim (DE); Michael Eisenhut, Heidelberg (DE); Martina Benesova, Neckarsteinach (DE); Uwe Haberkorn, Schwetzingen (DE); Frederik L. Giesel, Heidelberg (DE)

(73) Assignees: DEUTSCHES KREBSFORSCHUNGSZENTRUM, Heidelberg (DE); RUPRECHT-KARLS-UNIVERSITAET HEIDELBERG, Heidelberg (DE)

(*) Notice: Subject to any disclaimer, the term of this patent is extended or adjusted under 35 U.S.C. 154(b) by 0 days.

(21) Appl. No.: 15/915,978

(22) Filed: Mar. 8, 2018

(65) Prior Publication Data
US 2018/0194729 A1 Jul. 12, 2018

Related U.S. Application Data

(63) Continuation of application No. PCT/EP2016/001573, filed on Sep. 19, 2016.

(30) Foreign Application Priority Data

Sep. 30, 2015 (EP) .................................... 15002800
Apr. 6, 2016 (EP) .................................... 16164090
Aug. 4, 2016 (EP) .................................... 16182764

(51) Int. Cl.
A61K 38/00 (2006.01)
C07D 213/61 (2006.01)
A61K 51/04 (2006.01)
C07B 59/00 (2006.01)
G01N 33/574 (2006.01)
C07K 7/02 (2006.01)
A61P 35/00 (2006.01)

(52) U.S. Cl.
CPC ............. *C07D 213/61* (2013.01); *A61K 51/04* (2013.01); *A61K 51/0455* (2013.01); *A61P 35/00* (2018.01); *C07B 59/002* (2013.01); *C07K 7/02* (2013.01); *G01N 33/57434* (2013.01); *A61K 38/00* (2013.01); *C07B 2200/05* (2013.01)

(58) Field of Classification Search
CPC ........ A61K 38/00; A61K 51/00; A61K 51/04; A61K 51/0455; A61K 2123/00; C07D 213/61; A61P 35/00; G01N 33/57434; C07B 59/002; C07B 2200/05; C07K 7/02
USPC .......... 424/1.11, 1.65, 1.69, 1.81, 1.85, 1.89, 424/9.1, 9.2, 9.3; 530/300; 514/1.1
See application file for complete search history.

(56) References Cited

U.S. PATENT DOCUMENTS 10,016,519 B2 * 7/2018 Kopka ................... A61K 51/06
2015/0110715 A1 4/2015 Eder et al.

FOREIGN PATENT DOCUMENTS

| EP | 1177200 B1 | 6/2005 |
| EP | 1472541 B1 | 9/2009 |
| EP | 2136788 B1 | 10/2011 |
| EP | 2170075 B1 | 3/2014 |
| EP | 2759535 A1 | 7/2014 |
| EP | 2823826 A2 | 1/2015 |
| EP | 2097111 B1 | 7/2015 |
| EP | 2921482 A2 | 9/2015 |
| EP | 2117604 B1 | 7/2017 |
| EP | 2942065 B1 | 6/2018 |
| EP | 3335736 A1 | 6/2018 |
| WO | 03000201 A2 | 1/2003 |
| WO | 2006093991 A1 | 9/2006 |
| WO | 2008057437 A2 | 5/2008 |
| WO | 2009026177 A1 | 2/2009 |
| WO | 2009070302 A1 | 6/2009 |
| WO | 2010014933 A2 | 2/2010 |
| WO | 2010065899 A2 | 6/2010 |
| WO | 2010065902 A2 | 6/2010 |
| WO | 2010108125 A2 | 9/2010 |
| WO | 2010114723 A1 | 10/2010 |
| WO | 2012072728 A1 | 6/2012 |
| WO | 2012078534 A1 | 6/2012 |
| WO | 2012166923 A2 | 12/2012 |
| WO | 2013022797 A1 | 2/2013 |
| WO | 2013028664 A1 | 2/2013 |
| WO | 2014106208 A1 | 7/2014 |
| WO | 2014127365 A1 | 8/2014 |

(Continued)

OTHER PUBLICATIONS

International Search Report dated Jan. 5, 2017 in International Application No. PCT/EP2016/001573.

*Primary Examiner* — D. L. Jones
(74) *Attorney, Agent, or Firm* — Perkins Coie LLP; Viola Kung

(57) ABSTRACT

The present invention generally relates to the field of radio-pharmaceuticals and their use in nuclear medicine as tracers and imaging agents for various disease states of prostate cancer.

8 Claims, 21 Drawing Sheets

(56) References Cited

FOREIGN PATENT DOCUMENTS

| WO | 2015004029 A1 | 1/2015 |
| WO | 2015/055318 A1 | 4/2015 |
| WO | 2015057250 A1 | 4/2015 |
| WO | 2015073678 A1 | 5/2015 |
| WO | 2015143029 A1 | 9/2015 |
| WO | 2015171792 A1 | 11/2015 |
| WO | 2016030329 A1 | 3/2016 |
| WO | 2016040179 A1 | 3/2016 |
| WO | 2016062370 A1 | 4/2016 |
| WO | 2016065142 A2 | 4/2016 |
| WO | 2016065145 A2 | 4/2016 |

* cited by examiner

[$^{18}$F]Fluoroalkynes for "click-chemistry" to triazoles

Marik and Sutcliffe Tetrahedron Lett., 2006, 47, 6681.

[$^{18}$F]Fluorobenzaldehydes for oxime formation

Poethko et al. J. Nucl. Med., 2004, 45, 892.

Schirrmacher et al. Angew. Chem. Int. Ed., 2006, 45, 6047.

Stochiometric leverage of molar activity in n.c.a. formation of [¹⁸F]aryltrifluoroboronates

Two step synthesis of azido-rhodamine-[¹⁸F]trifluoroboronate

Molar activity [Ci/µmol]

|  | ¹⁸F⁻ (BOS) | [¹⁸F]product |
| --- | --- | --- |
| n.c.a. | 6.5 | 15 ± 0.5 |
| c.a. | 2.7 | 7.7 ± 0.3 |

Z. Lin et al., Angew. Chem. 125, 2359 - 2362 (2013)

Self-immolating fluorescent fluoride sensor assay

S. Y. Kim and J. I. Hong, 9, 3109-3112 (2007)

O. Jakobson et al., *Bioconjugate Chem.*, 2011, 22, 422-428.

PSMA-1009 or [18F]DCFPyL
( Y. Chen et al., Clin. Cancer
Res. 2011, 17, 7645-7653)

1 h p.i.        3 h p.i.

1 h p.i.    3 h p.i.

18F—TAGGED INHIBITORS OF PROSTATE SPECIFIC MEMBRANE ANTIGEN (PSMA) AND THEIR USE AS IMAGING AGENTS FOR PROSTATE CANCER

This application is a continuation of PCT/EP2016/001573, filed Sep. 19, 2016, which claims priority of EP 15002800.9, filed Sep. 30, 2015, EP 16164090.9, filed Apr. 6, 2016, and EP16182764.7, filed Aug. 4, 2016. The contents of the above-identified applications are incorporated herein by reference in their entirety.

The present invention generally relates to the field of radiopharmaceuticals and their use in nuclear medicine as tracers and imaging agents and for the various disease states of prostate cancer.

BACKGROUND OF THE INVENTION

Prostate cancer (PCa) is the leading cancer in the US and European population. At least 1-2 million men in the western hemisphere suffer from prostate cancer and it is estimated that the disease will strike one in six men between the ages of 55 and 85. There are more than 300.000 new cases of prostate cancer diagnosed each year in USA. The mortality from the disease is second only to lung cancer. Currently anatomic methods, such as computed tomography (CT), magnetic resonance (MR) imaging and ultrasound, predominate for clinical imaging of prostate cancer. An estimated $2 billion is currently spent worldwide on surgical, radiation, drug therapy and minimally invasive treatments. However, there is presently no effective therapy for relapsing, metastatic, androgen-independent prostate cancer.

A variety of experimental low molecular weight PCa imaging agents are currently being pursued clinically, including radiolabeled choline analogs ([$^{11}$C]Choline, [$^{18}$F] FECh, [$^{18}$F] FMC, [$^{18}$F]fluorodihydrotestosterone ([$^{18}$F] FDHT), anti-1-amino-3-[$^{18}$F]fluorocyclobutyl-1-carboxylic acid (anti[$^{18}$F]F-FACBC, [$^{11}$C]acetate and 1-(2-deoxy-2-[$^{18}$F]fluoro-L-arabinofuranosyl)-5-methyluracil (-[$^{18}$F] FMAU) (Scher, B.; et al. *Eur J Nucl Med Mol Imaging* 2007, 34, 45-53; Rinnab, L.; et al. *BJU Int* 2007, 100, 786,793; Reske, S. N.; et al. *J Nucl Med* 2006, 47, 1249-1254; Zophel, K.; Kotzerke, *J. Eur J Nucl Med Mol Imaging* 2004, 31, 756-759; Vees, H.; et al. *BJU Int* 2007, 99, 1415-1420; Larson, S. M.; et al. *J Nucl Med* 2004, 45, 366-373; Schuster, D. M.; et al. *J Nucl Med* 2007, 48, 56-63; Tehrani, O. S.; et al. *J Nucl Med* 2007, 48, 1436-1441). Each operates by a different mechanism and has certain advantages, e.g., low urinary excretion for [$^{11}$C]choline, and disadvantages, such as the short physical half-life of positron-emitting radionuclides.

It is well known that tumors may express unique proteins associated with their malignant phenotype or may over-express normal constituent proteins in greater number than normal cells. The expression of distinct proteins on the surface of tumor cells offers the opportunity to diagnose and characterize disease by probing the phenotypic identity and biochemical composition and activity of the tumor. Radioactive molecules that selectively bind to specific tumor cell surface proteins provide an attractive route for imaging and treating tumors under non-invasive conditions. A promising new series of low molecular weight imaging agents targets the prostate-specific membrane antigen (PSMA) (Mease R. C. et al. *Clin Cancer Res.* 2008, 14, 3036-3043; Foss, C. A.; et al. *Clin Cancer Res* 2005, 11, 4022-4028; Pomper, M. G.; et al. *Mol Imaging* 2002, 1, 96-101; Zhou, J.; etr al. *Nat Rev Drug Discov* 2005, 4, 1015-1026; WO 2013/022797).

PSMA is a trans-membrane, 750 amino acid type II glycoprotein that has abundant and restricted expression on the surface of PCa, particularly in androgen-independent, advanced and metastatic disease (Schulke, N.; et al. *Proc Natl Acad Sci USA* 2003, 100, 12590-12595). The latter is important since almost all PCa become androgen independent over the time. PSMA possesses the criteria of a promising target for therapy, i.e., abundant and restricted (to prostate) expression at all stages of the disease, presentation at the cell surface but not shed into the circulation and association with enzymatic or signaling activity (Schulke, N.; et al. *Proc. Natl. Acad. Sci. USA* 2003, 100, 12590-12595). The PSMA gene is located on the short arm of chromosome 11 and functions both as a folate hydrolase and neuropeptidase. It has neuropeptidase function that is equivalent to glutamate carboxypeptidase II (GCPII), which is referred to as the "brain PSMA", and may modulate glutamatergic transmission by cleaving N-acetylaspartylglutamate (NAAG) to N-acetylaspartate (NAA) and glutamate (Nan, F.; et al. *J Med Chem* 2000, 43, 772-774). There are up to $10^6$ PSMA molecules per cancer cell, further suggesting it as an ideal target for imaging and therapy with radionuclide-based techniques (Tasch, J.; et al. *Crit Rev Immunol* 2001, 21, 249-261).

The radio-immunoconjugate of the anti-PSMA monoclonal antibody (mAb) 7E11, known as the PROSTASCINT® scan, is currently being used to diagnose prostate cancer metastasis and recurrence. However, this agent tends to produce images that are challenging to interpret (Lange, P. H. PROSTASCINT scan for staging prostate cancer. *Urology* 2001, 57, 402-406; Haseman, M. K.; et al. *Cancer Biother Radiopharm* 2000, 15, 131-140; Rosenthal, S. A.; et al. *Tech Urol* 2001, 7, 27-37). More recently, monoclonal antibodies have been developed that bind to the extracellular domain of PSMA and have been radiolabeled and shown to accumulate in PSMA-positive prostate tumor models in animals. However, diagnosis and tumor detection using monoclonal antibodies has been limited by the low permeability of the monoclonal antibody in solid tumors.

The selective targeting of cancer cells with radiopharmaceuticals for imaging or therapeutic purposes is challenging. A variety of radionuclides are known to be useful for radio-imaging or cancer radiotherapy, including $^{11}$C, $^{18}$F, $^{111}$In, $^{90}$Y, $^{68}$Ga, $^{177}$Lu, $^{99m}$Tc, $^{123}$I and $^{131}$I Recently it has been shown that some compounds containing a glutamate-urea-glutamate (GUG) or a glutamate-urea-lysine (GUL) recognition element linked to a radionuclide-ligand conjugate exhibit high affinity for PSMA.

Several $^{18}$F-tagged compounds which show PSMA interaction and are suitable for the detection of prostate cancer are shown in EP 14 003 570.0. These compounds, however, show high lipophilic properties which make them, to a certain extent, difficult to handle and to administer.

New agents that will enable rapid visualization of prostate cancer are needed. Thus, the object of the present invention is to develop ligands that interact with PSMA and carry appropriate radionuclides which provide a promising and novel targeting option for the detection, treatment and management of prostate cancer.

SUMMARY OF THE INVENTION

The solution of said object is achieved by providing the embodiments characterized in the claims.

The inventors found new compounds which are useful radiopharmaceuticals and their use in nuclear medicine as tracers and imaging agents and for various disease states of prostate cancer.

The novel imaging agents with structural modifications in the linker region have improved tumor targeting properties and pharmacokinetics. The pharmacophore presents three carboxylic groups able to interact with the respective side chains of PSMA and an oxygen as part of zinc complexation in the active center. Besides these obligatory interactions, the inventors were able to optimize the lipophilic interactions in the linker region in comparison to the compounds described in EP 14003570.0. Moreover, the inventors added some hydrophilic building blocks to the linker for an enhancement of the pharmakokinetics.

DETAILED DESCRIPTION OF THE INVENTION

Figure 1:
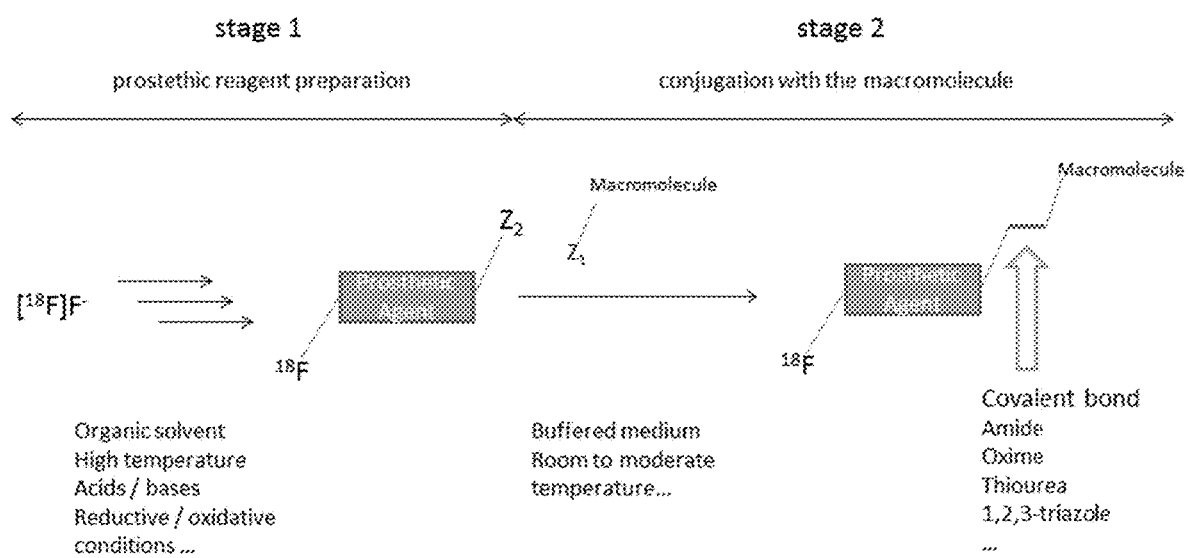
FIG. 1: $^{18}$F-Labelling of macromolecules
Figure 2:
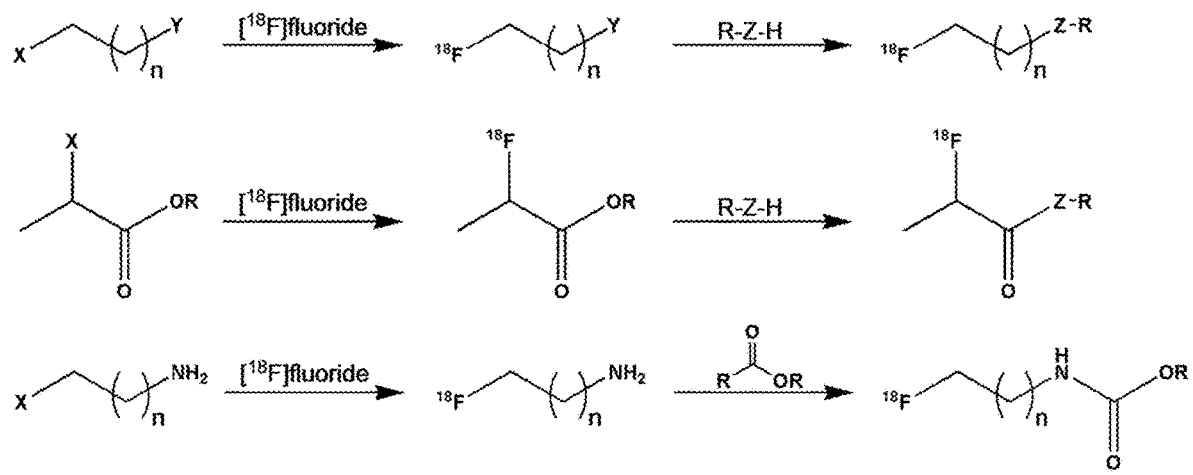
FIG. 2: $^{18}$F-Fluorination via prosthetic groups
Figure 3:
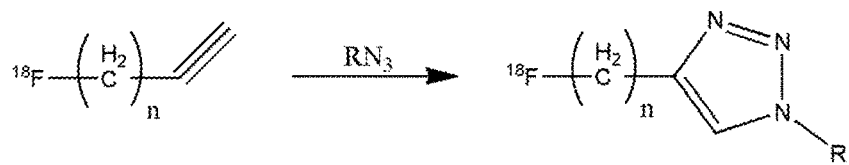
FIG. 3: $^{18}$F-prosthetic groups for peptides
Figure 3:
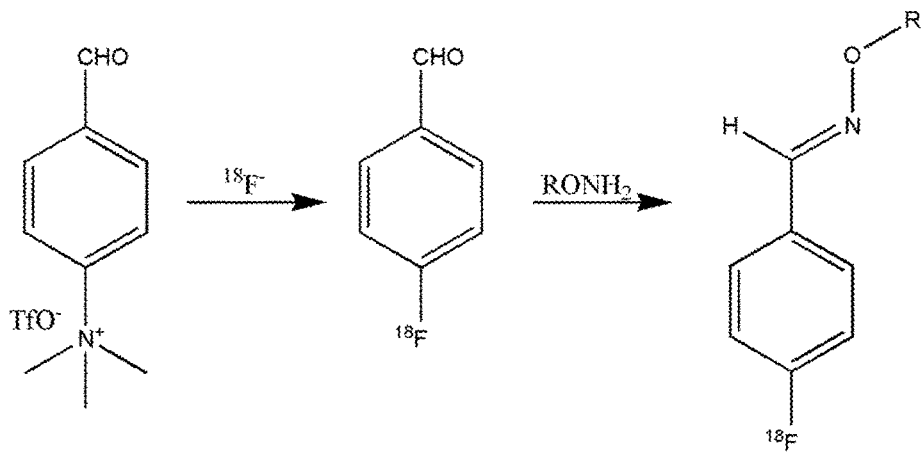
Figure 3:
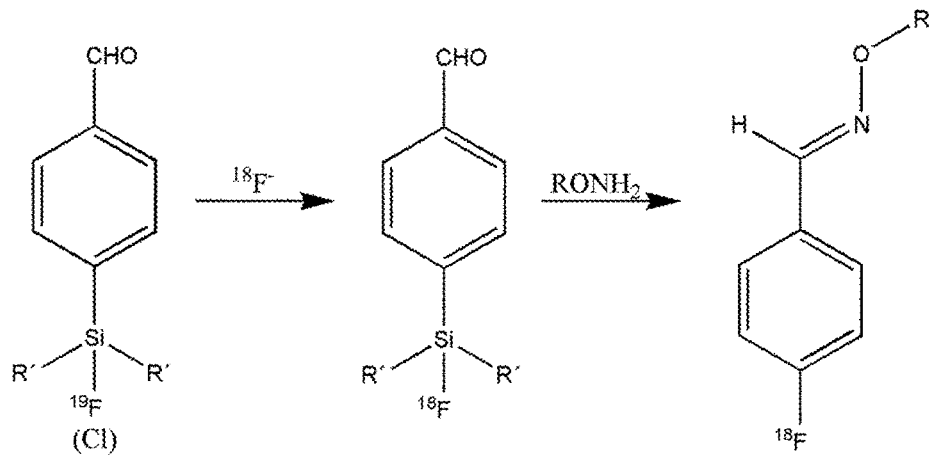
Figure 4:
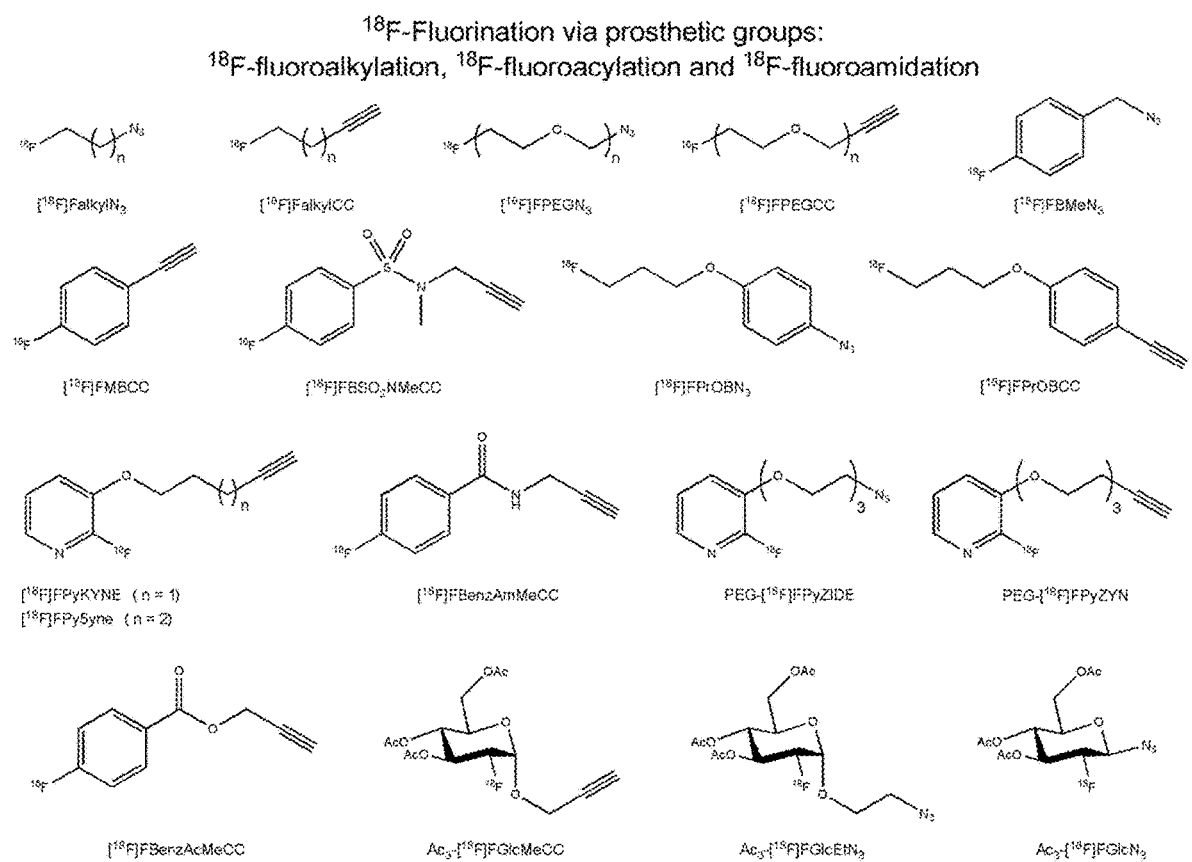
FIG. 4: $^{18}$F-Labelled Prosthetic Groups using "Click Chemistry
Figure 5:
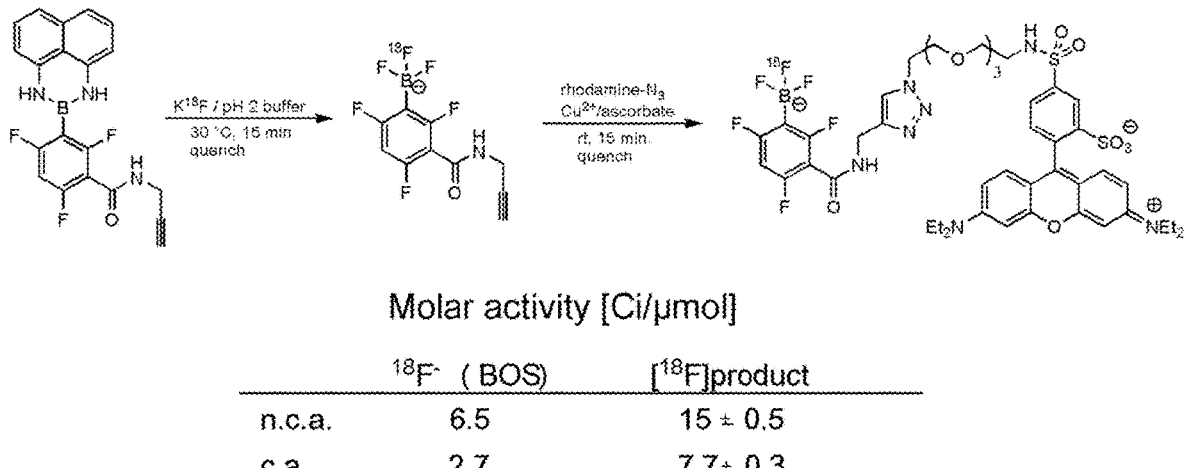
"
FIG. 5: Formation of [$^{18}$F]aryltrifluoroboronates and fluoride sensors
Figure 5:
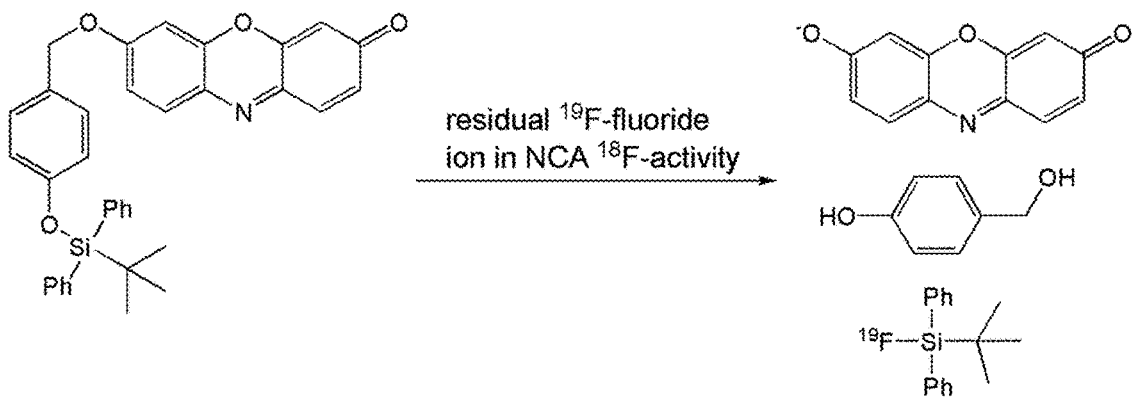
Figure 6:
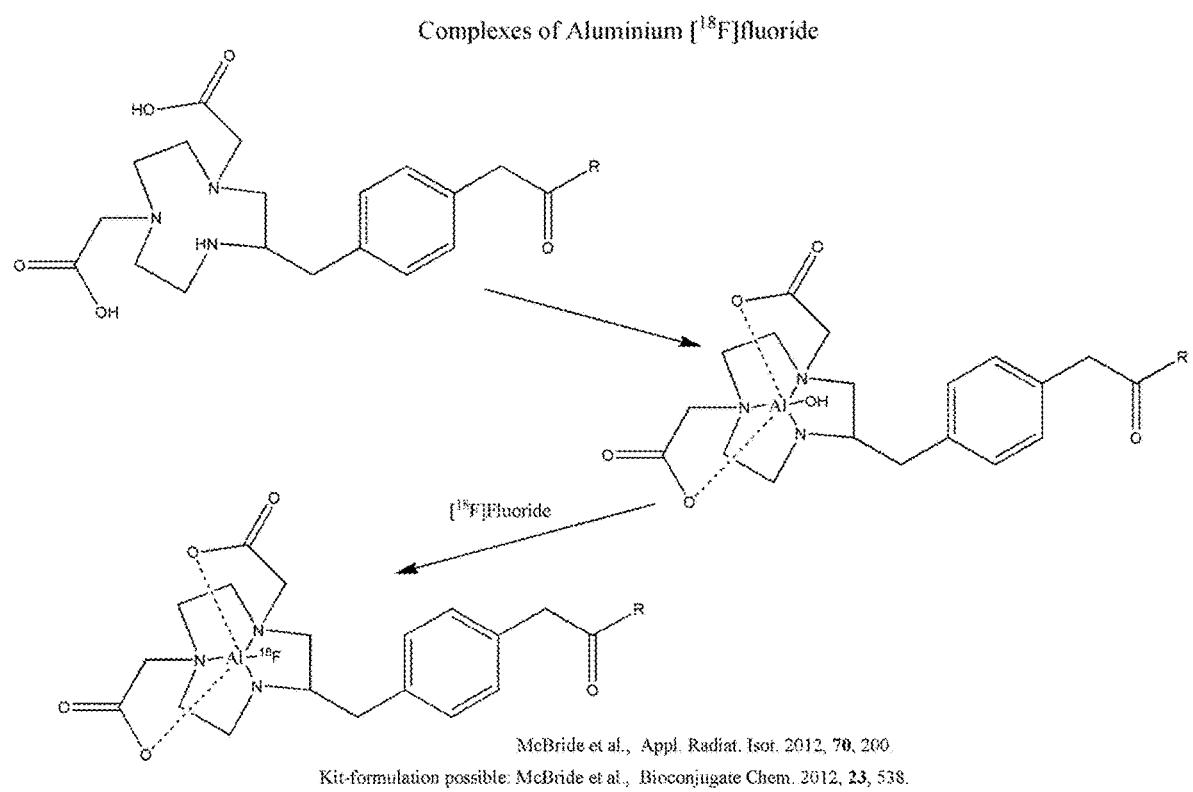
FIG. 6: Complexes of $^{18}$F-Fluorides
Figure 7:
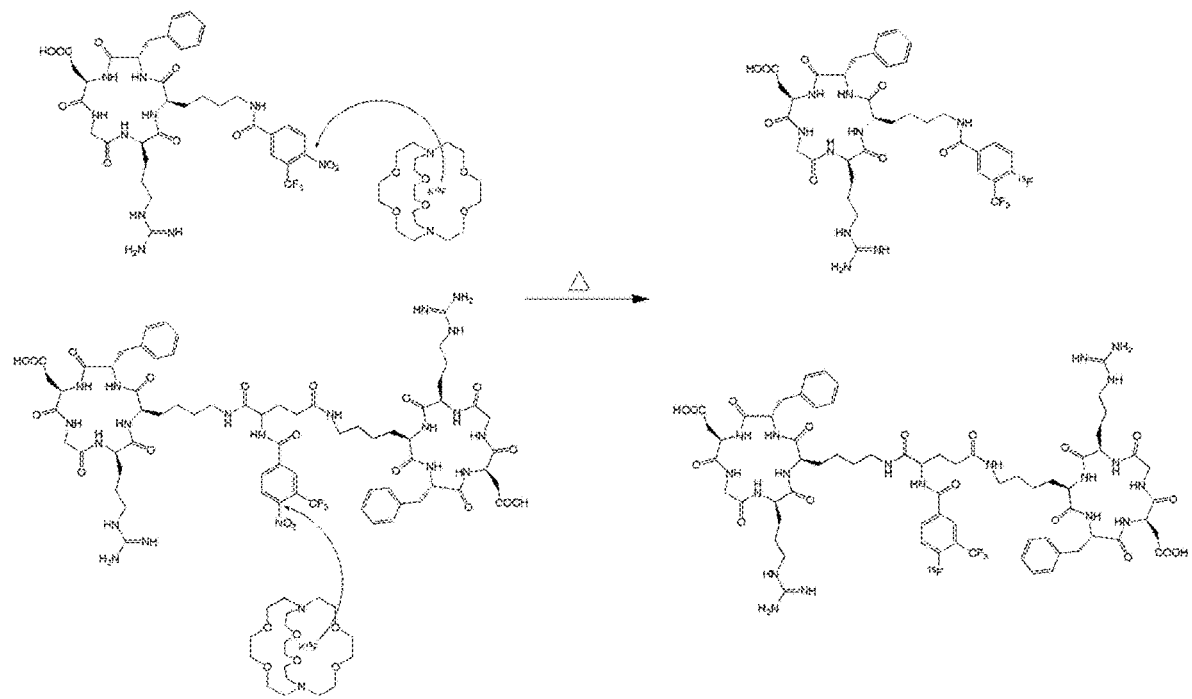
FIG. 7: $^{18}$F-Labelling of RGD peptides

The present invention relates to radiopharmaceuticals and their use in nuclear medicine as tracers and imaging agents for the various disease states of prostate cancer.

Thus, the present invention concerns compounds that are represented by the general Formula I

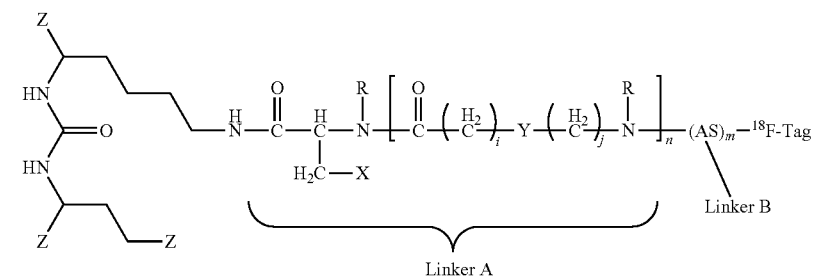

Formula I
with:

| | |
|---|---|
| i, j | 0, 1 |
| m | 1-5 |
| n | 0-3 |
| R | H, CH$_3$ |
| AS | Natural or non-natural amino acid |
| Z: | —CO$_2$H, —SO$_2$H, —SO$_3$H, —SO$_4$H, —PO$_2$H, —PO$_3$H, —PO$_4$H$_2$ |
| X: | Naphthyl, Phenyl, Biphenyl, Indolyl (=2,3-benzopyrrolyl), Benzothiazolyl, Quinoyl |
| Y: | Aryl, Alkylaryl, Cyclopentyl, Cyclohexyl, Cycloheptyl, N-Piperidyl and N-methylated Piperidyl salt |
| $^{18}$F-Tag: | |

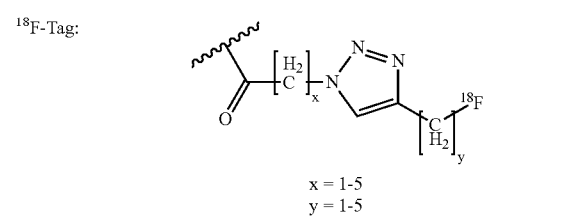

x = 1-5
y = 1-5

-continued x = 1-5
y = 1-5 x = 1-5
y = 1-5 x = 1-5
y = 1-5

-continued

With:
x = 1-5
Carboydrate:

x = 1-5
y = 1-5

-continued

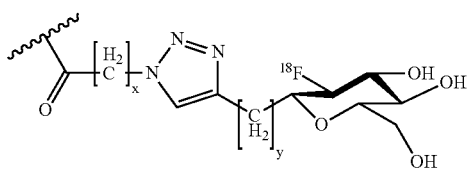

x = 1-5
y = 1-5

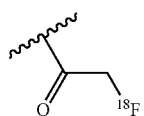

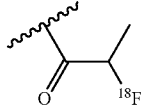 [SMILES: *C(=O)C(C)[18F]]

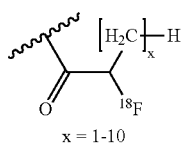

x = 1-10

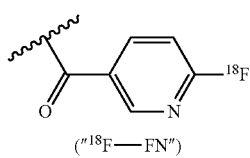

("$^{18}$F—FN")

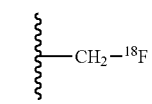

$\text{---CH}_2\text{---}^{18}\text{F}$ $\text{---CH}_2\text{---CH}_2\text{---}^{18}\text{F}$ $\text{---[CH}_2\text{]}_x\text{---}^{18}\text{F}$ x = 1-10

$\text{---[}^{18}\text{F]CF}_3$ $\text{---CH}_2\text{---[}^{18}\text{F]CF}_3$

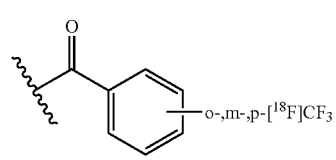

-continued

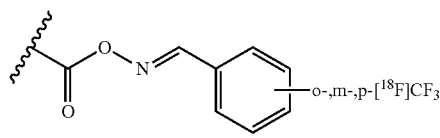

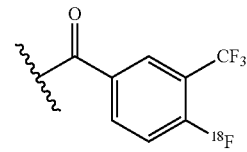 [SMILES: *C(=O)c1ccc([18F])c(C(F)(F)F)c1]

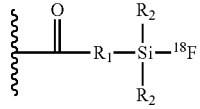

R$_1$: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R$_2$: Any alkyl or aryl group
especially methyl isopropyl, tert-butyl,
phenyl or 1-naphtyl

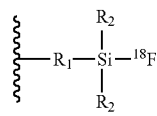

R$_1$: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R$_2$: Any alkyl or aryl group
especially methyl isopropyl, tert-butyl,
phenyl or 1-naphtyl

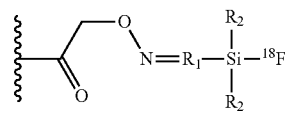

R$_1$: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R$_2$: Any alkyl or aryl group
especially methyl isopropyl, tert-butyl,
phenyl or 1-naphtyl

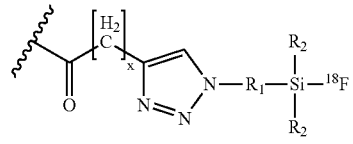

x = 1-5

R$_1$: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R$_2$: Any alkyl or aryl group
especially methyl isopropyl, tert-butyl,
phenyl or 1-naphtyl

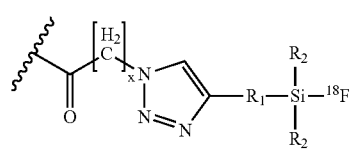

x = 1-5

R₁: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R₂: Any alkyl or aryl group
especially methyl isopropyl, tert-butyl,
phenyl or 1-naphtyl

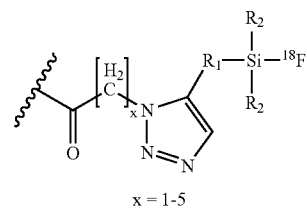

x = 1-5

R₁: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R₂: Any alkyl or aryl group
especially methyl isopropyl, tert-butyl,
phenyl or 1-naphtyl

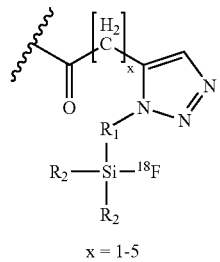

x = 1-5

R₁: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R₂: Any alkyl or aryl group
especially methyl isopropyl, tert-butyl,
phenyl or 1-naphtyl If not stated otherwise, in the present invention the term "alkyl" by itself or as part of another molecule, means a straight or branched chain, or cyclic hydrocarbon radical, or combination thereof, which may be fully saturated, mono- or polyunsaturated and can include di- and multivalent radicals, The "alkyl" residue is preferably $C_1$ to $C_{10}$ and may be unsubstituted or substituted (e.g with halogen). Preferred alkyl residues are methyl, ethyl, n-propyl, iso-propyl, n-butyl, tert-butyl, n-pentyl, n-hexyl, n-hepyl or n-octyl or the like. The same also applies to the corresponding cycloalkyl compounds having preferably 3 to 10 carbon atoms, e.g. cyploproyl, cyclobutyl, cyclopentyl, cyclohexyl, cycloheptyl, cyclooctyl, etc. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl, such as "heteroalkyl", "haloalkyl" and "homoalkyl".

The term "aryl", as used herein, refers to a closed ring structure which has at least one ring having a conjugated pi electron system and includes both carbocyclic aryl and heterocyclic aryl (or "heteroaryl" or "heteroaromatic") groups. The carbocyclic or heterocyclic aromatic group may contain from 5 to 20 ring atoms. The term includes mono-cyclic rings linked covalently or fused-ring polycyclic (i.e., rings which share adjacent pairs of carbon atoms) groups. An aromatic group can be unsubstituted or substituted. Non-limiting examples of "aromatic" or "aryl", groups include phenyl, 1-naphthyl, 2-naphthyl, 2-biphenyl, 3-biphenyl, 4-biphenyl, anthracenyl, and phenanthracenyl. Substituents for each of the above noted aryl and heteroaryl ring systems are selected from the group of acceptable substituents (e.g. alkyl, carbonyl, carboxyl or halogen) described herein. The term "aryl" when used in combination with other terms (including but not limited to, aryloxy, arylthioxy, aralkyl) includes both aryl and heteroaryl rings. Thus, the term "aralkyl" or "alkaryl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by a heteroatom, by way of example only, by an oxygen atom. Examples of such aryl groups include, but are not limited to, phenoxymethyl, 2-pyridyloxymethyl, 3-(1-naphthyloxy)propyl, and the like.

"Heteroaryl" refers to aryl groups which contain at least one heteroatom selected from N, O, and S; wherein the nitrogen and sulfur atoms may be optionally oxidized, and the nitrogen atom(s) may be optionally quaternized. Heteroaryl groups may be substituted or unsubstituted. A heteroaryl group may be attached to the remainder of the molecule through a heteroatom. Non-limiting examples of suitable groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 4-benzothiazolyl, 5-benzothiazolyl, 6-benzothiazolyl, 7-benzothiazolyl, purinyl, 2-benzimidazolyl, 4-indolyl, 5-indolyl, 6-indolyl, 7-indolyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl or 8-quinolyl.

The term "amino acid" refers to naturally occurring and non-natural amino acids, as well as amino acid analogs and amino acid mimetics that function in a manner similar to the naturally occurring amino acids. Naturally amino acids are the 20 common amino acids in their D- or L-form (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, by way of example only, an ex-carbon that is bound to a hydrogen, a carboxyl group, an amino group, and an R group. Such analogs may have modified R groups (by way of example, norleucine) or may have modified peptide backbones, while still retaining the same basic chemical structure as a naturally occurring amino acid. Non-limiting examples of amino acid analogs include homoserine, norleucine, methionine sulfoxide, methionine methyl sulfonium. Amino acids may be referred to herein by either their name, their commonly known three letter symbols or by the one-letter symbols recommended by the IUPAC-IUB Biochemical Nomenclature Commission. A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid" or "artificial amino acid. The term "non-natural amino acid" includes, but is not limited to, amino acids which occur by modification of a naturally encoded amino acid in their backbone or side chains. In some embodiments the non-natural amino acid comprises a carbonyl group, an acetyl group, an aminooxy group, a hydrazine group, a hydrazide group, a semicarbazide group, an azide group or an alkyne group. In a preferred embodiment the non-natural amino acid has the formula

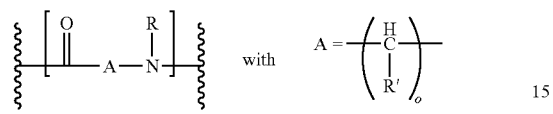

and R'=H, CO$_2$H, CH$_2$CO$_2$H, C$_2$H$_4$CO$_2$H, CH(CO$_2$H)$_2$, CH(CH$_2$CO$_2$H)$_2$, CH(CO$_2$H)(CH$_2$CO$_2$H), CH$_2$CH(CO$_2$H)$_2$, SO$_3$H; o=1-3; R=H, CH$_3$ Preferred are those amino acids which bring a hydrophilic element into the compound of Formula I.

Some of the residues herein (including, but not limited to non-natural amino acids), may exist in several tautomeric forms. All such tautomeric forms are considered as part of the compounds described herein. Also, for example all enol-keto forms of any compounds herein are considered as part of the compositions described herein.

The linker B, i.e. the natural amino acids and/or non-naturally occurring amino acids, may be bound within the molecule via a peptide or amide linkage. In case of acidic amino acids (e.g. glutamic acid, aspartic acid) however, the binding may be alternatively via the α-, β or γ-position.

Although it is preferred that the Z-Group is —CO$_2$H it may be easily replaced with biosteric replacements such as —SO$_2$H, —SO$_3$H, —SO$_4$H, —PO$_2$H, —PO$_3$H, —PO$_4$H$_2$, see e.g. "The Practice of Medicinal Chemistry" (Academic Press New York, 1996), page 203.

Within the meaning of the invention, all residues are considered combinable unless stated otherwise in the definition of the residues. All conceivable subgroupings thereof are considered to be disclosed.

The $^{18}$F-Tags of the above Table comprising triazoles exist in two isomeric forms which belong both to the invention and are illustrated by the given formulas.

Figure 22:
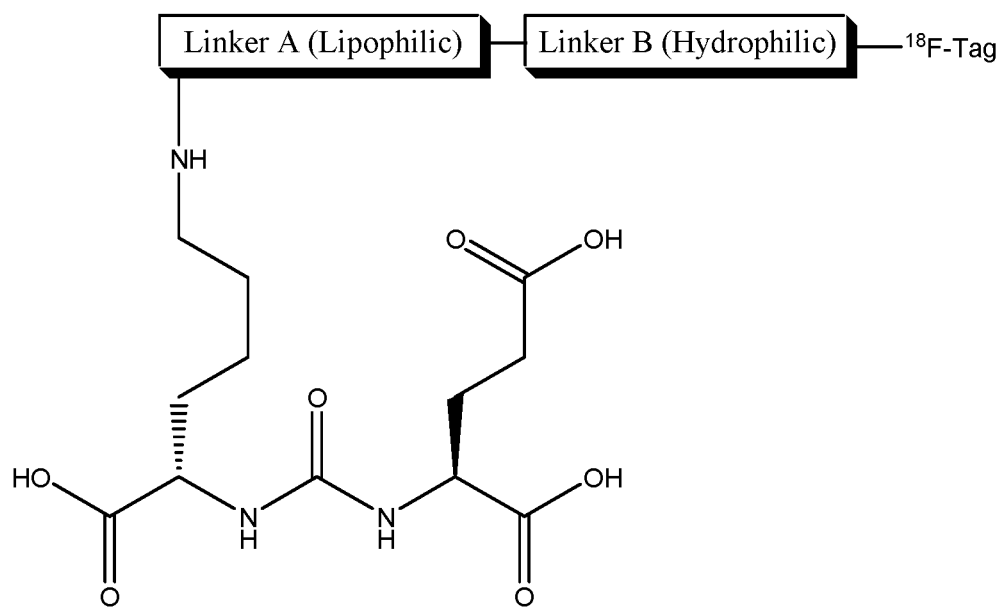
FIG. 22: Structure of preferred compounds of the present invention.

Thus, preferred molecules of the present invention consist of three principle components (as shown in FIG. 22): the hydrophilic PSMA binding motif (Glu-Urea-Lys=Glu-NH—CO—NH-Lys), two variable linkers (Linker A and Linker B) and the $^{18}$F-Tag.

Some preferred lipophilic linkers (linker A) are shown below, wherein R$^1$=Glu-urea-Lys (PSMA binding motif) and R$^2$=(Linker B)$_m$-[$^{18}$F-Tag] with m=1-5,

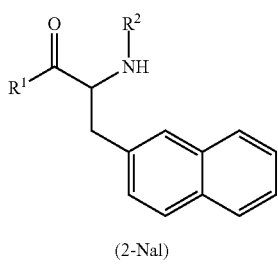

(2-Nal)

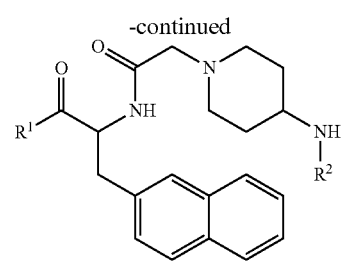

(2-Nal)-(AcAP)

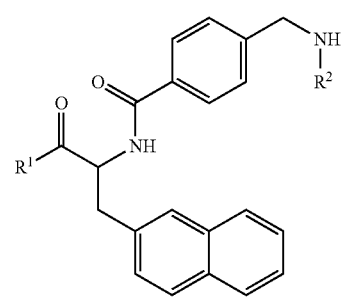

(2-Nal)-(Bn)

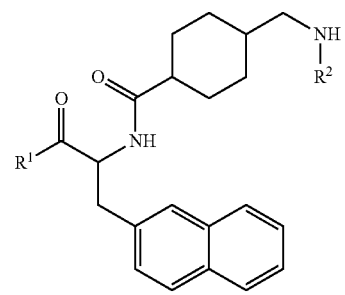

(2-Nal)-(Chx)

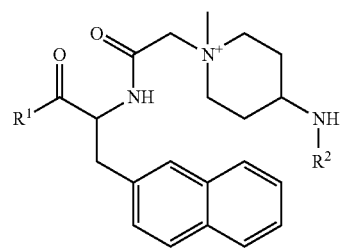

(2-Nal)-(AcAMP)

(In form of any pharmaceutically acceptable salt)

The different preferred building blocks for hydrophilic linkers (linker B) are shown below with their preferred connectivity exemplified on the basis of the respective single amino acids (m=1 in the generic structure)

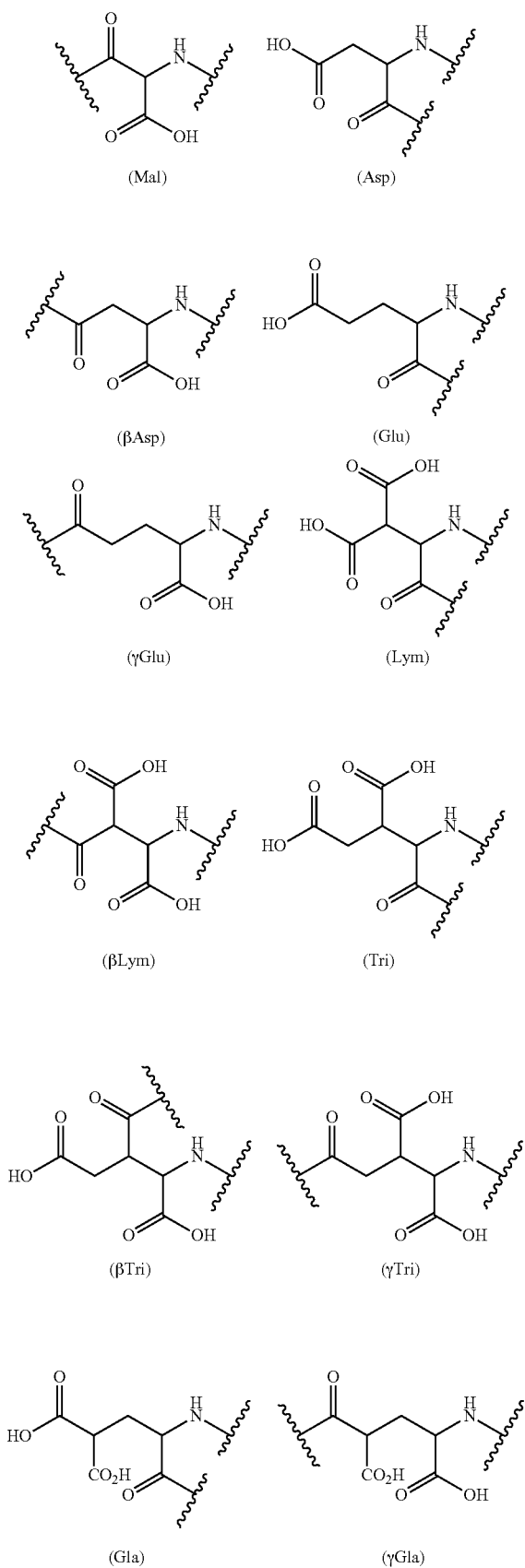
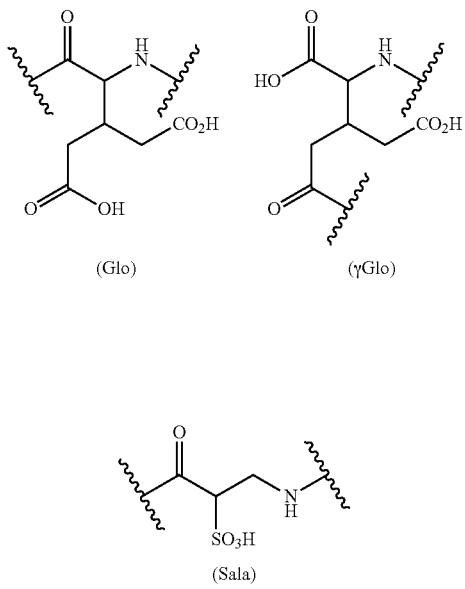

The preferred hydrophilic linkers may also be formed from two or more building blocks (m=2-5 in the generic formula), preferably selected from the acidic building blocks listed above. Preferred are 1-3 building blocks.

A number of preferred structures are listed in the table below:

| Number | Lipophilic Linker (=Linker A) | Hydrophilic Linker (=Linker B) | | | $^{18}$F-Tag |
|---|---|---|---|---|---|
| | | Pos. 1 | Pos. 2 | Pos. 3 | |
| 1 | (2-Nal)-(Bn) | (Glu) | (Glu) | — | [$^{18}$F]FN |
| 2 | (2-Nal) | (Glu) | (Glu) | — | [$^{18}$F]FN |
| 3 | (2-Nal) | (γGlu) | (Glu) | — | [$^{18}$F]FN |
| 4 | (2-Nal)-(Bn) | (Glu) | — | — | [$^{18}$F]FN |
| 5 | (2-Nal)-(AcAMP) | (γGlu) | (γGlu) | — | [$^{18}$F]FN |
| 6 | (2-Nal)-(Bn) | (Glu) | (γGlu) | — | [$^{18}$F]FN |
| 7 | (2-Nal)-(Bn) | (γGlu) | (Glu) | — | [$^{18}$F]FN |
| 8 | (2-Nal)-(Bn) | (γGlu) | (γGlu) | — | [$^{18}$F]FN |
| 9 | (2-Nal)-(Bn) | (Asp) | (Glu) | — | [$^{18}$F]FN |
| 10 | (2-Nal)-(Bn) | (βAsp) | (Glu) | — | [$^{18}$F]FN |
| 11 | (2-Nal)-(Bn) | (Asp) | (γGlu) | — | [$^{18}$F]FN |
| 12 | (2-Nal)-(Bn) | (βAsp) | (γGlu) | — | [$^{18}$F]FN |
| 13 | (2-Nal)-(Bn) | (Mal) | (Glu) | — | [$^{18}$F]FN |
| 14 | (2-Nal)-(Bn) | (Mal) | (γGlu) | — | [$^{18}$F]FN |
| 15 | (2-Nal)-(Bn) | (Gla) | (Glu) | — | [$^{18}$F]FN |
| 16 | (2-Nal)-(Bn) | (γGla) | (Glu) | — | [$^{18}$F]FN |
| 17 | (2-Nal)-(Bn) | (Gla) | (γGlu) | — | [$^{18}$F]FN |
| 18 | (2-Nal)-(Bn) | (γGla) | (γGlu) | — | [$^{18}$F]FN |

The structures of the preferred compounds 1-18 as exemplified in the table above are shown below:

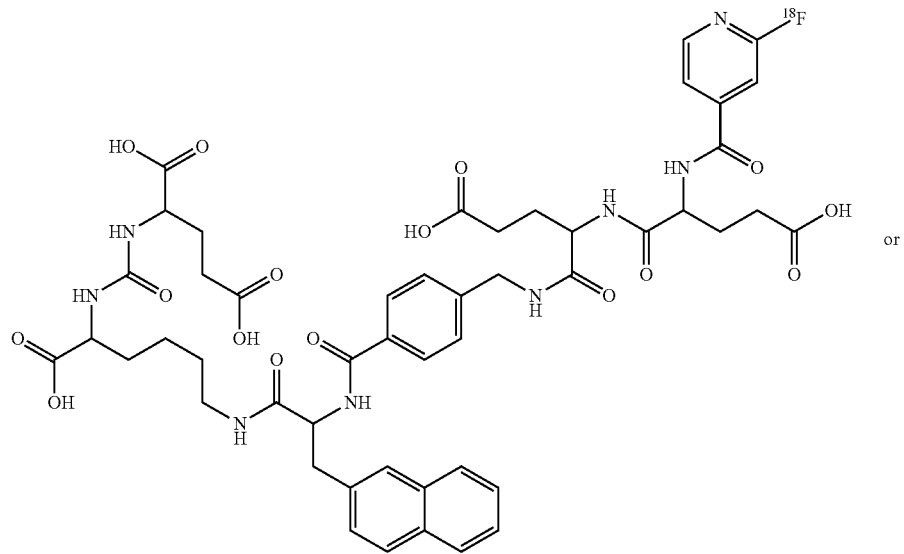
Number: 1a
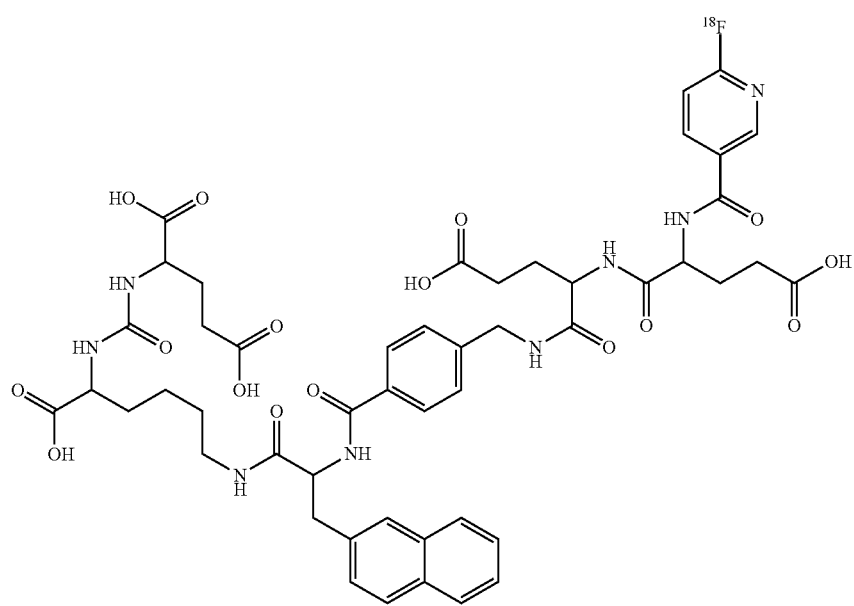
"PSMA 1007"
Number: 1

Number: 2
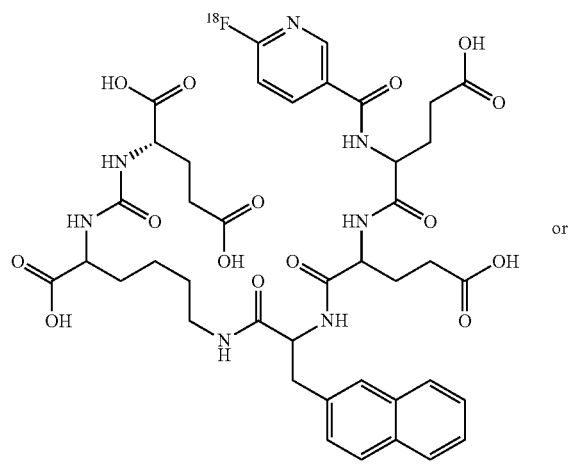
or
Number: 2a
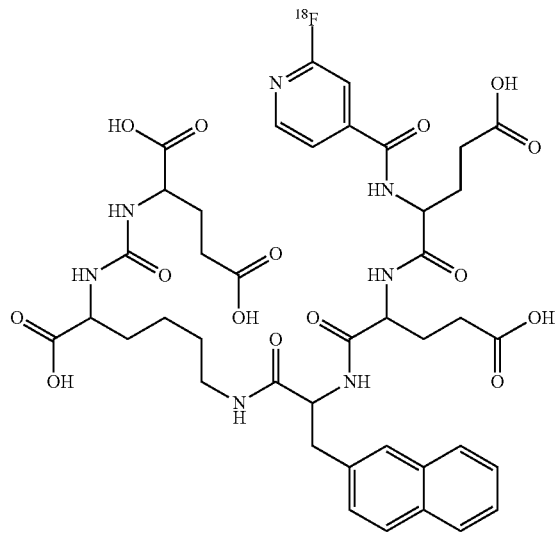
"PSMA1011"
Number: 3a
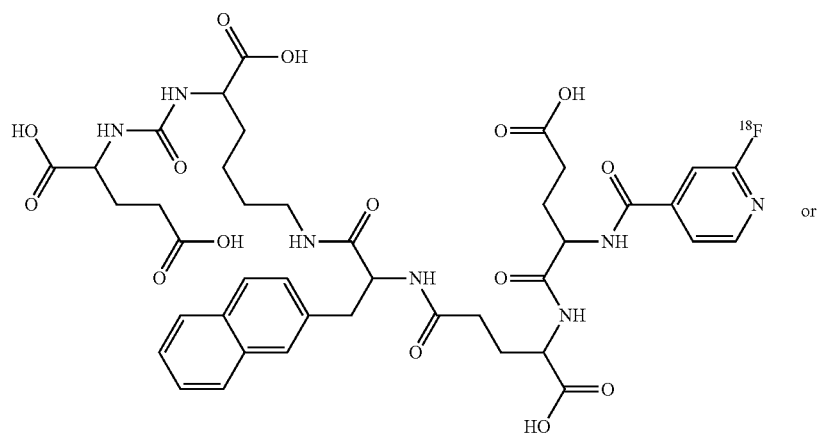
or
Number: 3
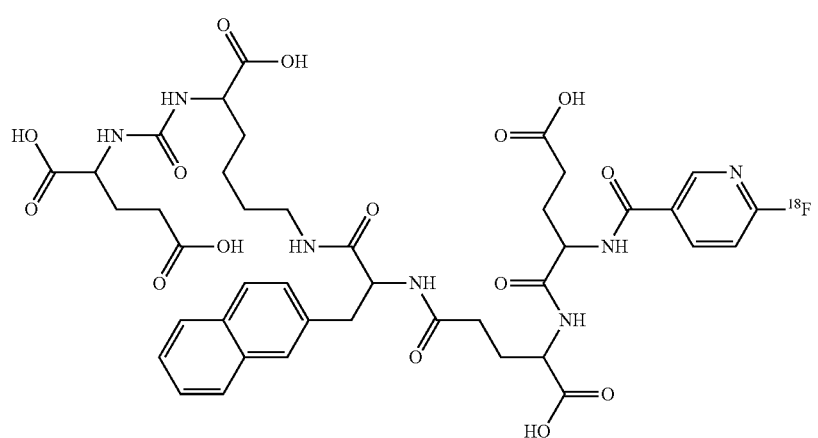
"PSMA1012"

-continued
Number: 4
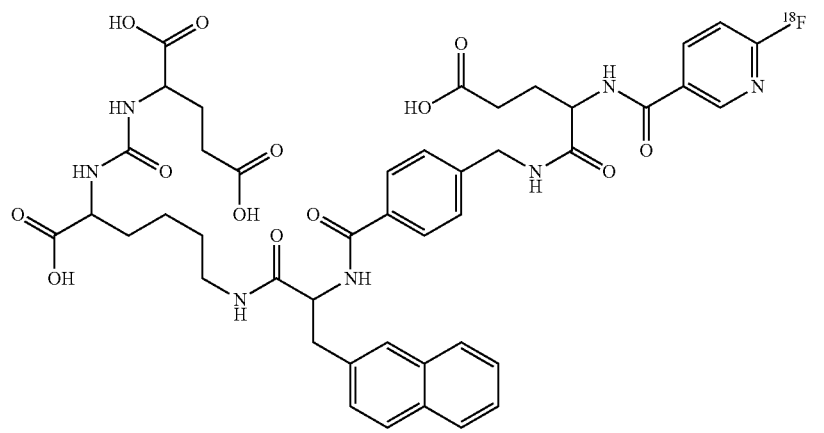
or
Number: 4a
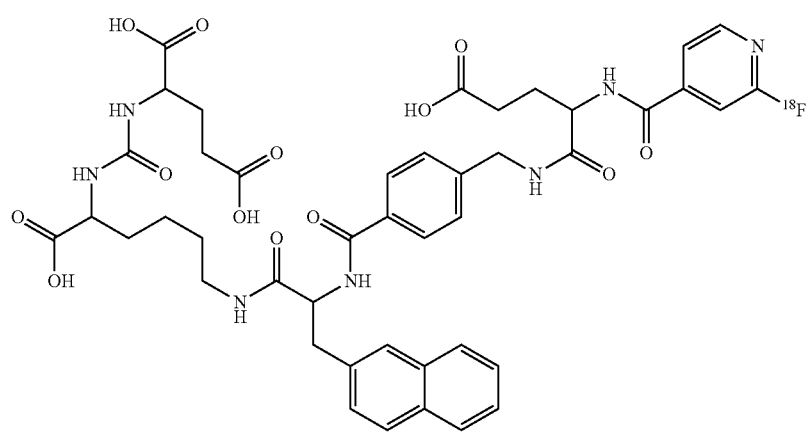
"PSMA1015"
Number: 5
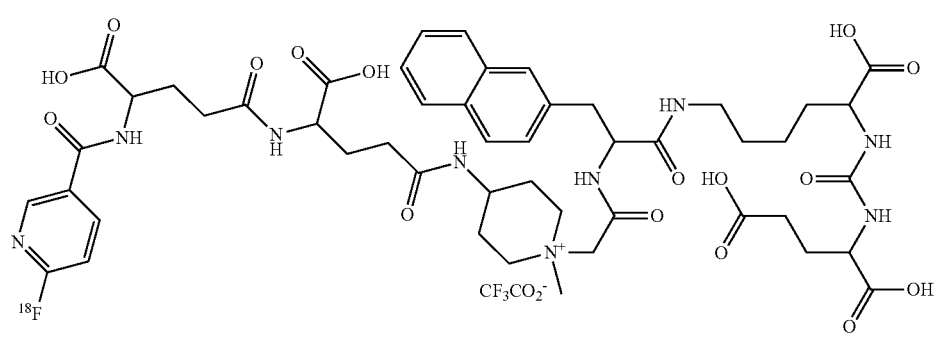
or
Number: 5a
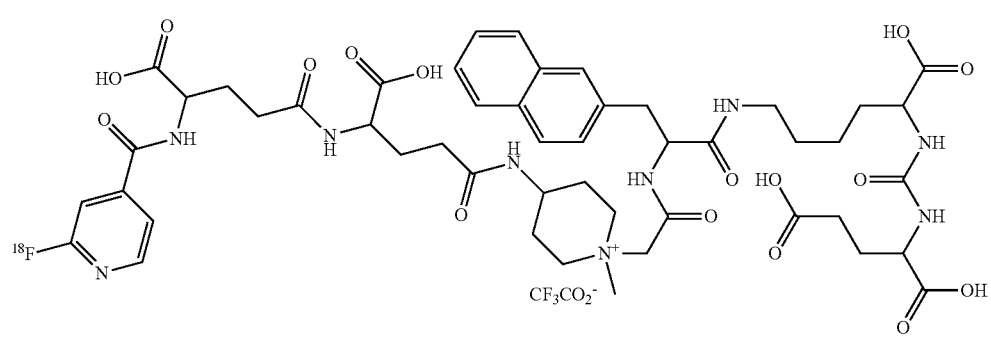

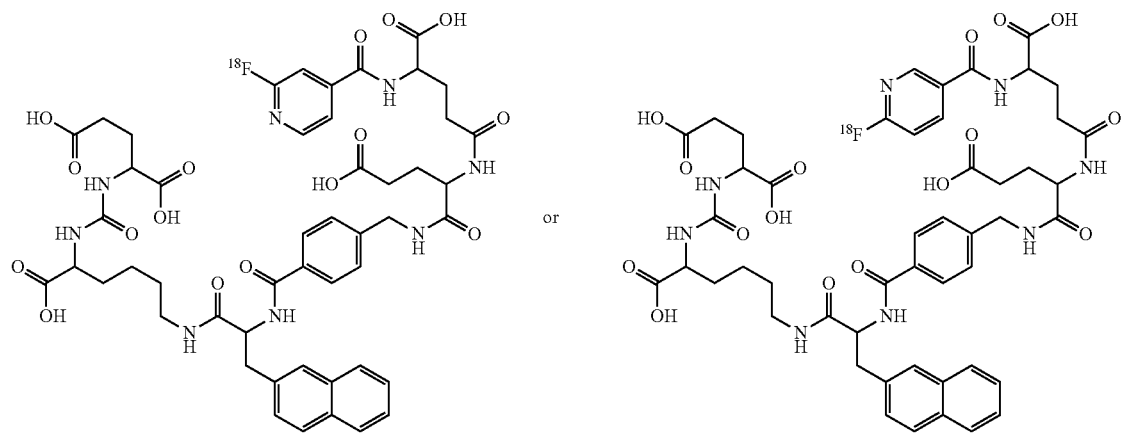
Number: 6a
Number: 6
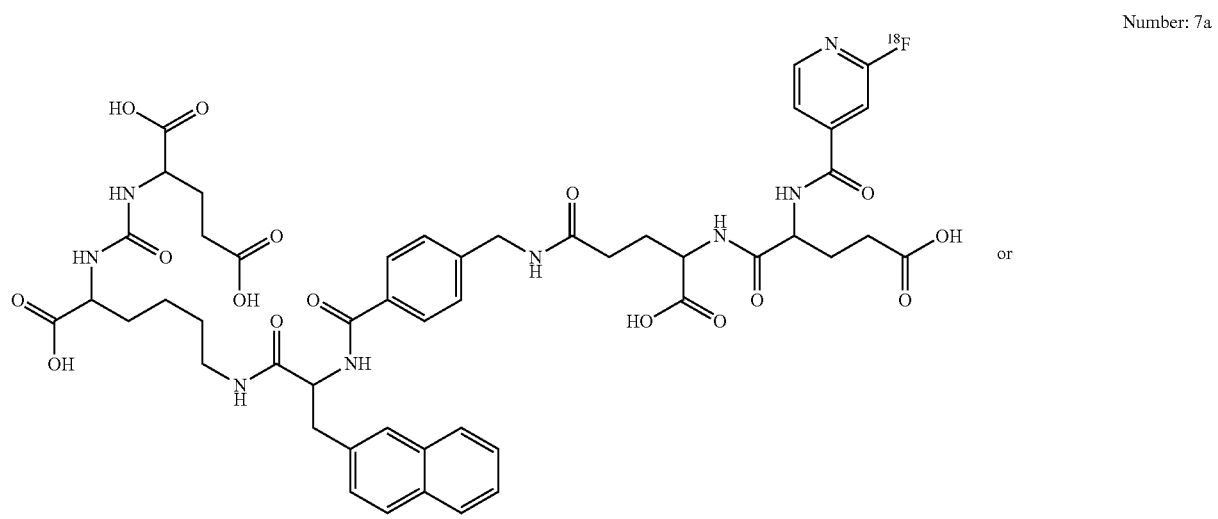
Number: 7a
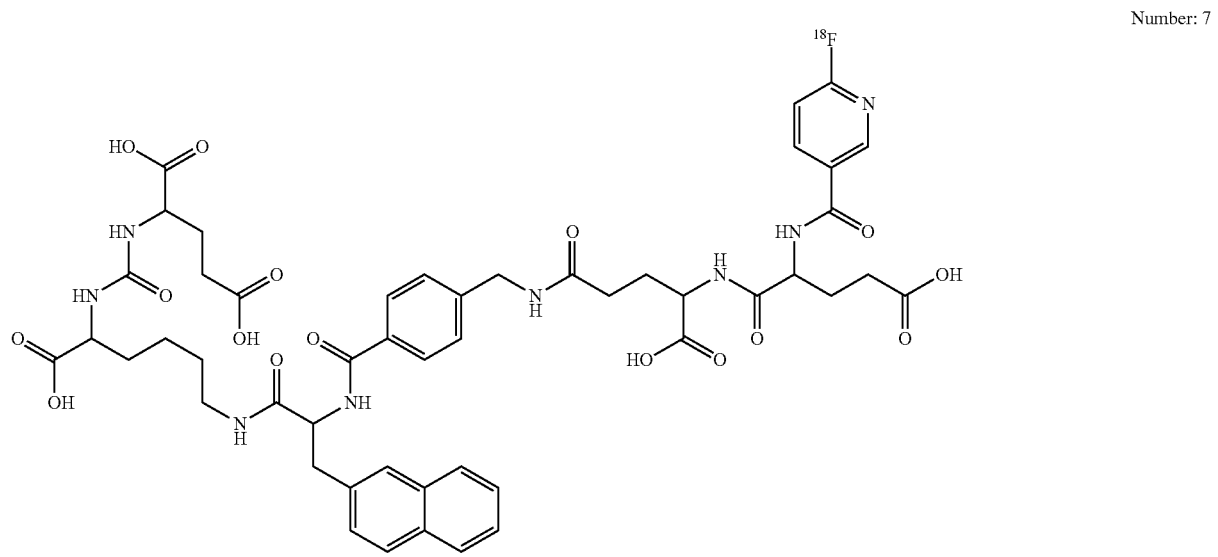
Number: 7

-continued
Number: 8a
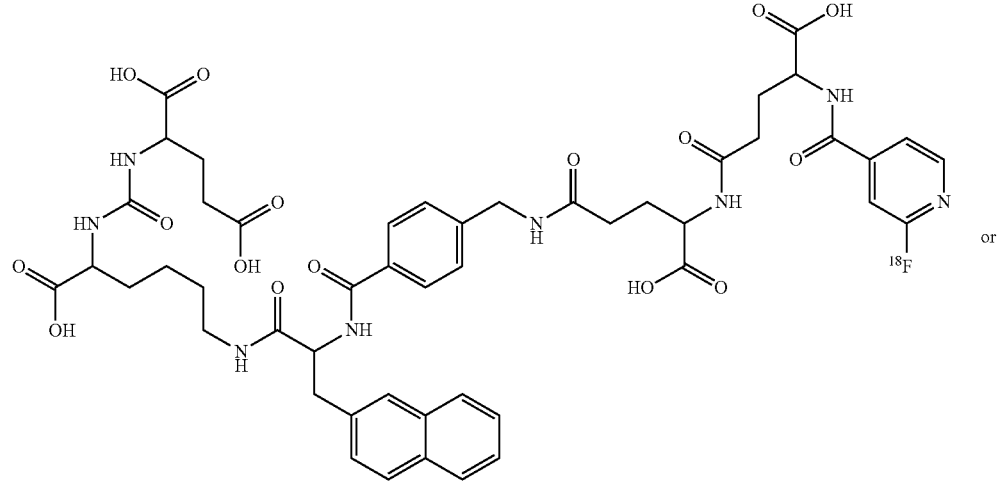
or
Number: 8
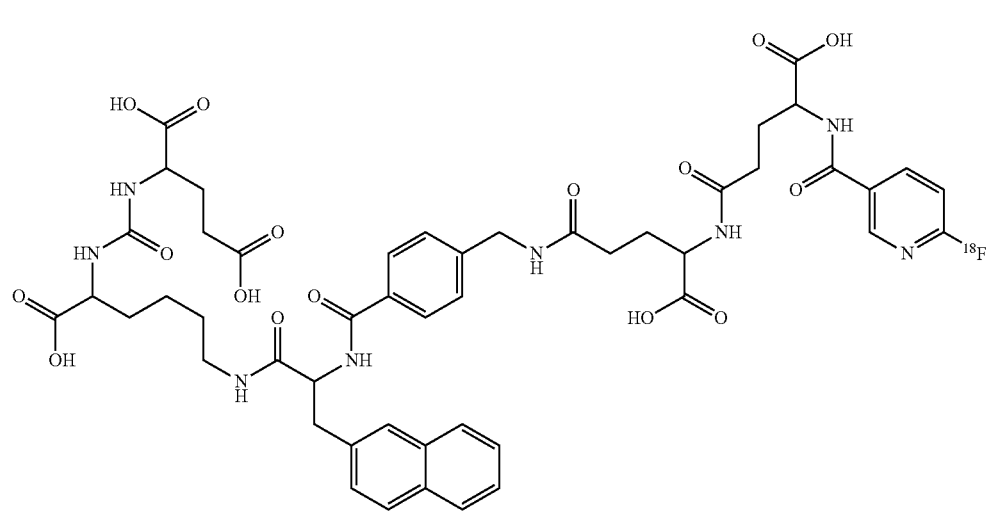
Number: 9a
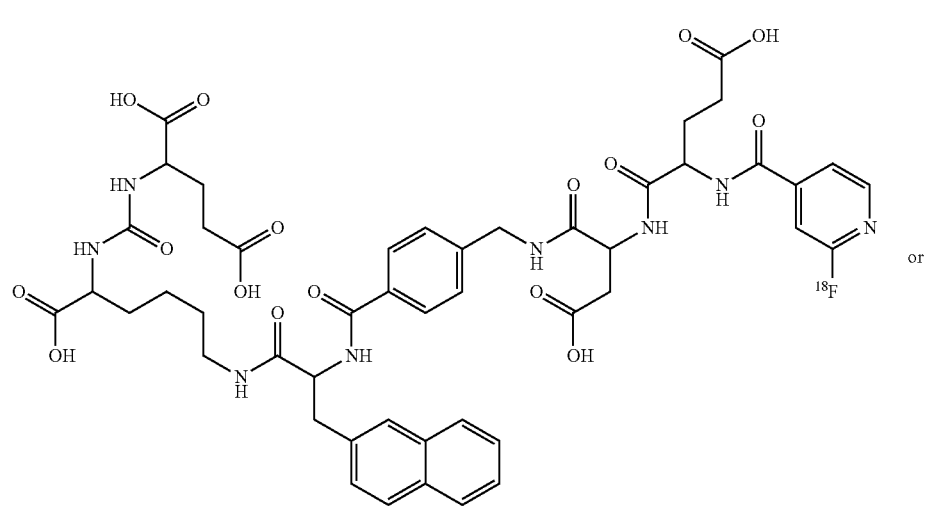
or -continued
Number: 9
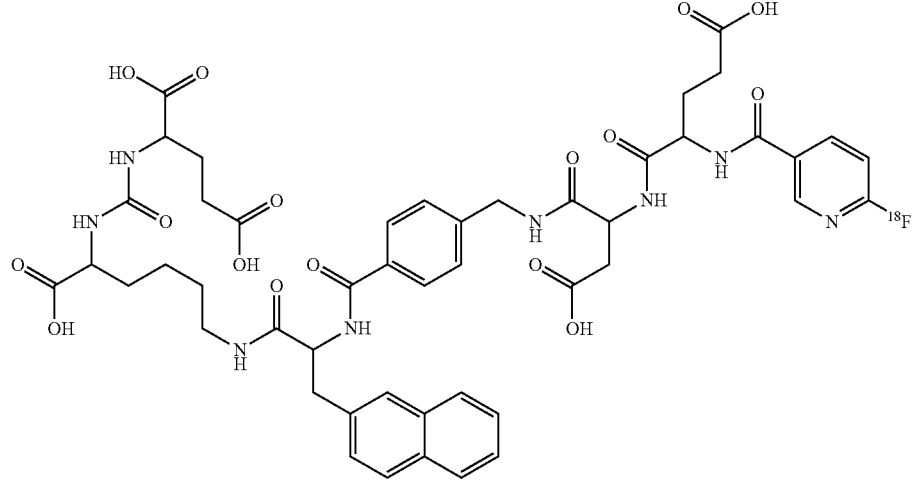
Number: 10a
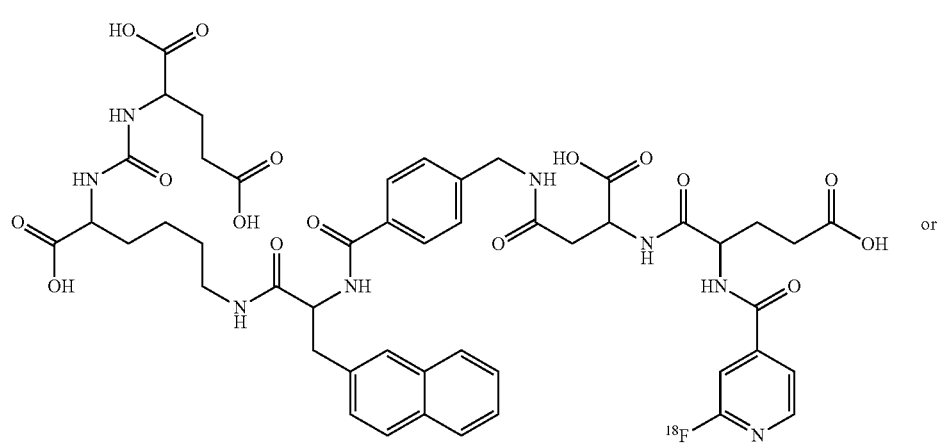
or
Number: 10
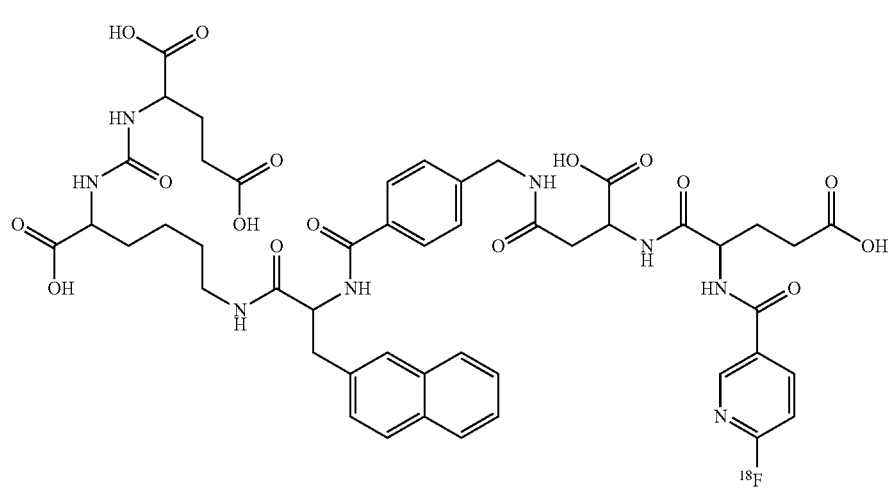

-continued
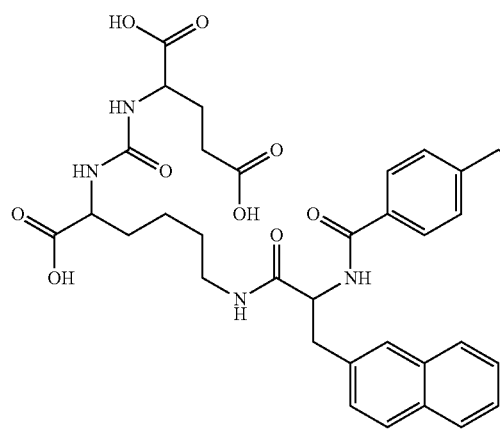 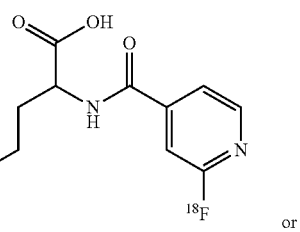
Number: 11a
or
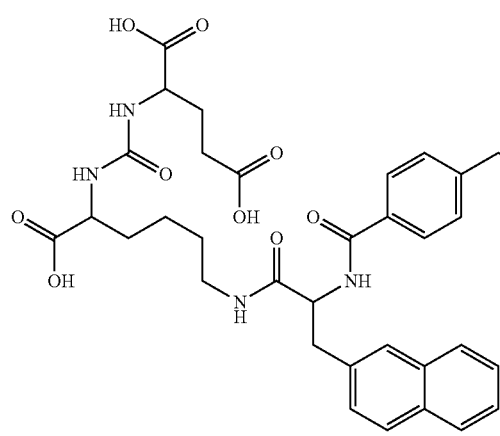 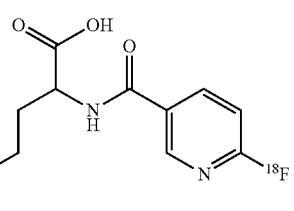
Number: 11
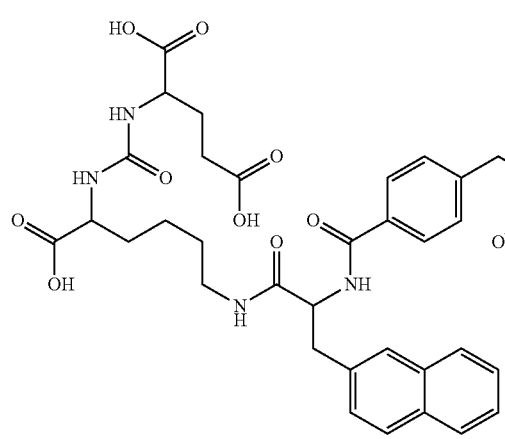 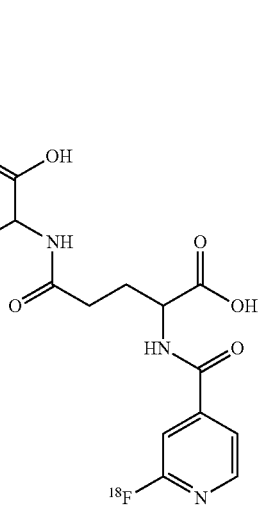
Number: 12a
or -continued
Number: 12
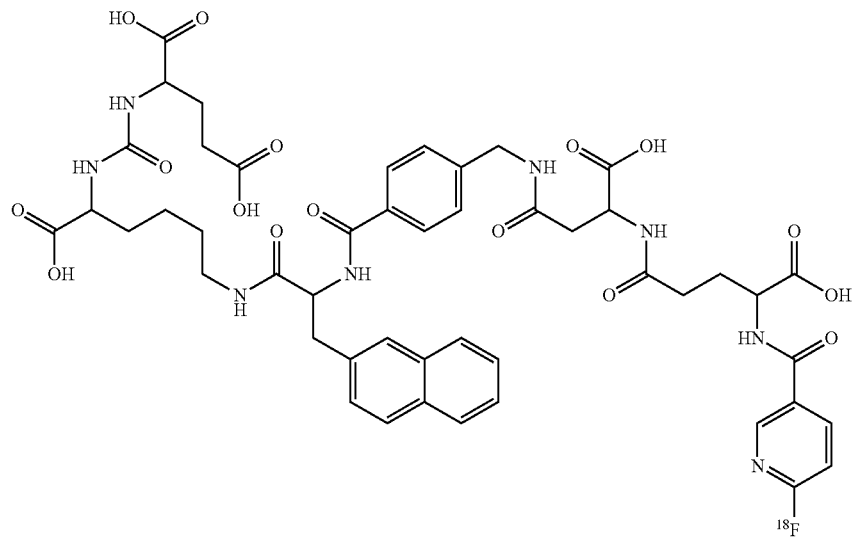
Number: 13a
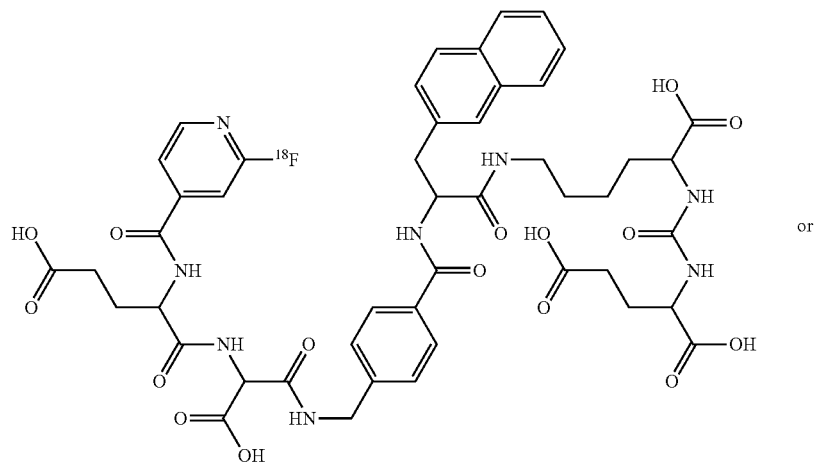
or
Number: 13
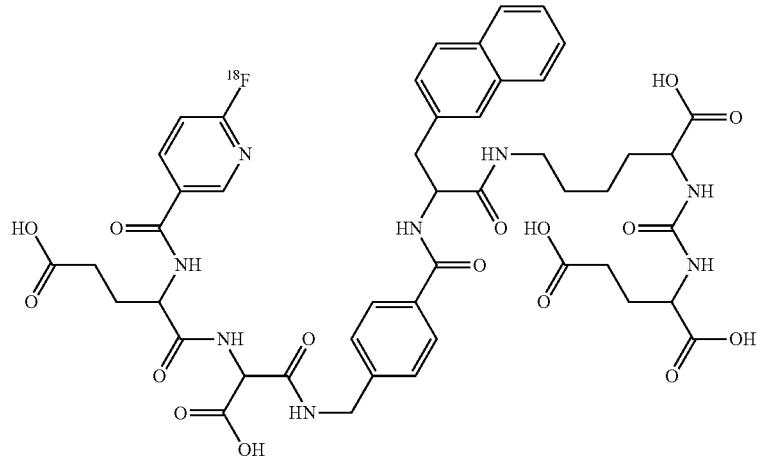

-continued
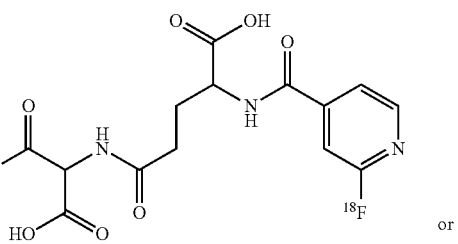
Number: 14a
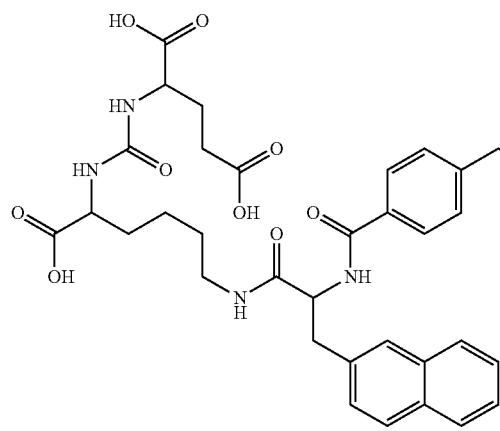
or
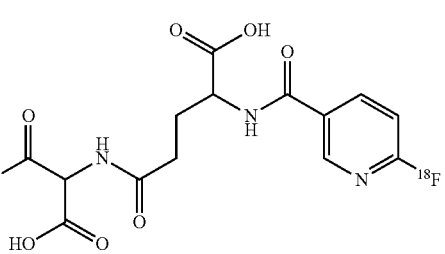
Number: 14
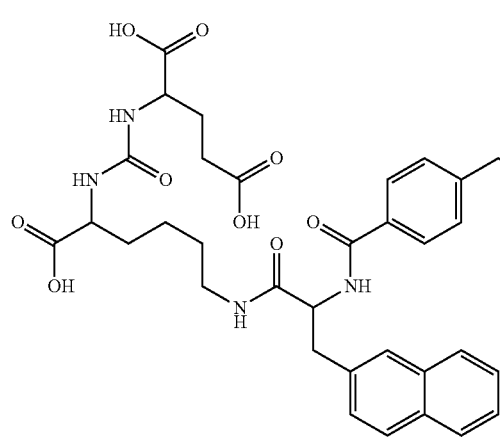
Number: 15a
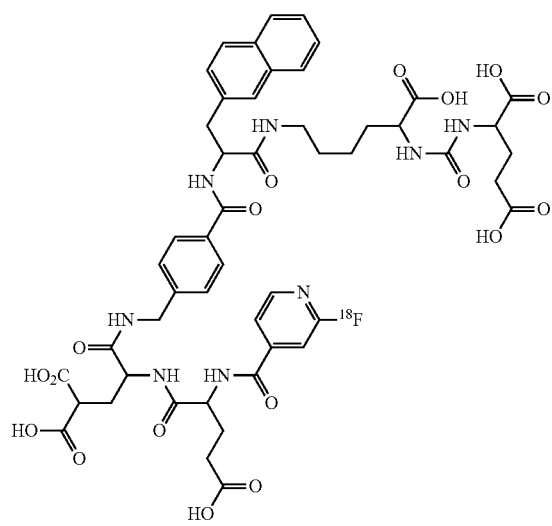
or
Number: 15
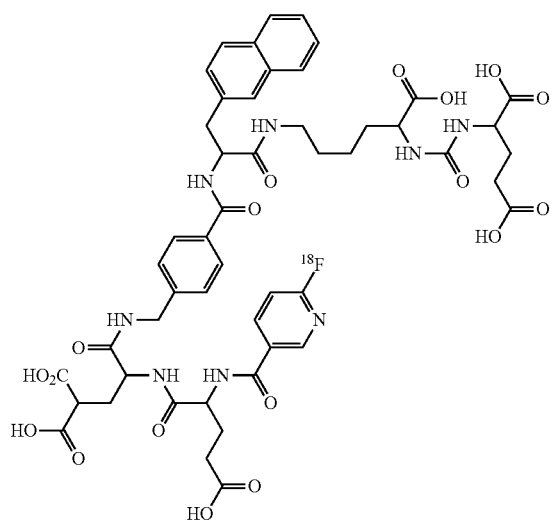

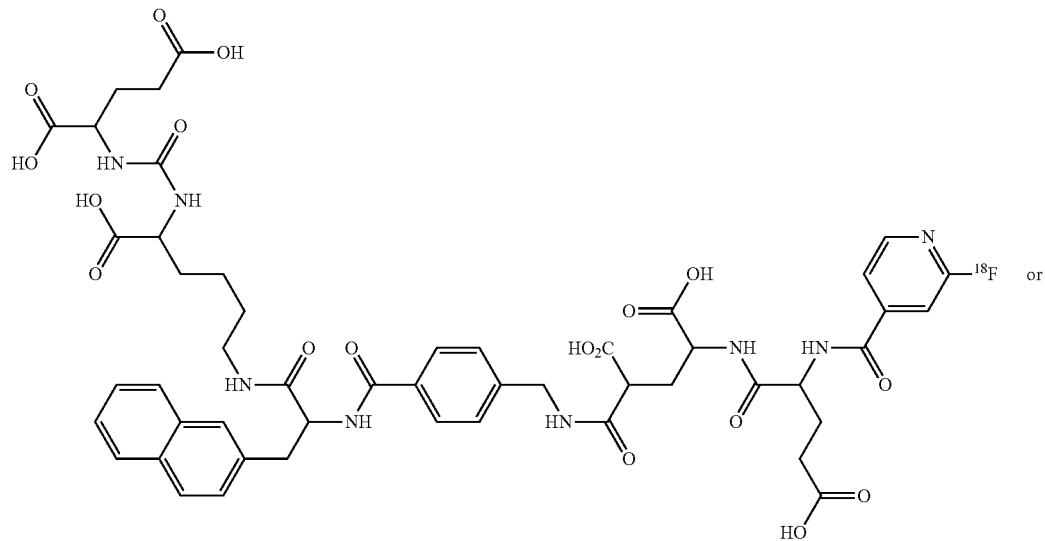
Number: 16a
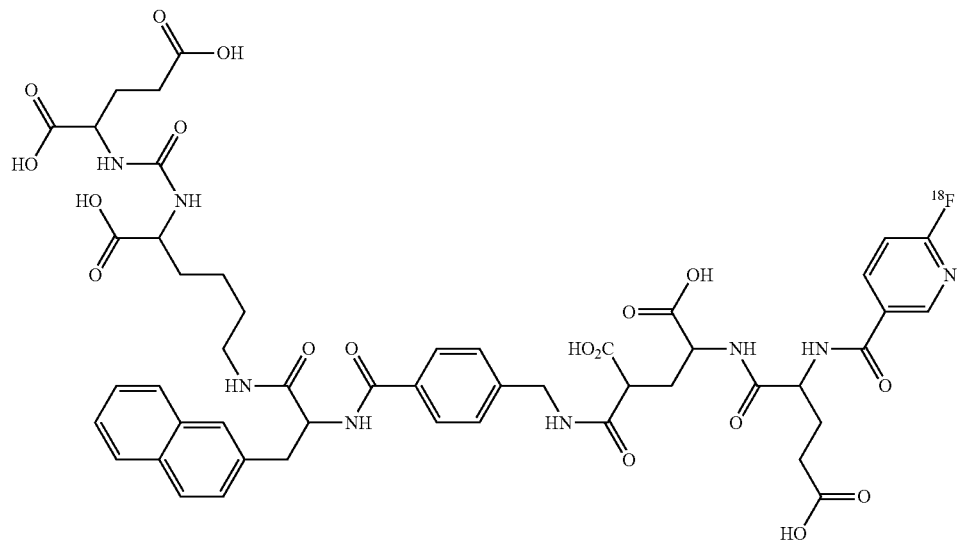
Number: 16

Number: 17a
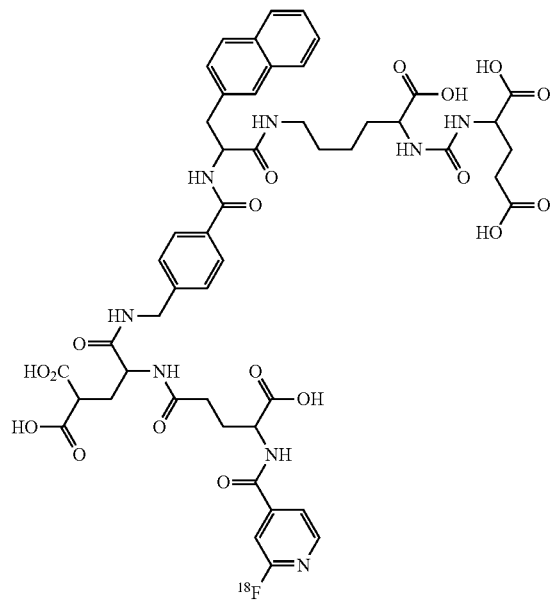
or
Number: 17
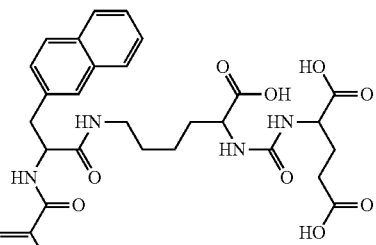
Number: 18a
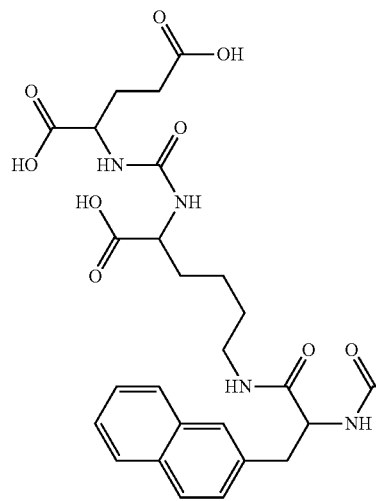
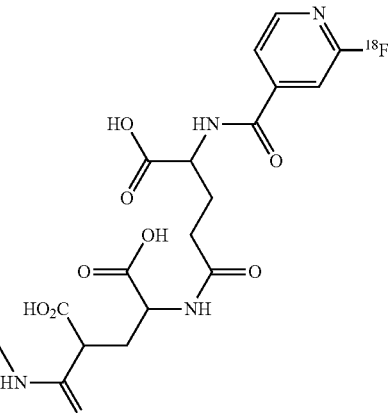
or
Number: 18
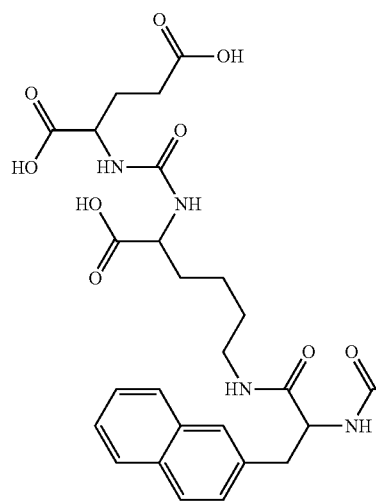
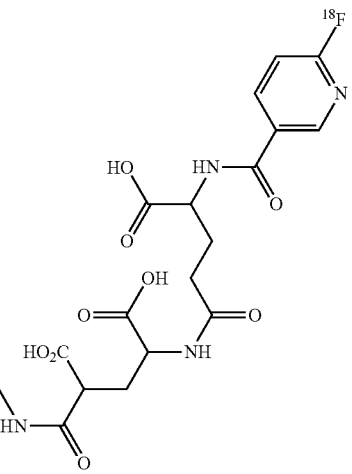

or

As may be understood by a person skilled in the art, the above mentioned preferred compounds 1-18 and 1a-18a are not limited to the $^{18}$F-Tags as shown but the $^{18}$F-Tags are easily interchangeable by standard techniques and any of the $^{18}$F-Tags exemplified in connection with Formula I may be used instead.

The invention also relates to precursors or pharmaceutically acceptable salts of the compounds of general formula I. The invention also relates to solvates of the compounds, including the salts as well as the active metabolites thereof and, where appropriate, the tautomers thereof according to general formula I including prodrug formulations.

A "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, carbonate, chloride, gluconate, glutamate, lactate, laurate, malate or tartrate.

The term "prodrug" refers to a precursor of a drug that is a compound which upon administration to a patient, must undergo conversion by metabolic processes before becoming an active pharmacological agent. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are converted into active drug within the body through enzymatic or non-enzymatic reactions. Prodrugs may provide improved physiochemical properties such as better solubility, enhanced delivery characteristics, such as specifically targeting a particular cell, tissue, organ or ligand, and improved therapeutic value of the drug.

Illustrative prodrugs of compounds in accordance with general formula I are esters and amides, preferably alkyl esters of fatty acid esters. Prodrug formulations here comprise all substances which are formed by simple transformation including hydrolysis, oxidation or reduction either enzymatically, metabolically or in any other way. A suitable prodrug contains e.g. a substance of general formula I bound via an enzymatically cleavable linker (e.g. carbamate, phosphate, N-glycoside or a disulfide group) to a dissolution-improving substance (e.g. tetraethylene glycol, saccharides, formic acids or glucuronic acid, etc.). Such a prodrug of a compound according to the invention can be applied to a patient, and this prodrug can be transformed into a substance of general formula I so as to obtain the desired pharmacological effect.

Some compounds of general formula I are encompassed in form of the racemates, their enantiomers and optionally in form of their diastereomers and all possible mixtures thereof.

According to the invention all chiral C-atoms shall have D- and/or L-configuration; also combinations within one compound shall be possible, i.e. some of the chiral C-atoms may be D- and others may be L-configuration.

The obtained compounds can be optionally separated by known methods (e.g. Allinger, N. L. and Elliel E. L. in "*Topics in Stereochemistry*" Vol. 6, Wiley Interscience, 1971) in their enantiomers and/or diastereomers. One possible method of enantiomeric separation is the use of chromatography.

The invention encompasses also precursors of the compounds of general formula I. The term "precursor" refers to any compound which can be used to produce the compounds of Formula I. An exemplary precursor may be a compound having no $^{18}$F-tag which is added at a later stage to provide the complete compound.

The invention also relates to pharmaceutical preparations which contain a diagnostically or therapeutically effective amount of the active ingredients (compound according to the invention of formula I) together with organic or inorganic solid or liquid, pharmaceutically acceptable carriers which are suited for the intended administration and which interact with the active ingredients without drawbacks.

The phrase "pharmaceutically acceptable" is employed herein to refer to those compounds, material, compositions, and/or dosage forms which are, within the scope of sound medical judgment, suitable for use in contact with the tissues of a patient without excessive toxicity, irritation, allergic response, or other problem or complication, commensurate with a reasonable benefit/risk ratio.

A "patient" includes an animal, such as a human, monkey, cow, horse, cat or dog. The animal can be a mammal such as a non-primate and a primate (e.g., monkey and human). In one embodiment, a patient is a human being.

In general, the formula I compound or pharmaceutical compositions thereof, may be administered orally or via a parenteral route, usually injection or infusion.

A "parenteral administration route" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticluare, subcapsular, subarachnoid, intraspinal and intrasternal injection and infusion.

The dosage of the compounds according to the invention is determined by the physician on the basis of the patient-specific parameters, such as age, weight, sex, severity of the disease, etc. Corresponding to the kind of administration, the medicament is suitably formulated, e.g. in the form of solutions or suspensions, simple tablets or dragees, hard or soft gelatine capsules, suppositories, ovules, preparations for injection, which are prepared according to common galenic methods.

The compounds according to the invention can be formulated, where appropriate, together with further active substances and with excipients and carriers common in pharmaceutical compositions, e.g.—depending on the preparation to be produced—talcum, gum arabic, lactose, starch, magnesium stearate, cocoa butter, aqueous and non-aqueous carriers, fatty bodies of animal or vegetable origin, paraffin derivatives, glycols (in particular polyethylene glycol), various plasticizers, dispersants or emulsifiers, pharmaceutically compatible gases (e.g. air, oxygen, carbon dioxide, etc.), preservatives. In order to produce liquid preparations, additives, such as sodium chloride solution, ethanol, sorbitol, glycerine, olive oil, almond oil, propylene glycol or ethylene glycol, can be used.

When solutions for infusion or injection are used, they are preferably aqueous solutions or suspensions, it being possible to produce them prior to use, e.g. from lyophilized preparations which contain the active substance as such or together with a carrier, such as mannitol, lactose, glucose, albumin and the like. The ready made solutions are sterilized and, where appropriate, mixed with excipients, e.g. with preservatives, stabilizers, emulsifiers, solubilizers, buffers and/or salts for regulating the osmotic pressure. The sterilization can be obtained by sterile filtration using filters having a small pore size according to which the composition can be lyophilized, where appropriate. Small amounts of antibiotics can also be added to ensure the maintenance of sterility.

The phrases "effective amount" or "therapeutically-effective amount" as used herein means that amount of a compound, material, or composition comprising a compound of the invention, or other active ingredient which is effective for producing some desired therapeutic effect in at least a sub-population of cells in an animal at a reasonable benefit/risk ratio applicable to any medical treatment. A therapeutically effective amount with respect to a compound of the invention means that amount of therapeutic agent alone, or in combination with other therapies, that provides a therapeutic benefit in the treatment of prevention of a disease. Used in connection with a compound of the invention, the term can encompass an amount that improves overall therapy, reduces or avoids symptoms or causes of disease, or enhances the therapeutic efficacy of or synergies with another therapeutic agent.

As used herein, the terms "treating" or "treatment" is intended to encompass also diagnosis, prophylaxis, prevention, therapy and cure.

The terms "prevent", "preventing," and "prevention" refer to the prevention of the onset, recurrence, or spread of the disease in a patient resulting from the administration of a prophylactic or therapeutic agent.

As noted above, compounds according general formula I are suitable for use as radio-imaging agents or as therapeutics for the treatment of rapidly proliferating cells, for example, PSMA expressing prostate cancer cells. According to the present invention they are called "radiopharmaceuticals".

Preferred imaging methods are positron emission tomography (PET) or single photon emission computed tomography (SPECT).

Accordingly, in one embodiment, a pharmaceutical composition is provided including a compound of formula I, a salt, solvate, stereoisomer, or tautomer thereof, and a pharmaceutically acceptable carrier. Accordingly, a pharmaceutical composition is provided, which is suitable for in vivo imaging and radiotherapy. Suitable pharmaceutical compositions may contain the compound of formula I in an amount sufficient for imaging, together with a pharmaceutically acceptable radiological vehicle. The radiological vehicle should be suitable for injection or aspiration, such as human serum albumin; aqueous buffer solutions, e.g., tris(hydromethyl) aminomethane (and its salts), phosphate, citrate, bicarbonate, etc; sterile water physiological saline; and balanced ionic solutions containing chloride and or dicarbonate salts or normal blood plasma cautions such as calcium potassium, sodium and magnesium.

The concentration of the imaging agent or the therapeutic agent in the radiological vehicle should be sufficient to provide satisfactory imaging. For example, when using an aqueous solution, the dosage is about 1.0 to 100 millicuries. The actual dose administered to a patient for imaging or therapeutic purposes, however, is determined by the physician administering treatment. The imaging agent or therapeutic agent should be administered so as to remain in the patient for about 1 hour to 10 days, although both longer and shorter time periods are acceptable. Therefore, convenient ampoules/vials containing 1 to 10 mL of aqueous solution may be prepared.

Imaging may be carried out in the normal manner, for example by injecting a sufficient amount of the imaging composition to provide adequate imaging and then scanning with a suitable imaging or scanning machine, such as a tomograph or gamma camera. In certain embodiments, a method of imaging a region in a patient includes the steps of: (i) administering to a patient a diagnostically effective amount of a compound labeled with a radionuclide; exposing a region of the patient to the scanning device; and (ii) obtaining an image of the region of the patient.

The amount of the compound of the present invention, or its salt, solvate, stereoisomer, or tautomer that is administered to a patient depends on several physiological factors that are routinely used by the physician, including the nature of imaging to be carried out, tissue to be targeted for imaging or therapy and the body weight and medical history of the patient to be imaged or treated using a radiopharmaceutical.

Specifically, the cell proliferative disease or disorder to be treated or imaged using a compound, pharmaceutical composition or radiopharmaceutical in accordance with this invention is a cancer, for example, prostate cancer and/or prostate cancer metastasis in e.g. lung, liver, kidney, bones, brain, spinal cord, bladder, etc.

The synthesis of the compounds of the present invention is carried out according to methods well known in the prior art (e.g. Hugenberg et al., J. Med. Chem. 2013, 56, pp. 6858-6870). General methods for $^{18}$F-labelling of various macromolecules are shown in FIG. 1-7. In addition, reference is made to Schubiger et al., PET Chemistry: The Driving Force in Molecular Imaging, Ernst Schering Research Foundation, Workshop 62, Springer Verlag, ISSN 0947-6075; Ross et al., Current Radiopharmaceuticals, 2010, 3, 202-223; Kühnast et al., Current Radiopharm 3, 2010, 174; Bernard-Gauthier et al., BioMed Research International, 2014, 1; Maschauer and Prante, BioMed Research International, 2014, 1; Olberg et al., J. Med. Chem., 2010, 53, 1732; Rostovtsev et al., Angew. Chem., 2002, 114, 2708; Smith and Greaney, Org. Lett., 2013, 15, 4826. Thus, a person skilled in the art would be able to choose the right $^{18}$F-labelling depending on the starting molecule. The synthesis of the specific linker molecules is shown in EP 13004991 to which reference is made.

The synthesized compounds are chemically characterized by RP-HPLC, MS, and/or NMR.

The novel $^{18}$F-tagged imaging agents with structural modifications in the linker region have improved tumor targeting properties and pharmacokinetics. The pharmacophore presents three carboxylic group able to interact with the respective side chains of PSMA and an oxygen as part of zinc complexation in the active center. Besides these obligatory interactions, the inventors were able to optimize the lipophilic interactions in the linker region compared to the compounds as described in EP 14003570.0. Further hydrophilic building blocks have been added to the linker of the compounds of the present invention (linker B), leading to another enhancement of the pharmacokinetics. Those compounds were evaluated in in vitro assays (affinity, internalization) and in vivo experiments (pPET screening and organ distribution).

Four preferred compounds with particularly promising results are $^{18}$F-PSMA1007, $^{18}$F-PSMA1011, $^{18}$F-PSMA 1012 and $^{18}$F-PSMA 1015:

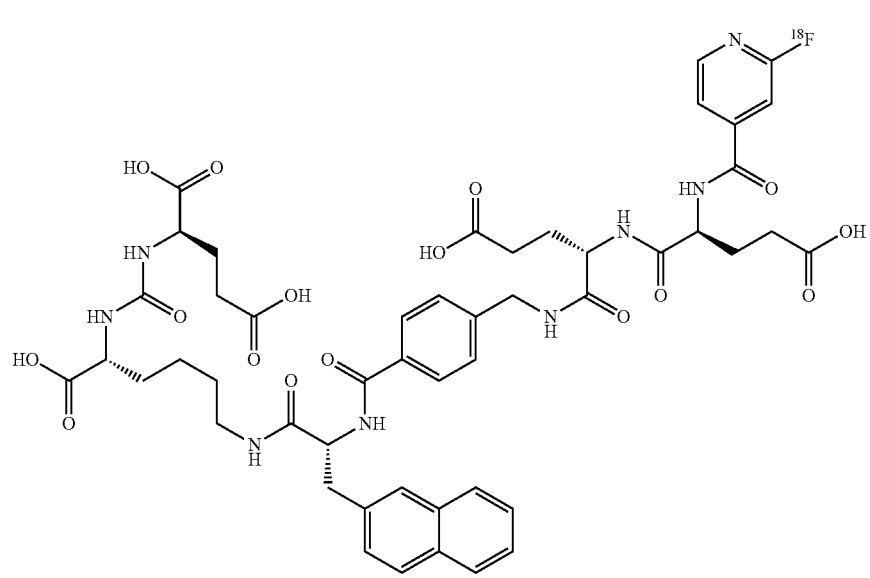
PSMA-1007
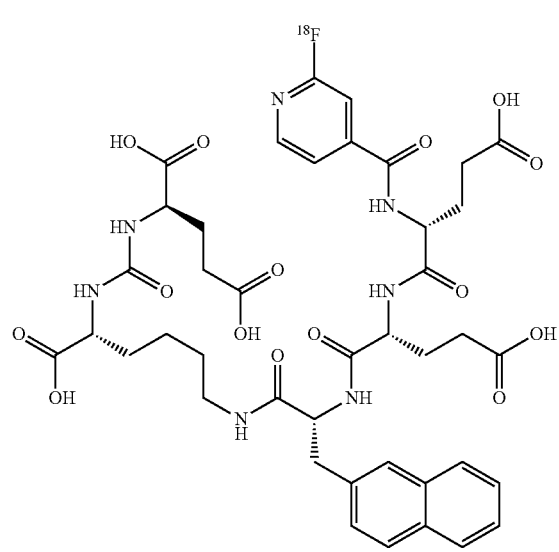
PSMA-1011
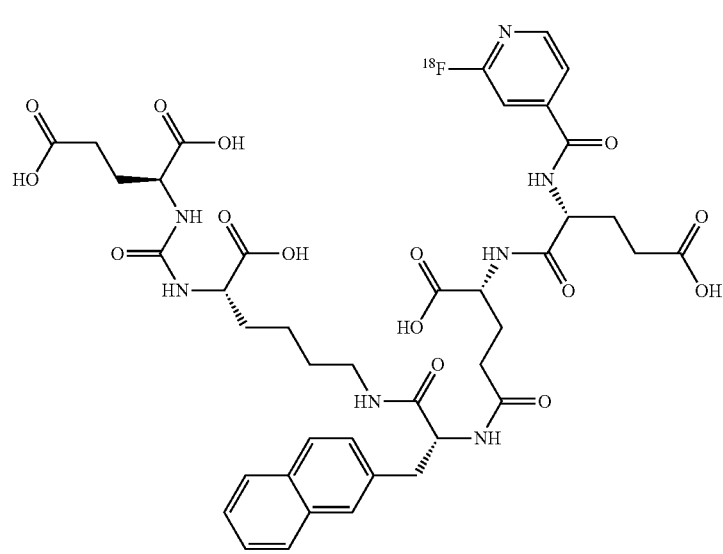
PSMA-1012

-continued
PSMA-1015
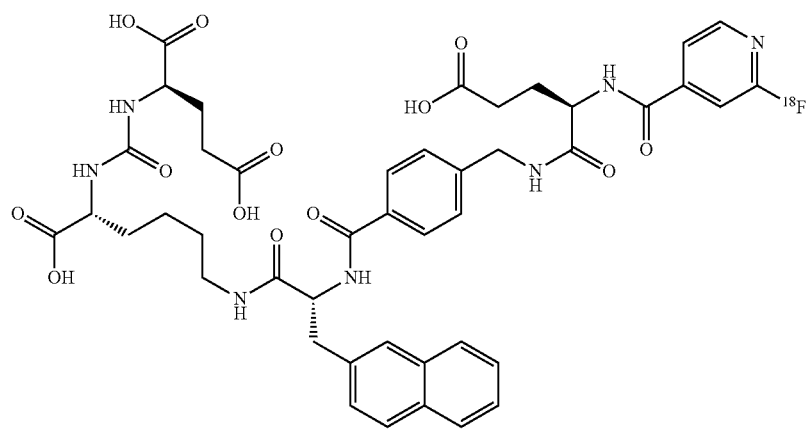
PSMA-1007
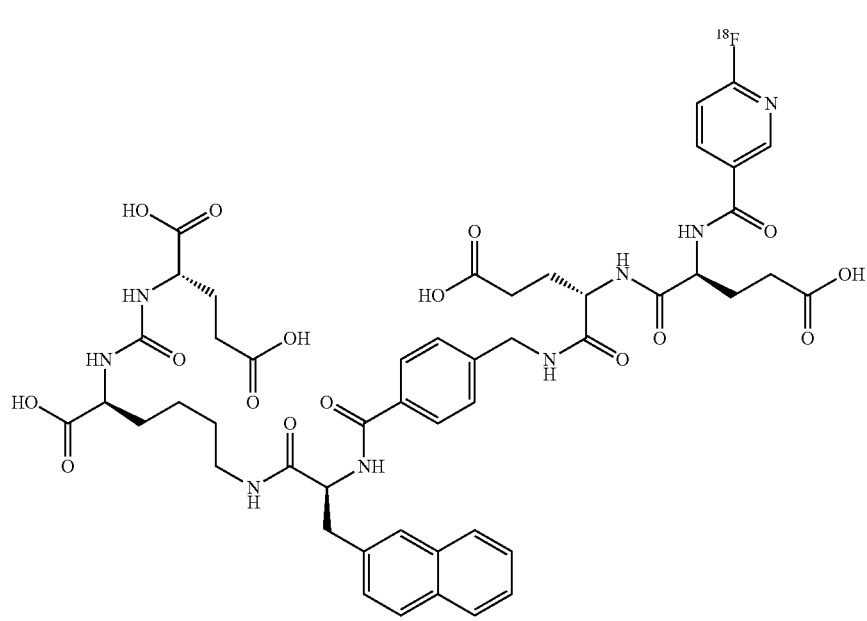
PSMA-1011
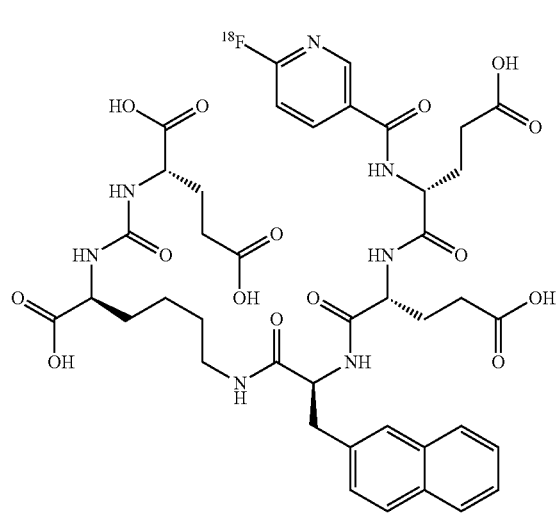

-continued

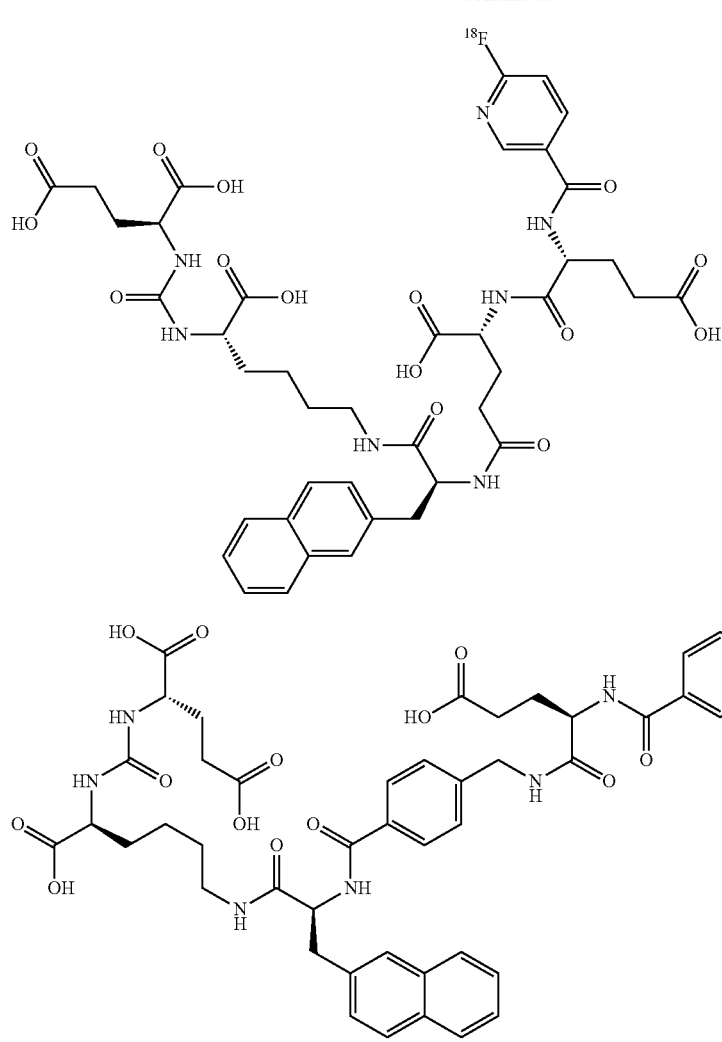

All compounds were labelled with fluorine-18 via 2-[$^{18}$F] fluoronicotinic acid TFP ester in good radiochemical yields. Table A shows that the binding affinity of the PSMA inhibitors prepared so far are essentially the same and in the typical range. Further, all compounds were specifically internalized at 37° C. with rather high cell uptake and internalization values (Table B). Thus, the compounds investigated exhibit optimal in vitro characteristics for a high contrast PET imaging.

Figure 8:
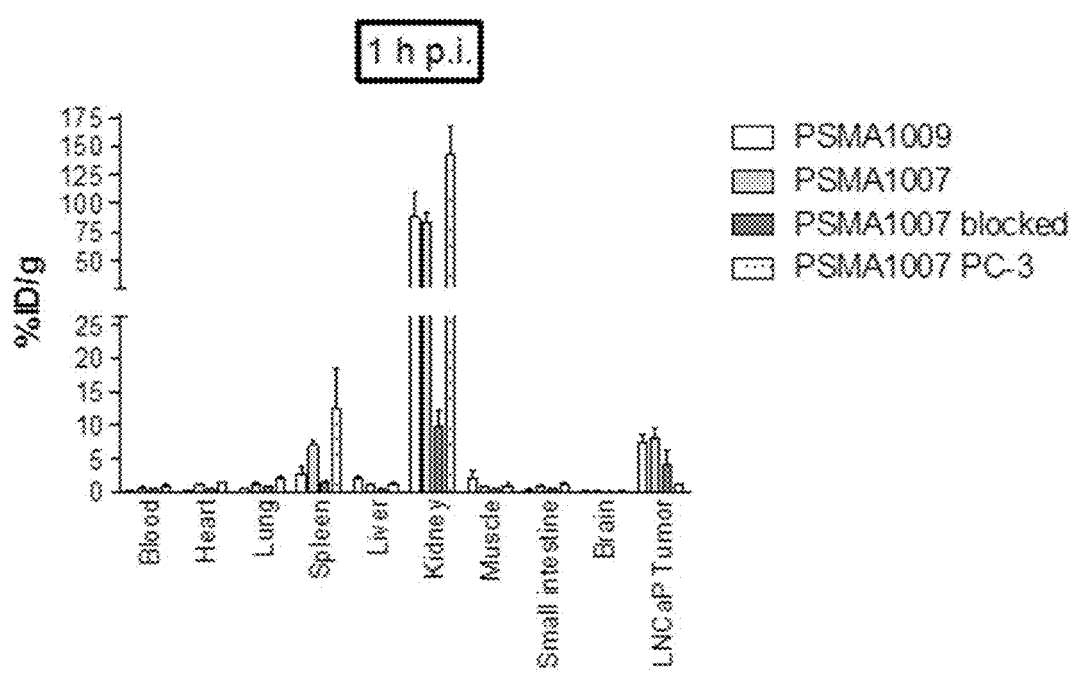
FIG. 8: Organ distribution of [$^{18}$F]PSMA-1007 in PSMA-positive LNCaP mice (normal and blocked) and in PSMA negative PC3 mice vs. [$^{18}$F]PSMA-1009 ([$^{18}$F]DCFPyL) in PSMA positive LNCaP mice
Figure 9:
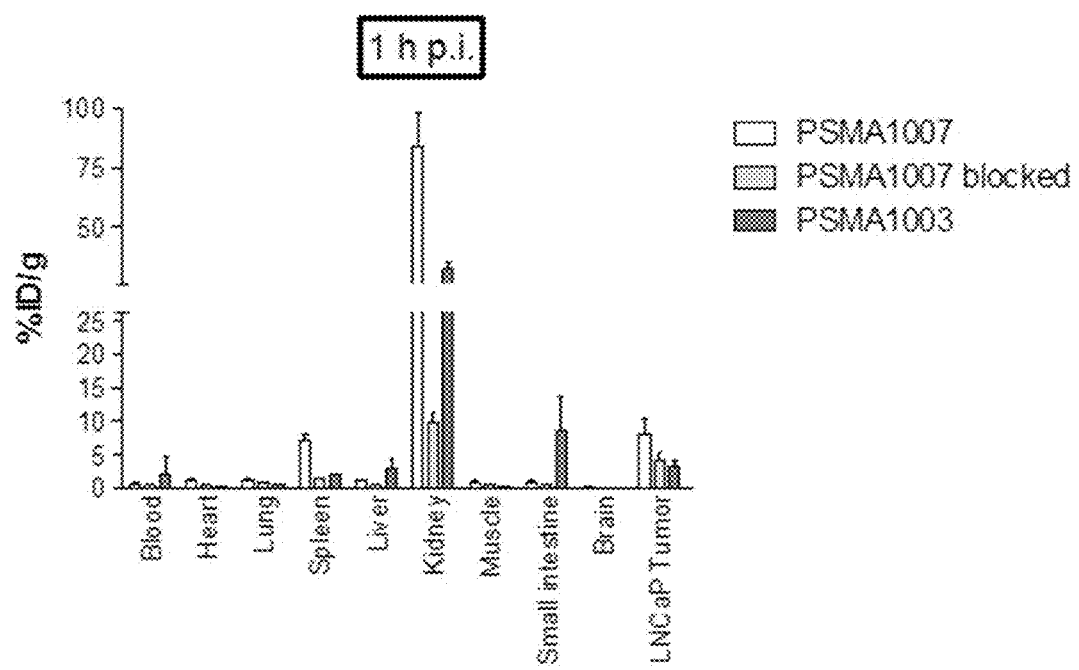
FIG. 9: Organ distribution of [$^{18}$F]PSMA-1007 in PSMA-positive LNCaP mice (non-blocked and blocked) vs. [$^{18}$F]PSMA1003 in PSMA positive LNCaP mice (non-blocked)
Figure 10:
FIG. 10: MIP of [$^{18}$F]PSMA-1007 in a PSMA-positive LNCaP mouse 120-140 min p.i.
Figure 11:
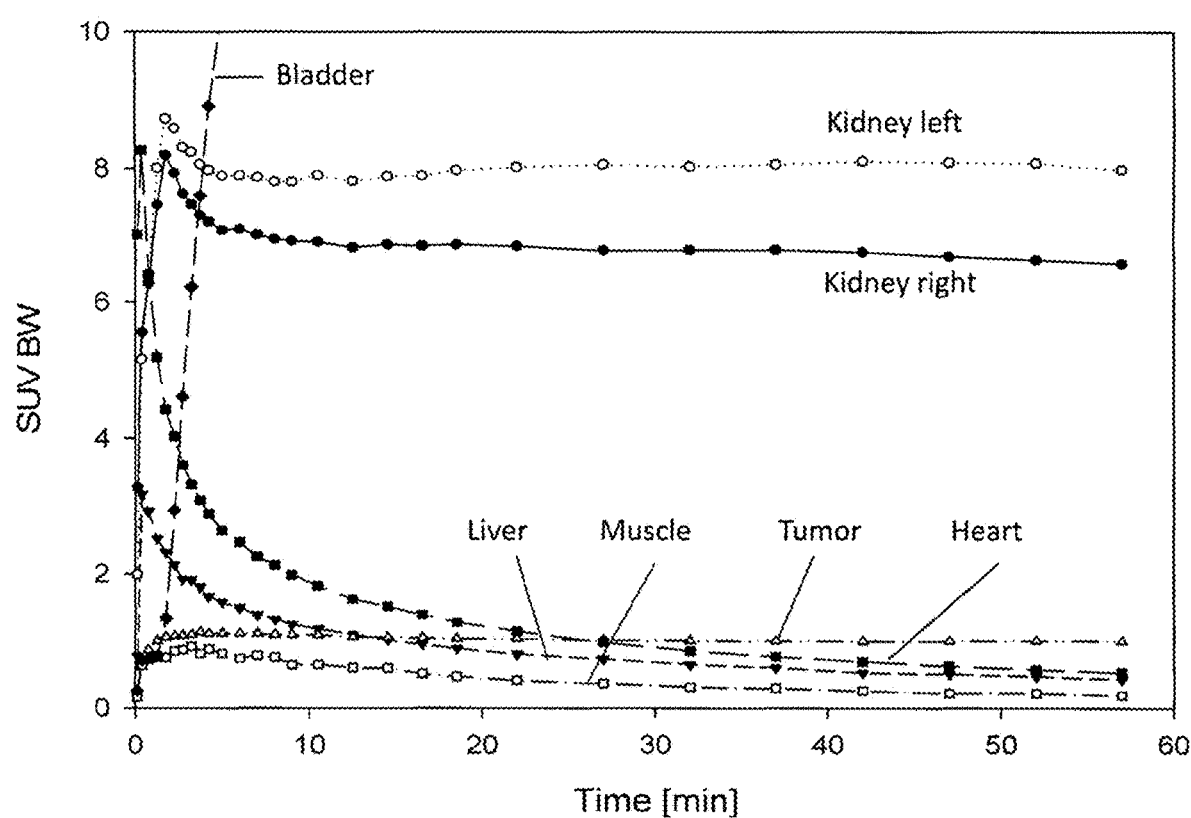
FIG. 11: Time-activity curve of [$^{18}$F]PSMA-1007 in a PSMA-positive LNCaP mouse, including SUV values 120-140 min p.i.
Figure 12:
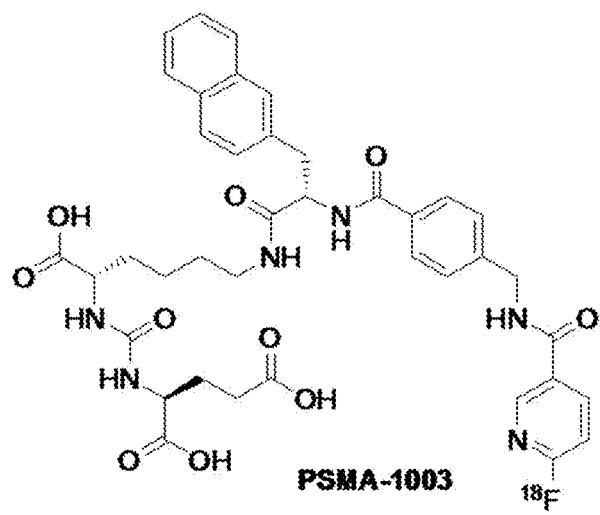
FIG. 12: Structure of PSMA-1003

The compounds of the present invention were investigated in organ distribution studies in mice carrying a LNCaP tumor (PSMA positive) with and without PMPA block. The results which have been obtained exemplary with PSMA1007 (this does not mean that the invention is limited in any way to this specific compound only) are summarised in the FIGS. 8 and 9. The tumor uptake was about 8.0±2.4% ID/g. Since a quantitative blocking of the binding was not observed in the blocking experiment, the organ distribution experiment was repeated with mice carrying a PC3-tumor (PSMA negative; Results shown FIG. 8). Here, practically no tumor uptake was observed. Thus, the tumor uptake is considered specifically. Additionally, compared to the organ distribution observed with the control compound PSMA-1003 which has been described in EP 14 003 570.0 and is shown in FIG. 12, the novel compound PSMA-1007 showed a significantly reduced uptake in non-target tissue such as the liver and the small intestine. Thus, PSMA-1007 was further evaluated in microPET experiment. The results are shown in FIGS. 10 and 11. The LNCaP tumor was clearly visualised in this experiment ($SUV_{max}$=3.1 at 120-140 min p.i.). The undesired uptake in the gallbladder may be an indicator for metabolites. Overall the novel class of fluorine-18 labelled PSMA inhibitors showed a great potential as possible tracer for the detection of prostate cancer and its metastases.

Figure 14:
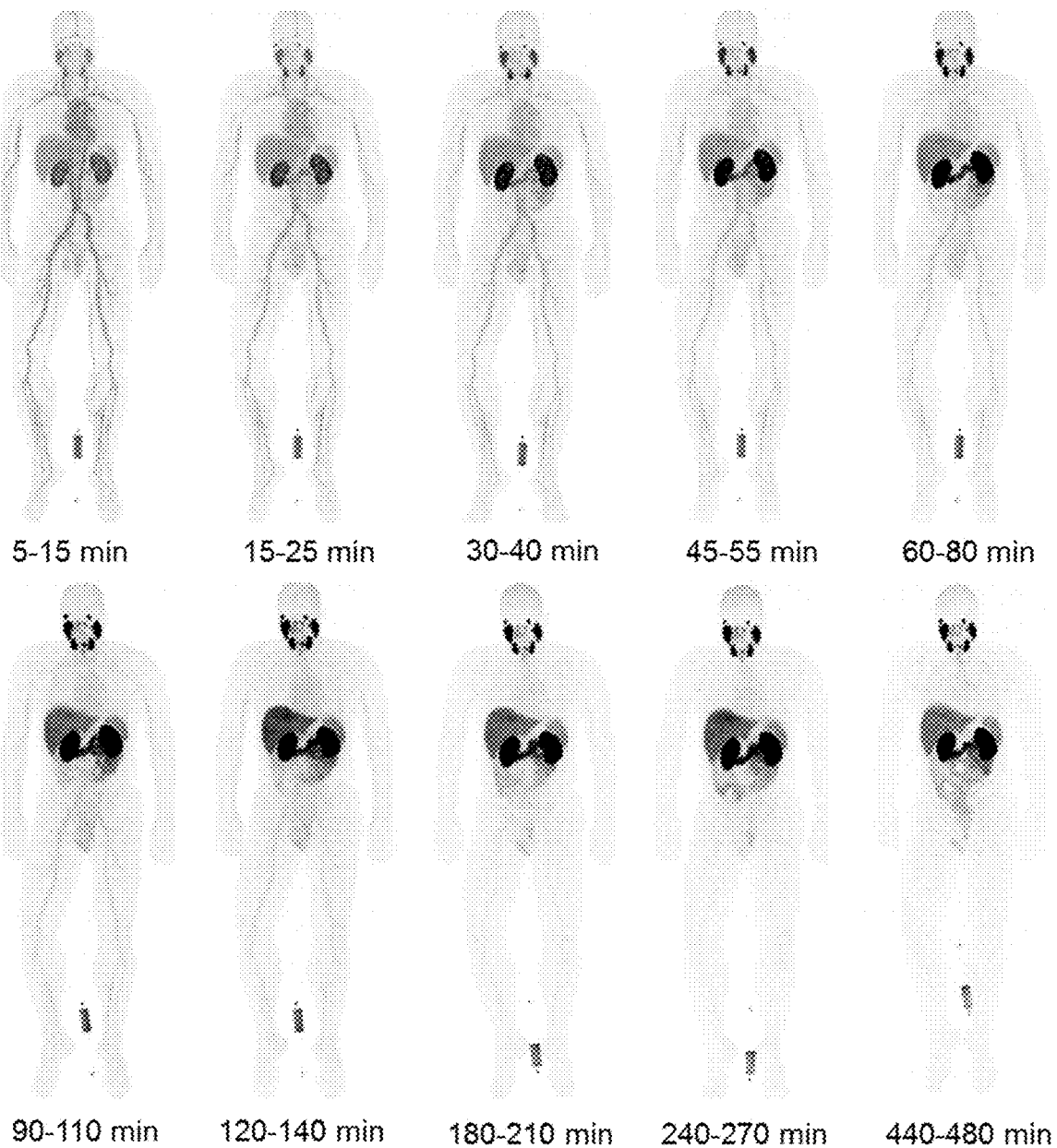
FIG. 14: MIPs of [$^{18}$F]PSMA-1007 in a healthy volunteer

By the application of [$^{18}$F]PSMA-1007 to a healthy volunteer several important insights were gained. First, the effective dose of a PET/CT scan with 200-250 MBq is with 4.3-5.4 mSv (2.15 mSv/MBq; FIG. 14). More than 95% of the blood pool activity is found in the serum (no or negligible infiltration of red blood cells) and more than 90% clearance from the blood pool within the first 3 h after injection. So far, those results are comparable to other important PSMA-tracers. However, in comparison to the other known PSMA-tracers the compounds of the present invention, particularly [$^{18}$F]PSMA-1007, provide a very unique hepatobiliary clearance with very small clearance via the renal pathway. This outstanding low urinary clearance enables an excellent assessment of the prostatic bed. Thus, the tracers according to the present invention are perfectly suited for the primary diagnosis of prostate cancer and local recurrence.

This was further demonstrated by the results of the first-in-man study. Here, excellent tumor-to-background ratios of up to 10 were observed in the primary tumor without any interference from tracer accumulation in the bladder. Further, lymph node metastases with a diameter of down to 1 mm could be detected, which is in the range of the resolution of PET-Scans with F-18. Correlation with the samples gained by pelvic lymphadenectomy analysis revealed a specificity of 95%. Moreover, the samples gained from the prostatectomy were analyzed by histopathology revealing a nearly perfect correlation with the images acquired by PET. Those results clearly demonstrate the feasibility of prostate cancer imaging with the compounds of the present invention, particularly with [$^{18}$F]PSMA-1007.

The below example explains the invention in more detail but are not construed to limit the invention in any way to the exemplified embodiments only.

EXAMPLES

Example 1: Synthesis of Precursors and Cold Reference Compounds of the $^{18}$F-Conjugated Inhibitors The isocyanate of the glutamyl moiety was generated in situ by adding a mixture of 3 mmol of bis(tert-butyl) L-glutamate hydrochloride and 1.5 mL of N-ethyldiisopropylamine (DIPEA) in 200 mL of dry $CH_2C_{12}$ to a solution of 1 mmol triphosgene in 10 mL of dry $CH_2C_{12}$ at 0° C. over 4 h. After agitation of the reaction mixture for 1 h at 25° C., 0.5 mmol of the resin-immobilized (2-chloro-tritylresin) ε-allyloxycarbonyl protected lysine in 4 mL DCM was added and reacted for 16 h with gentle agitation. The resin was filtered off and the allyloxy-protecting group was removed using 30 mg tetrakis(triphenyl)palladium(0) and 400 µL morpholine in 4 mL $CH_2C_{12}$ for 3 hours.

The following coupling of the "linker amino acids" (as defined in Formula I and Scheme 1 as shown above) was performed stepwise using 2 mmol of the Fmoc-protected acid, 1.96 mmol of HBTU and 2 mmol of N-ethyldiisopropylamine in a final volume of 4 mL DMF.

The product was cleaved from the resin in a 2 mL mixture consisting of trifluoroacetic acid, triisopropylsilane, and water (95:2.5:2.5). Purification was performed using RP-HPLC and the purified product was analysed by analytical RP-HPLC and MALDI-MS.

For the preparation of the non-radioactive reference compounds 50 mg of HBTU/DIPEA (0.98 and 1 Eq.) activated 6-Fluoronicotinic-3-acid was coupled in a final volume of 4 ml DMF and agitated for 1 h at room temperature and the product was the cleaved of the resin as described above.

In some preparations a $^{18}$F-tag reactive moieties (e.g. pent-4-ynoic acid or (Boc-aminooxy)acetic acid) were attached to the terminal amino-group for subsequent $^{18}$F labeling.

Example 2: Production and Activation of the [$^{18}$F]Fluoride

Preparation and Activation of the [$^{18}$F]Fluoride

Fluorine-18 was produced by the irradiation of $^{18}$O-enriched water with 16.5 MeV protons using the $^{18}$O(p,n)$^{18}$F nuclear reaction. Irradiations were performed with the Scanditronix MC32NI cyclotron at the department of Radiopharmaceutical Chemistry (E030) at the German Cancer Research Center Heidelberg.

After transfer of the irradiated water to an automated system (Trasis All In One 32) the [$^{18}$F]F$^-$ was separated from the [$^{18}$O]H$_2$O by passing through an previously conditioned (5 ml 1 M K$_2$CO$_3$ and 10 ml water) anion exchange cartridge (Waters Accel™ Plus QMA Cartridge light) and subsequently eluted with a mixture of 800 µl acetonitrile and 150 µl tetrabutylammonium bicarbonate solution (320 mM in water). The mixture was evaporated to dryness an a temperature of 100° C. under a stream of nitrogen. This distillation was subsequently repeated two times by the adding 1.8 ml of acetonitrile for each step. After applying maximum achievable vacuum to the residue for 5 minutes at 100° C. and subsequent cooling to 50° C. the dry residue was dissolved in 2 ml of tert-butanol/acetonitrile (8:2) and used for the labelling reactions.

Alternatively, the system was also used with the classical Kryptofix® 2.2.2/K$_2$CO$_3$ activation system (20 mg 2.2.2+28 µl 1 M K$_2$CO$_3$) in acetonitrile. Further, the solvent for dissolving the activated [$^{18}$F]F$^-$ was changed to dry DMF, DMSO or acetonitrile for some experiments.

Example 3: Radiosynthesis of 6-[$^{18}$F]Fluoronicotinic Acid Tetrafluorophenyl Ester ([$^{18}$F]FN-TFP)

To 10 mg N,N,N-Trimethyl-5-((2,3,5,6-tetrafluorophenoxy)-carbonyl)pyridin-2-aminium trifluoromethanesulfonate (prepared as described by Olberg et al. *J. Med. Chem.*, 2010, 53, 1732) 1 ml of tert-butanol/Acetonitrile (8:2) containing the dried [$^{18}$F]KF-Kryptofix 2.2.2 komplex (0.1-10 GBq $^{18}$F) was added and the mixture was heated at 40° C. After 10 minutes the mixture was diluted with 3 ml of water and the product loaded on a preconditioned Oasis MCX Plus Sep-Pak (Waters). The cartridge was rinsed with 10 mL of water and the purified 6-[$^{18}$F]Fluoronicotinic acid tetrafluorophenyl ester was eluted back to the reaction vessel using 2 mL of water/acetonitrile (7:13). For achieving a higher activity concentration a fractionized elution was done in some cases. Therefore the loaded cartridge was rinsed with 500 µl of solvent, which were discarded, and then eluted with 400-800 µl of solvent for further reactions. Usually more than 50% of the initial activity were eluted with the second fraction.

Example 4: PSMA-1007

The synthesis of the precursor and the cold reference was performed as described under example 1.

Radiosynthesis of [$^{18}$F]PSMA-1007 200 µl of ([$^{18}$F]FN-TFP) were added to 50 µl of a 2 mg/ml solution of PSMA-1007-VL in DMSO. Then 50 µl of buffer (0.2 M phosphate buffer, pH 8.0) were added and the mixture heated at 60° C. for 20 minutes. The products were separated by semi-preparative radio-HPLC and identified by analytical radio-HPLC and comparison of the retention times with the respective non-radioactive reference compounds.

PSMA1007-VL (Precursor):
(Glu)-(Urea)-(Lys)-(2-Nal)-(Bn)-(Glu)-(Glu);
($C_{43}H_{53}N_7O_{15}$; 907.93 g/mol) particularly (Glu)-(Urea)-(Lys)-(2-Nal)-(Bn)-(L-Glu)-(L-Glu)

MS (MALDI): m/z=908.7 [M+H$^+$]$^+$

PSMA-1007

(Glu)-(Urea)-(Lys)-(2-Nal)-(Bn)-(Glu)-(Glu)-FN; $C_{49}H_{55}FN_8O_{16}$; (1031 g/mol) particularly (Glu)-(Urea)-(Lys)-(2-Nal)-(Bn)-(L-Glu)-(L-Glu)-FN;
MS (MALDI): m/z=1032.1 [M+H]$^+$
[$^{18}$F]PSMA-1007
RCA: ca. 6%
HPLC (Gradient: 5% A/95% B-95% A/5% B in 12.5 min; Flow: 3 ml/min; Column: Merck Chromolith® Performance RP-18e 100-4.6 mm; Solvent A: Acetonitrile, Solvent B: 0.1% aqueous TFA): $t_{ret}$: 4.56 min ($t_{dead}$: 0.56 min)

Example 5: PSMA-1011

The synthesis of the precursor and the cold reference was performed as described under example 1. The synthesis [$^{18}$F]PSMA-1011 was performed as described under example 4.
PSMA-1011-VL (precursor):
(Glu)-(Urea)-(Lys)-(2-Naphthylalanine)-(Glu)-(Glu);
$C_{35}H_{46}N_8O_{14}$ (774.78 g/mol)
MS (MALDI): m/z=775.3 [M+H$^+$]$^+$
PSMA-1011:
(Glu)-(Urea)-(Lys)-(2-Naphthylalanine)-(Glu)-(Glu)-FN; $C_{41}H_{48}FN_7O_{15}$ (897.86 g/mol)
MS (MALDI): m/z=898.3 [M+H$^+$]$^+$
[$^{18}$F]PSMA-1011:
RCA: ca. 7%
HPLC (Gradient: 5% A/95% B-50% A/50% B in 10.0 min; Flow: 3 ml/min; Column: Merck Chromolith® Performance RP-18e 100-4.6 mm; Solvent A: Acetonitrile, Solvent B: 0.1% aqueous TFA): $t_{ret}$: 5.72 min ($t_{dead}$: 0.56 min)

Example 6: PSMA-1012

The synthesis of the precursor and the cold reference was performed as described under example 1. The synthesis [$^{18}$F]PSMA-1012 was performed as described under example 4.
PSMA-1012-VL (precursor):
(Glu)-(Urea)-(Lys)-(2-Naphthylalanine)-(γGlu)-(Glu);
$C_{35}H_{46}N_8O_{14}$ (774.78 g/mol)
MS (MALDI): m/z=775.0 [M+H$^+$]$^+$
PSMA-1012:
(Glu)-(Urea)-(Lys)-(2-Naphthylalanine)-(γGlu)-(Glu)-FN; $C_{41}H_{48}FN_7O_{15}$ (897.86 g/mol) MS (MALDI): m/z=897.9 [M+H$^+$]$^+$
[$^{18}$F]PSMA-1012:
RCA: ca. 4%
HPLC (Gradient: 5% A/95% B-50% A/50% B in 10.0 min; Flow: 3 ml/min; Column: Merck Chromolith® Performance RP-18e 100-4.6 mm; Solvent A: Acetonitrile, Solvent B: 0.1% aqueous TFA): $t_{ret}$: 5.61 min ($t_{dead}$: 0.56 min)

Example 7: PSMA-1015

The synthesis of the precursor and the cold reference was performed as described under example 1. The synthesis [$^{18}$F]PSMA-1015 was performed as described under example 4.
PSMA-1015-VL (precursor):
(Glu)-(Urea)-(Lys)-(2-Nal)-(Bn)-(Glu); $C_{38}H_{46}N_6O_{12}$ (778.80 g/mol)
MS (MALDI): m/z=779.4 [M+H$^+$]$^+$
PSMA-1015:
(Glu)-(Urea)-(Lys)-(2-Nal)-(Bn)-(Glu)-FN; $C_{44}H_{48}FN_7O_{13}$ (901.89 g/mol)
MS (MALDI): m/z=902.5 [M+H$^+$]$^+$
[$^{18}$F]PSMA-1015:
RCA: ca. 7%
HPLC (Gradient: 5% A/95% B-50% A/50% B in 10.0 min; Flow: 3 ml/min; Column: Merck Chromolith® Performance RP-18e 100-4.6 mm; Solvent A: Acetonitrile, Solvent B: 0.1% aqueous TFA): $t_{ret}$: 6.48 min ($t_{dead}$: 0.56 min)

Example 8: Synthesis of Dry [$^{18}$F]FN-TFP

The radiosynthesis was performed as described under example 3 until elution of the [$^{18}$F]FN-TFP from the cartridge. After the washing the cartridge with 10 ml water (example 3) the cartridge was blown dry with 20-40 ml air. Then the MCX cartridge was connected to a SepPak SodSulf drying cartridge and the product was eluted with 2 ml of dry acetonitrile. For achieving a higher activity concentration a fractionized elution was done in some cases. Therefore the loaded MCX cartridge was rinsed with 500 µl of solvent (after blowing the cartridge dry), which were discarded, and then the drying cartridge was connected to the MCX cartridge and the product was eluted with 0.8-1.2 ml of acetonitrile for further reactions. Usually more than 50% of the initial activity were eluted with the second fraction.

Example 9: PSMA-1018

The synthesis of the precursor and the cold reference was performed as described under example 1.
Radiosynthesis of [$^{18}$F]PSMA-1018 200 µl of dry [$^{18}$F]FN-TFP (example 8) were added to 50 µl of a 4 mg/ml solution of PSMA-1018-VL in DMSO. Then 10 µl of DIPEA were added and the mixture heated at 60° C. for 20 minutes. Then the reaction mixture was acidified by the addition of 10 µl TFA, the products separated by semi-preparative radio-HPLC and identified by analytical radio-HPLC and comparison of the retention times with the respective non-radioactive reference compounds.
PSMA-1018-VL (precursor):
(Glu)-(Urea)-(Lys)-(2-Nal)-(Bn)-(Glu)-(Glu)-(Glu);
$C_{48}H_{60}N_8O_{18}$ (1037.03 g/mol)
MS (MALDI): m/z=1037.6 [M+H$^+$]$^+$
PSMA-1018:
(Glu)-(Urea)-(Lys)-(2-Nal)-(Bn)-(Glu)-(Glu)-(Glu)-FN; $C_{54}H_{62}FN_9O_{19}$ (1160.12 g/mol)
MS (MALDI): m/z=1160.8 [M+H$^+$]$^+$
[$^{18}$F]PSMA-1018:
RCA: ca. 20%
HPLC (Gradient: 5% A/95% B-95% A/5% B in 10.0 min; Flow: 3 ml/min; Column: Merck Chromolith® Performance RP-18e 100-4.6 mm; Solvent A: Acetonitrile, Solvent B: 0.1% aqueous TFA): $t_{ret}$: 3.87 min ($t_{dead}$: 0.56 min)

Example 10: PSMA-1019

The synthesis of the precursor and the cold reference was performed as described under example 1. The synthesis [$^{18}$F]PSMA-1019 was performed as described under example 9.
PSMA-1019-VL (precursor):
(Glu)-(Urea)-(Lys)-(2-Nal)-(Chx)-(Glu)-(Glu);
$C_{43}H_{59}N_7O_{15}$ (913.97 g/mol)
MS (MALDI): m/z=914.4 [M+H$^+$]$^+$
PSMA-1019:
(Glu)-(Urea)-(Lys)-(2-Nal)-(Chx)-(Glu)-(Glu)-FN; $C_{49}H_{61}FN_8O_{16}$ (1037.05 g/mol)
MS (MALDI): m/z=1037.7 [M+H$^+$]$^+$

[$^{18}$F]PSMA-1019:
RCA: ca. 47%
HPLC (Gradient: 5% A/95% B-95% A/5% B in 12.5 min; Flow: 3 ml/min; Column: Merck Chromolith® Performance RP-18e 100-4.6 mm; Solvent A: Acetonitrile, Solvent B: 0.1% aqueous TFA): $t_{ret}$: 4.43 min ($t_{dead}$: 0.56 min)

Example 11: PSMA-1020

The synthesis of the precursor and the cold reference was performed as described under example 1. The synthesis [$^{18}$F]PSMA-1020 was performed as described under example 9.
PSMA-1020-VL (precursor):
(Glu)-(Urea)-(Lys)-(2-Nal)-(γGlu)-(Glu)-(Glu); $C_{40}H_{53}N_7O_{17}$ (903.89 g/mol)
MS (MALDI): m/z=904.9 [M+H$^+$]$^+$
PSMA-1020:
(Glu)-(Urea)-(Lys)-(2-Nal)-(γGlu)-(Glu)-(Glu)-FN; $C_{46}H_{55}FN_8O_{18}$ (1026.97 g/mol)
MS (MALDI): m/z=1027.9 [M+H$^+$]$^+$
[$^{18}$F]PSMA-1020:
RCA: ca. 60%
HPLC (Gradient: 5% A/95% B-95% A/5% B in 12.5 min; Flow: 3 ml/min; Column: Merck Chromolith® Performance RP-18e 100-4.6 mm; Solvent A: Acetonitrile, Solvent B: 0.1% aqueous TFA): $t_{ret}$: 6.48 min ($t_{dead}$: 0.56 min)

Example 12: PSMA-1022

The synthesis of the precursor and the cold reference was performed as described under example 1. The synthesis [$^{18}$F]PSMA-1022 was performed as described under example 9.
PSMA-1022-VL (precursor):
(Glu)-(Urea)-(Lys)-(2-Nal)-(γGlu)-(γGlu); $C_{35}H_{46}N_8O_{14}$ (774.78 g/mol)
MS (MALDI): m/z=775.4 [M+H$^+$]$^+$
PSMA-1022:
(Glu)-(Urea)-(Lys)-(2-Nal)-(γGlu)-(γGlu)-FN; $C_{41}H_{48}FN_7O_{15}$ (897.86 g/mol)
MS (MALDI): m/z=898.8 [M+H$^+$]$^+$
[$^{18}$F]PSMA-1022:
RCA: ca. 29%
HPLC (Gradient: 5% A/95% B-95% A/5% B in 10.0 min; Flow: 3 ml/min; Column: Merck Chromolith® Performance RP-18e 100-4.6 mm; Solvent A: Acetonitrile, Solvent B: 0.1% aqueous TFA): $t_{ret}$: 3.92 min ($t_{dead}$: 0.56 min)

Example 13: PSMA-1023

The synthesis of the precursor and the cold reference was performed as described under example 1. The synthesis [$^{18}$F]PSMA-1023 was performed as described under example 9
PSMA-1023-VL (precursor):
(Glu)-(Urea)-(Lys)-(2-Nal)-(Bn)-(D-Glu)-(D-Glu); $C_{43}H_{53}N_7O_{15}$ (907.93 g/mol)
MS (MALDI): m/z=907.8 [M+H$^+$]$^+$
PSMA-1023:
(Glu)-(Urea)-(Lys)-(2-Nal)-(Bn)-(D-Glu)-(D-Glu)-FN; $C_{49}H_{55}FN_8O_{16}$ (1031.00 g/mol)
MS (MALDI): m/z=1031.8 [M+H$^+$]$^+$
[$^{18}$F]PSMA-1023:
RCA: ca. 24%
HPLC (Gradient: 5% A/95% B-50% A/50% B in 10.0 min; Flow: 3 ml/min; Column: Merck Chromolith® Performance RP-18e 100-4.6 mm; Solvent A: Acetonitrile, Solvent B: 0.1% aqueous TFA): $t_{ret}$: 3.87 min ($t_{dead}$: 0.56 min)

Example 14: PSMA-1024

The synthesis of the precursor and the cold reference was performed as described under example 1. The synthesis [$^{18}$F]PSMA-1024 was performed as described under example 9.
PSMA-1024-VL (precursor):
(Glu)-(Urea)-(Lys)-(2-Nal)-(Bn)-(D-Glu)-(Glu); $C_{43}H_{53}N_7O_{15}$ (907.93 g/mol)
MS (MALDI): m/z=908.6 [M+H$^+$]$^+$
PSMA-1024:
(Glu)-(Urea)-(Lys)-(2-Nal)-(Bn)-(D-Glu)-(Glu)-FN; $C_{49}H_{55}FN_8O_{16}$ (1031.00 g/mol)
MS (MALDI): m/z=1031.5 [M+H$^+$]$^+$
[$^{18}$F]PSMA-1024:
RCA: ca. 27%
HPLC (Gradient: 5% A/95% B-95% A/5% B in 10.0 min; Flow: 3 ml/min; Column: Merck Chromolith® Performance RP-18e 100-4.6 mm; Solvent A: Acetonitrile, Solvent B: 0.1% aqueous TFA): $t_{ret}$: 3.85 min ($t_{dead}$: 0.56 min)

Example 15: PSMA-1025

The synthesis of the precursor and the cold reference was performed as described under example 1. The synthesis [$^{18}$F]PSMA-1025 was performed as described under example 9.
PSMA-1025-VL (precursor):
(Glu)-(Urea)-(Lys)-(2-Nal)-(Bn)-(Gla); $C_{39}H_{46}N_6O_{14}$ (822.21 g/mol)
MS (MALDI): m/z=822.8 [M+H$^+$]$^+$
PSMA-1025:
(Glu)-(Urea)-(Lys)-(2-Nal)-(Bn)-(Gla)-FN; $C_{49}H_{55}FN_8O_{16}$ (945.32 g/mol)
MS (MALDI): m/z=946.0 [M+H$^+$]$^+$
[$^{18}$F]PSMA-1025:
RCA: ca. 24%
HPLC (Gradient: 5% A/95% B-95% A/5% B in 12.5 min; Flow: 3 ml/min; Column: Merck Chromolith® Performance RP-18e 100-4.6 mm; Solvent A: Acetonitrile, Solvent B: 0.1% aqueous TFA): $t_{ret}$: 4.51 min ($t_{dead}$: 0.56 min)

Example 16: PSMA-1026

The synthesis of the precursor and the cold reference was performed as described under example 1. The synthesis [$^{18}$F]PSMA-1026 was performed as described under example 9.
PSMA-1026-VL (precursor):
(Glu)-(Urea)-(Lys)-(2-Nal)-(Bn)-(Sala); $C_{36}H_{44}N_6O_{13}S$ (800.83 g/mol)
MS (MALDI): m/z=801.8 [M+H$^+$]$^+$
PSMA-1026:
(Glu)-(Urea)-(Lys)-(2-Nal)-(Bn)-(Sala)-FN; $C_{42}H_{46}FN_7O_{14}S$ (923.92 g/mol)
MS (MALDI): m/z=924.7 [M+H$^+$]$^+$
[$^{18}$F]PSMA-1026:
RCA: ca. 57%
HPLC (Gradient: 5% A/95% B-95% A/5% B in 12.5 min; Flow: 3 ml/min; Column: Merck Chromolith® Performance RP-18e 100-4.6 mm; Solvent A: Acetonitrile, Solvent B: 0.1% aqueous TFA): $t_{ret}$: 4.03 min ($t_{dead}$: 0.56 min)

Example 17: PSMA-1027

The synthesis of the precursor and the cold reference was performed as described under example 1. The synthesis [$^{18}$F]PSMA-1027 was performed as described under example 9.

PSMA-1027-VL (precursor):
(Glu)-(Urea)-(Lys)-(2-Nal)-(Bn)-(Sala)-(Sala);
$C_{39}H_{49}N_7O_{17}S_2$ (951.97 g/mol)
MS (MALDI): m/z=952.7 [M+H$^+$]$^+$
PSMA-1027:
(Glu)-(Urea)-(Lys)-(2-Nal)-(Bn)-(Sala)-(Sala)-FN;
$C_{45}H_{51}FN_8O_{18}S_2$ (1075.06 g/mol)
MS (MALDI): m/z=1075.8 [M+H$^+$]$^+$
[$^{18}$F]PSMA-1027:
RCA: ca. 62%
HPLC (Gradient: 5% A/95% B-95% A/5% B in 10.0 min; Flow: 3 ml/min; Column: Merck Chromolith® Performance RP-18e 100-4.6 mm; Solvent A: Acetonitrile, Solvent B: 0.1% aqueous TFA): $t_{ret}$: 3.10 min ($t_{dead}$: 0.56 min)

Example 18: Cell Culture

For binding studies and in vivo experiments LNCaP cells (metastatic lesion of human prostatic adenocarcinoma, ATCC CRL-1740) were cultured in RPMI medium supplemented with 10% fetal calf serum and Glutamax (PAA, Austria). During cell culture, cells were grown at 37° C. in an incubator with humidified air, equilibrated with 5% $CO_2$. The cells were harvested using trypsin-ethylenediaminetetraacetic acid (trypsin-1.5 EDTA; 0.25% trypsin, 0.02% EDTA, all from PAA, Austria) and washed with PBS.

Example 19: Cell Binding and Internalization

The competitive cell binding assay and internalization experiments were performed as described previously (Eder et al. *Bioconjugate Chem.* 2012, 23 (4), 688-697). Briefly, the respective cells (10$^5$ per well) were incubated with the radioligand ($^{68}$Ga-labeled [Glu-urea-Lys(Ahx)]2-HBED-CC (Schafer et al. *EJNMMI Research* 2012, 2:23 doi: 10.1186/2191-219X-2-23))) in the presence of 12 different concentrations of analyte (0-5000 nM, 100 μL/well). After incubation, washing was carried out using a multiscreen vacuum manifold (Millipore, Billerica, Mass.). Cell-bound radioactivity was measured using a gamma counter (Packard Cobra II, GMI, Minnesota, USA). The 50% inhibitory concentration (IC$_{50}$) was calculated by fitting the data using a nonlinear regression algorithm (GraphPad Software). Experiments were performed three times. Reference is made to Table A below.

To determine the specific cell uptake and internalization, 10$^5$ cells were seeded in poly-L-lysine coated 24-well cell culture plates 24 h before incubation. After washing, the cells were incubated with 30 nM of the radiolabeled compounds for 45 min at 37° C. Specific cellular uptake was determined by competitive blocking with 2-(phosphonomethyl)pentanedioic acid (500 μM final concentration, PMPA, Axxora, Loerrach, Germany). Cellular uptake was terminated by washing 3 times with 1 mL of ice-cold PBS. Cells were subsequently incubated twice with 0.5 mL glycine-HCl in PBS (50 mM, pH=2.8) for 5 min to remove the surface-bound fraction. The cells were washed with 1 mL of ice-cold PBS and lysed using 0.3 N NaOH (0.5 mL). The surface-bound and the internalized fractions were measured in a gamma counter. The cell uptake was calculated as percent of the initially added radioactivity bound to 10$^5$ cells [% ID/10$^5$ cells]. The main results are given in Table B.

TABLE A

Binding Affinity Assay

| Compound | IC$_{50}$ [nM] |
|---|---|
| PSMA-1007 | 5 |
| PSMA-1011 | 7 |
| PSMA-1012 | 7 |
| PSMA-1015 | 4 |
| PSMA-1018 | 14 |
| PSMA-1019 | 12 |
| PSMA-1020 | 9 |
| PSMA-1022 | 8 |
| PSMA-1023 | 8 |
| PSMA-1024 | 8 |
| PSMA-1025 | 9 |
| PSMA-1026 | 14 |
| PSMA-1027 | 7 |

TABLE B

Specific Internalization

| Compound | Cell surface [% ID/10$^5$ cells] | Internalised [% ID/10$^5$ cells] | Internalized fraction [%]* |
|---|---|---|---|
| PSMA-1007 | 2.7 | 6.5 | 71 |
| PSMA-1011 | 4.1 | 0.7 | 15 |
| PSMA-1012 | 6.9 | 2.7 | 28 |
| PSMA-1015 | 14.3 | 6.0 | 30 |
| PSMA-1018 | 1.1 | 0.9 | 45 |
| PSMA-1019 | 5.5 | 1.9 | 26 |
| PSMA-1020 | 6.8 | 1.5 | 18 |
| PSMA-1022 | 3.5 | 1.0 | 22 |
| PSMA-1023 | 6.5 | 3.2 | 33 |
| PSMA-1024 | 5.3 | 2.1 | 28 |
| PSMA-1025 | 4.3 | 3.1 | 42 |
| PSMA-1026 | 1.3 | 1.3 | 50 |
| PSMA-1027 | 0.9 | 1.4 | 60 |

*(Internalized activity/total activity)*100

Example 20: MicroPET

For the microPET studies, 10-25 MBq of the radiolabeled compounds in a volume of 0.10 ml (60 pmol) were injected via a lateral tail vein into mice bearing LNCaP tumor xenografts. The anesthetized animals (2% sevoflurane, Abbott, Wiesbaden, Germany) were placed in prone position into the Inveon small animal PET scanner (Siemens, Knoxville, Tenn., USA) to perform dynamic microPET scans. The results are shown in FIGS. 10 and 11.

Example 21: Plasma Binding and Stability

For the determination of the plasma binding 3 μl of 6 μmolar c.a. [$^{18}$F]PSMA solution was added to 300 μl human serum AB and incubated at 37° C. for 1 h. Subsequently the product mixture was analyzed by size-exclusion chromatography.

No plasma binding was observed with any of the compounds.

For the determination of the plasma stability 50 μl of 6 μmolar c.a. [$^{18}$F]PSMA solution was added to 450 μl human serum AB and incubated at 37° C. At 1, 2 and 4 h samples were prepared. Therefore 100 μl of the tracer/plasma mixture were added to 100 μl of acetonitrile. Subsequently the mixture was centrifuged at 13000 rpm for 3 minutes. 100 μl of the supernatant were added to 100 μl of acetonitrile, centrifuged at 13000 rpm for 5 minutes, the liquid separated from any residual solids and analyzed by HPLC.

All of the compounds were stable in human plasma at 37° C. for at least 4 hours.

Example 22: In Vivo Experiments

For in vivo experiments, 8 week old BALB/c nu/nu mice were subcutaneously inoculated into the right trunk with $5 \times 10^6$ LNCaP- or PC3-cells in 50% Matrigel. When the size of tumor was approximately 1 $cm^3$, the radiolabeled compound was injected via the tail vein (ca. 30 MBq, 60 pmol for μPET imaging; ca. 1 MBq, 60 pmol for organ distribution).

Organ Distribution

The F-18 labeled compounds were injected via tail vein (1-2 MBq per mouse; 60 pmol). At 1 h after injection, the animals were sacrificed. Organs of interest were dissected, blotted dry, and weighed. The radioactivity was measured with a gamma counter (Packard Cobra II, GMI, Minnesota, USA) and calculated as % ID/g. The main results are given in FIGS. 8 and 9.

Figure 13:
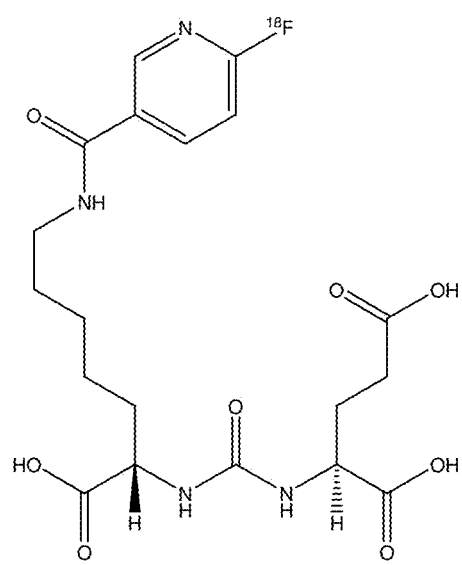
FIG. 13: Structure of PSMA-1009

The compounds PSMA 1003 and PSMA 1009 are for comparison and are shown in FIGS. 12 and 13.

Example 23: [$^{18}$F]PSMA-1007 for Human Application

[$^{18}$F]PSMA-1007 was produced by conjugation of dry [$^{18}$F]FN-TFP (Example 8) to PSMA1007-VL (Example 4) under dry conditions (analogously Example 9) on an automated synthesis module (Trasis AllInOne) and purified by semi-preparative HPLC. Radio-HPLC was performed to determine the chemical identity and the chemical and radiochemical purity of [$^{18}$F]PSMA-1007. Residual solvents were determined by gas chromatography. The radionuclide purity was controlled by half-life measurement. The product solution was tested for sterility, bacterial endotoxins (LAL-test), pH, colorlessness and particles. The integrity of the sterile filter after filtration was examined using the bubble-point test.

Example 24: Application of [$^{18}$F]PSMA-1007 to a Healthy Volunteer

The healthy subject was injected a total activity of 300 MBq and subsequently PET scans were performed on a Biograph mCT Flow scanner (Siemens, Erlangen, Germany) in three blocks. Block 1 contained PET-1 (start 5 min p.i.) to PET-7 (ending 140 min p.i.), block 2 contained PET-8 (start 180 min p.i.) and PET-9 (240-270 min p.i.), block 3 contained PET-10 (440-480 min p.i.). A non-enhanced low-dose CT (estimate 1.43 mSv, respectively) for attenuation correction was performed at the beginning of each block, followed by serial emission scans without moving the volunteer in between.

Kidneys, liver, spleen, whole heart, upper and lower large intestine, parotid glands, submandibular glands and urinary bladder were segmented into volumes of interest (VOIs) using a percentage of maximum threshold between 20% and 30% using the corresponding CT as guidance and then time activity curves (TACs) were calculated for all organs. The TAC for red marrow was derived from the venous blood samples and then the dose for the red marrow calculated (S. Shen et al., *JNM* 2002, 43, 1245-1253; G. Sgouros et al., *JNM* 1993, 34, 689-694.). The TAC for the urinary bladder content was a combination of estimated activity in the urinary bladder VOI in PET and activity measured in the voided urine. Curve fitting was applied to all TACs. Kidneys, salivary glands, upper and lower large intestine and heart were fitted with a bi-exponential function. For liver, spleen and urinary bladder content a mono-exponential fit to the last three time points was performed.

Figure 15:
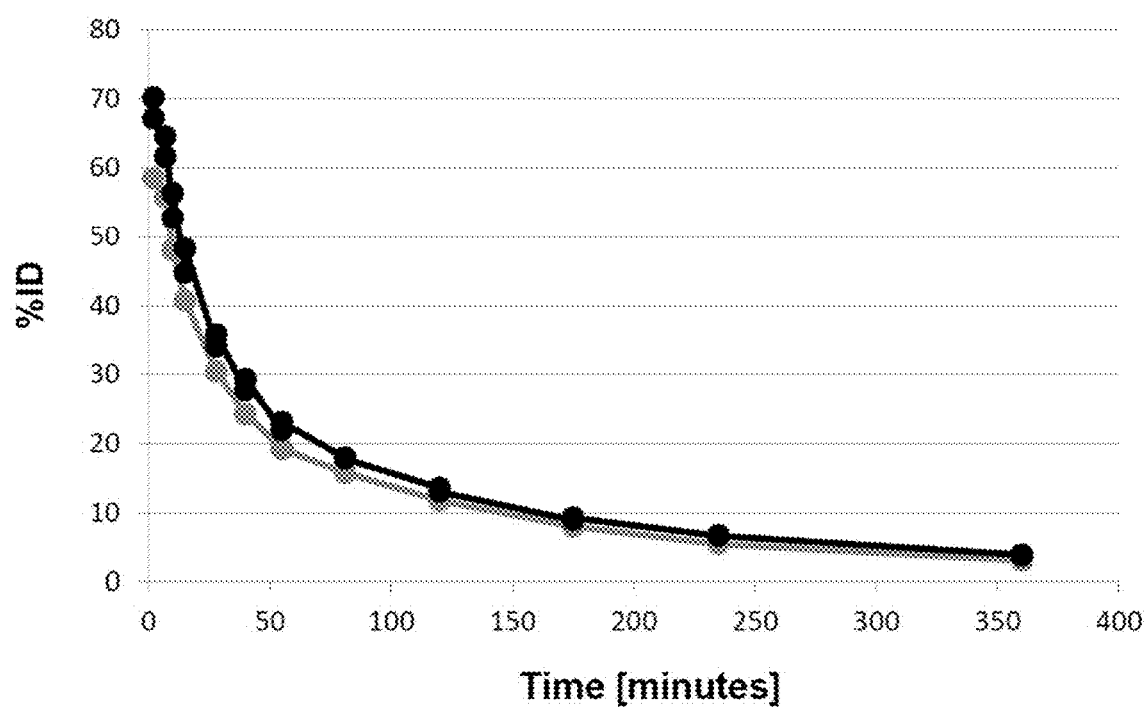
FIG. 15: Blood (black) and serum (gray) time-activity-curves expressed as percent injected dose in a healthy volunteer
Figure 16:
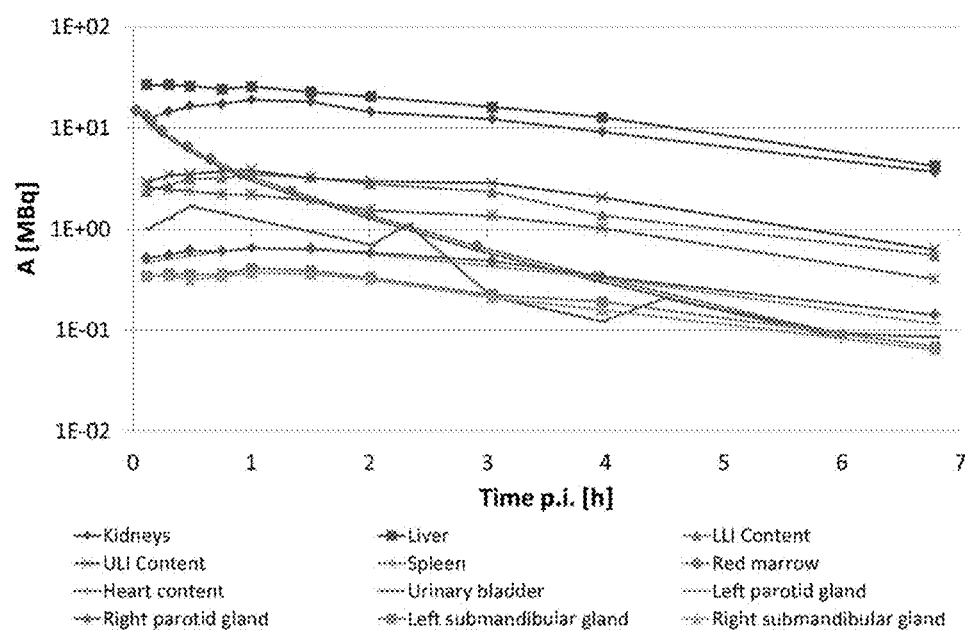
FIG. 16: Time-activity-curves of normal organs with PET-delineable volume-of-interest in a healthy volunteer

Absorbed and effective dose calculations were performed using the ICRP endorsed IDAC 1.0 package which is integrated in QDOSE. Additionally, residence times of all included source organs and remainder body were exported as an OLINDA case file for dose calculation (OLINDA 1.1). The absorbed doses to the salivary glands (parotid and submandibular glands) were determined using the spherical model. The organ masses for the salivary glands were estimated with 25 g for a parotid and 12.5 g for a submandibular gland (ICRP publication 89). The results are summarized in FIGS. 14-16.

Figure 17:
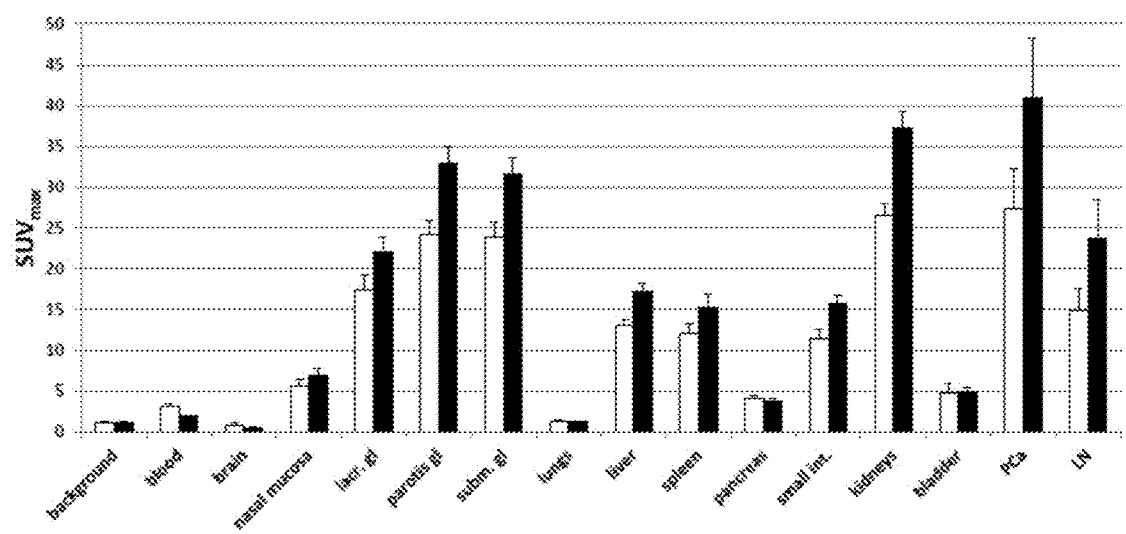
FIG. 17: Organ distribution [$^{18}$F]PSMA-1007 in ten patients suffering from prostate cancer expressed as SUV$_{max}$
Figure 18:
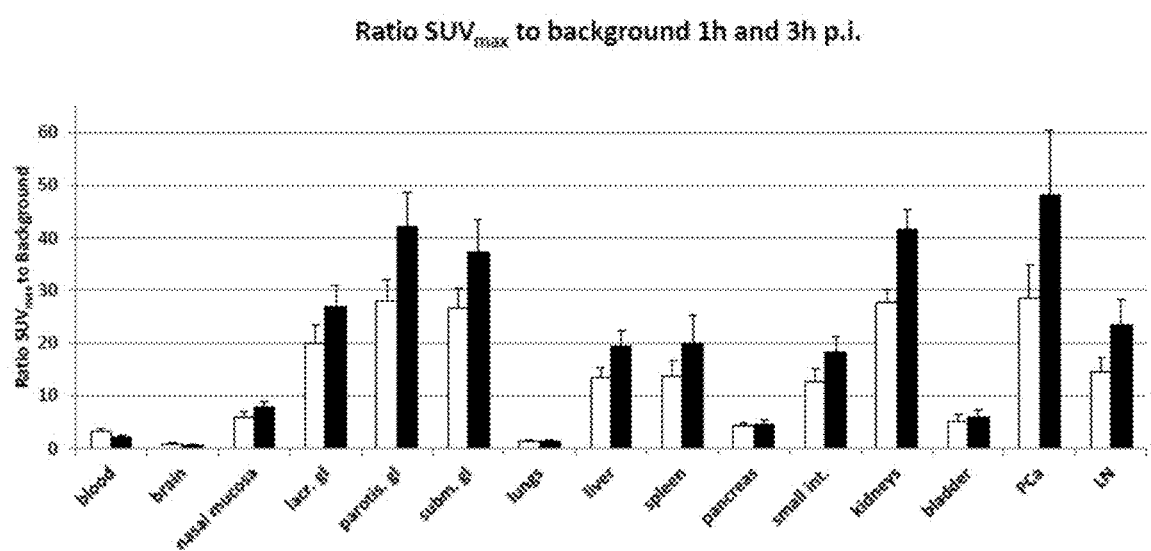
FIG. 18: Tumor-to-Background ratios of [$^{18}$F]PSMA-1007 in ten patients suffering from prostate cancer calculated from the respective SUV$_{max}$ values
Figure 19:
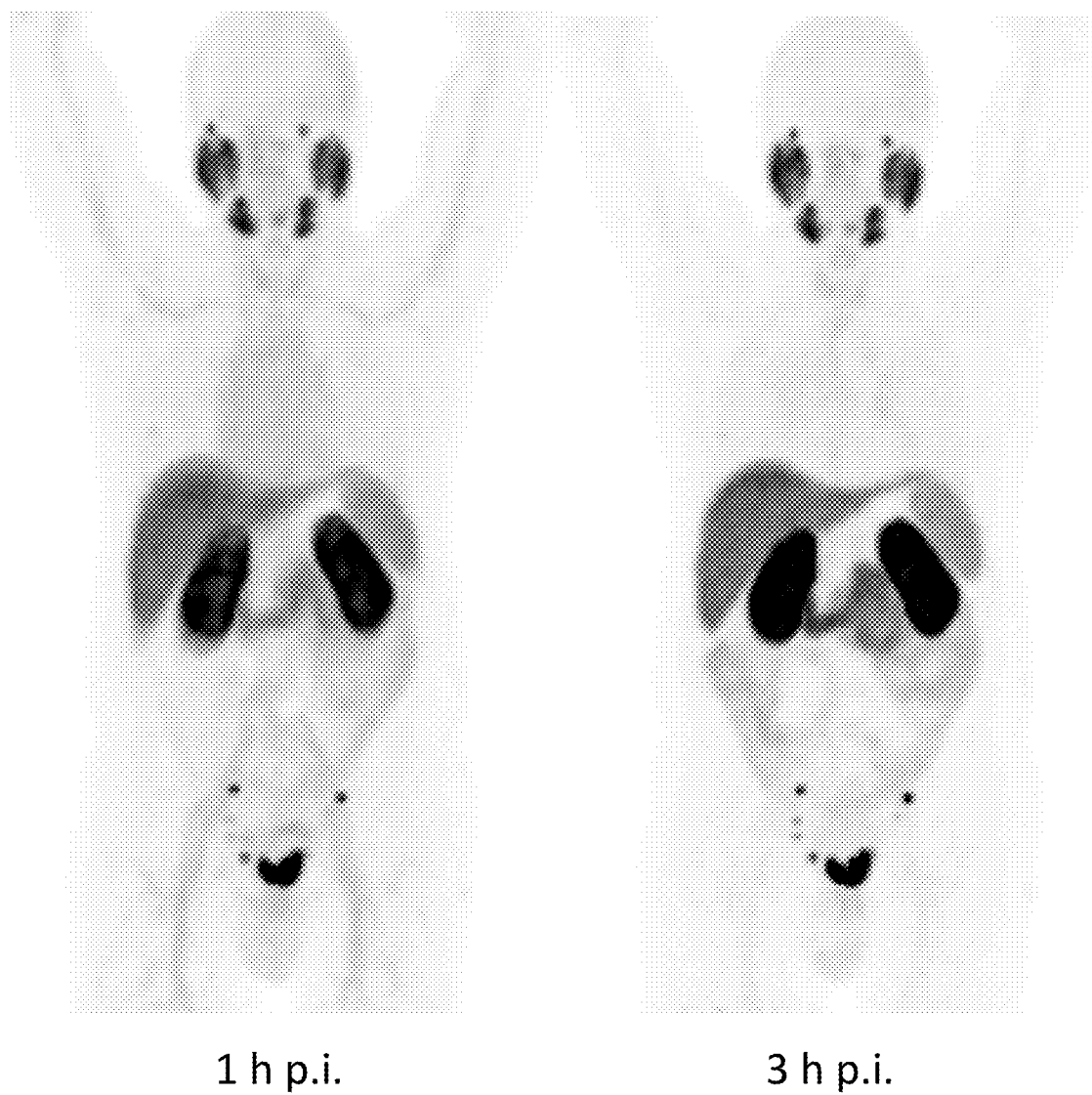
FIG. 19: MIP of a 77-year old prostate cancer patient (PSA 40 ng/ml) scanned with [$^{18}$F]PSMA-1007 1 and 3 h p.i. showing a large tumor mass on the mid and apex area of prostate and several lymph node metastases. Outside of the pelvic region there was no metastasis found
Figure 20:
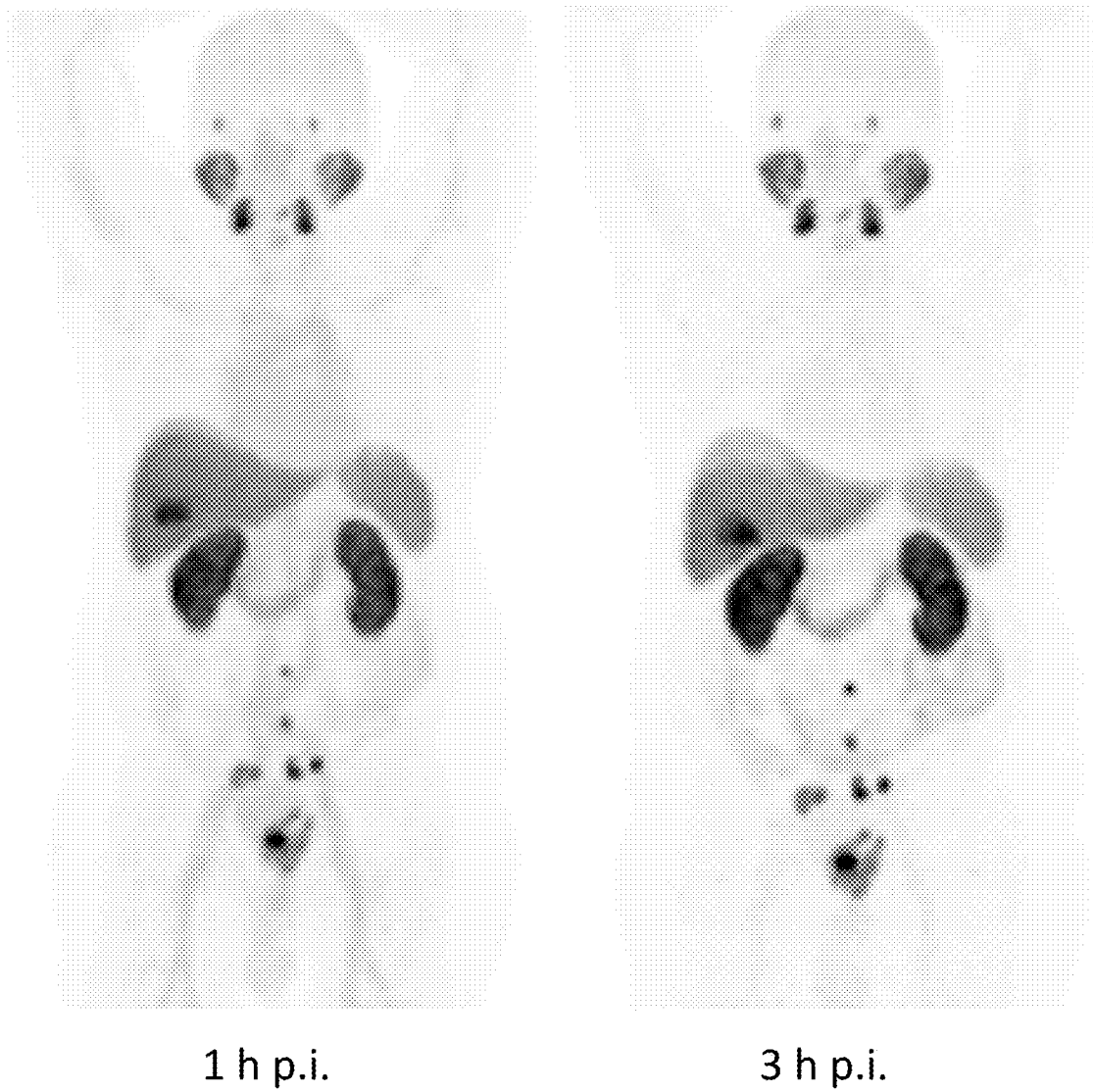
FIG. 20: MIP of a 72-year old patient (PSA 15 ng/ml) diagnosed with Gleason 9 (5+4) prostate cancer scanned with [$^{18}$F]PSMA-1007 1 and 3 h p.i. Patient presents a large tumor mass in the whole prostate gland with infiltration in the left seminal vesicles and several lymph nodes in the pelvic region. Two metastatic lymph nodes are located outside the pelvic region, both paraaortic at level L3/4 and L5.

Example 25: Application of [$^{18}$F]-PSMA-1007 in a Patients Suffering from Prostate Cancer Ten patients (age 60-80 years) suffering from a newly diagnosed high-risk prostate cancer with a gleason score of 7-9 and initial PSA levels of 5-90 ng/ml were injected 100-360 MBq [$^{18}$F]-PSMA-1007 and subsequently PET scans were performed on a Biograph mCT Flow scanner (Siemens, Erlangen, Germany) at 1 and 3 h p.i. The results are depicted in FIGS. 17 and 18 as mean values of the $SUV_{mean}$ and $SUV_{max}$, respectively. The pictures gained with the PET scans are exemplified in FIGS. 19 and 20 as maximum intensity projections.

Figure 21:
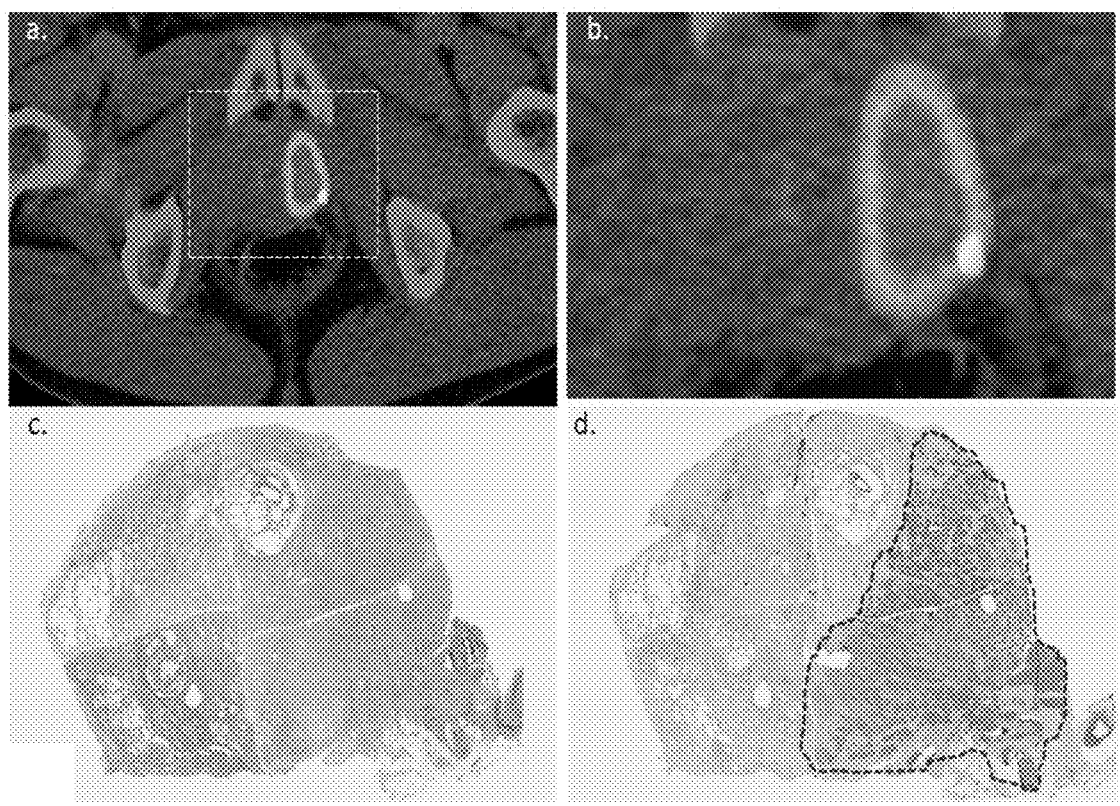
FIG. 21: Transaxial PET/CT-scan of a patient (a,b) and corresponding histopathology of the subsequent prostatectomy specimen; H&E staining (c); PSMA-immunostaining with outlined tumor contours circumscribed by the broken line (d).

Eight of the patients underwent radical prostatectomy with extended pelvic lymphadenectomy. Analyses of prostatectomy specimen were performed blinded to PET-data under the supervision of dedicated uropathologists, according to International Society of Urological Pathology standards (T. H. van der Kwast et al. *Mod. Phathol.* 2011, 24, 16-25). Representative sections were stained by immunohistochemistry. The sections were deparaffinized in xylene and rehydrated in a graded ethanol series. Antigen retrieval was performed with a steam cooker using retrieval buffer (Target Retrieval Solution, Dako). A mouse monoclonal antibody against PSMA (clone 3E6, Dako) was used at a 1:100 dilution and incubated overnight at 4° C. ad subsequently immunodetection was performed using the Histostain-Plus detection kit (Invitrogen). Stained sections were scanned using a Nanozoomer 2.0-HT Scansystem (Hamamatsu Photonics) to generate digital whole slide images. The staining revealed a nearly perfect correlation with the PET scan, as exemplified in FIG. 21.

The invention claimed is:

1. A compound of Formula I:

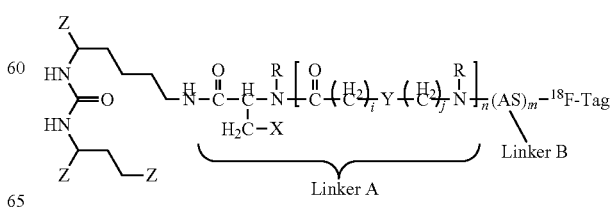

Formula I with:
| | |
|---|---|
| i, j | 0, 1 |
| m | 1-5 |
| n | 0-3 |
| R | H, CH$_3$ |
| AS | Natural or non-natural amino acid |
| Z: | —CO$_2$H, —SO$_2$H, —SO$_3$H, —SO$_4$H, —PO$_2$H, —PO$_3$H, —PO$_4$H$_2$ |
| X: | Naphthyl, Phenyl, Biphenyl, Indolyl (=2,3-benzopyrrolyl), Benzothiazolyl, Quinoyl |
| Y: | Aryl, Alkylaryl, Cyclopentyl, Cyclohexyl, Cycloheptyl, N-Piperidyl and N-methylated Piperidyl salt |
$^{18}$F-Tag:
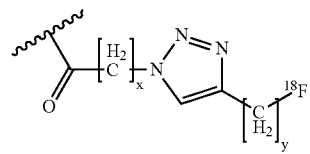
x = 1-5
y = 1-5
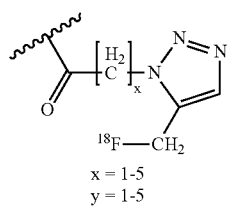
x = 1-5
y = 1-5
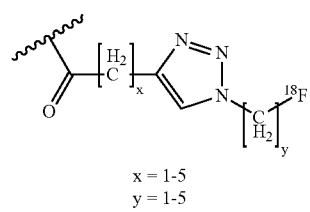
x = 1-5
y = 1-5
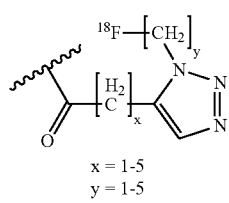
x = 1-5
y = 1-5
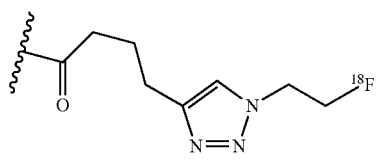 [SMILES: *C(=O)CCCc1cn(CC[18F])nn1]
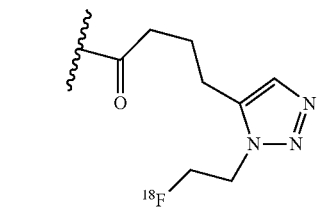 [SMILES: *C(=O)CCCc1cnnn1CC[18F]]
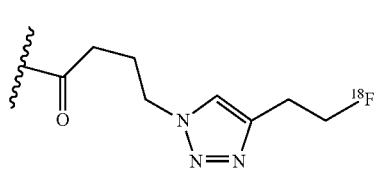 [SMILES: *C(=O)CCCn1cc(CC[18F])nn1]
-continued
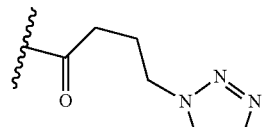
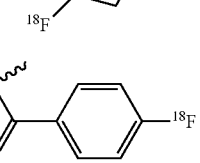
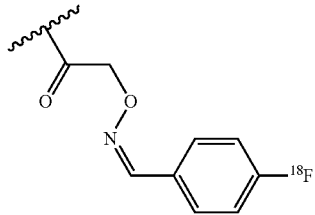 [SMILES: *C(=O)CO/N=C\c1ccc([18F])cc1]
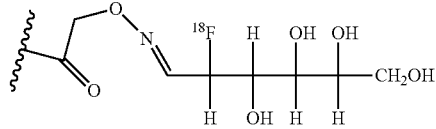 [SMILES: *C(=O)CO/N=C/C([18F])C(O)C(O)C(O)CO]
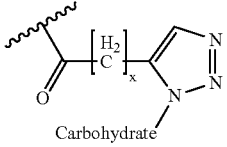
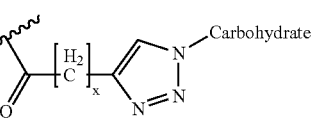
With:
x = 1-5
Carboydrate:
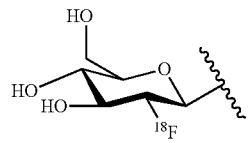
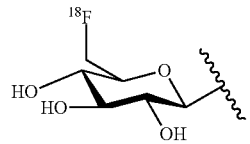
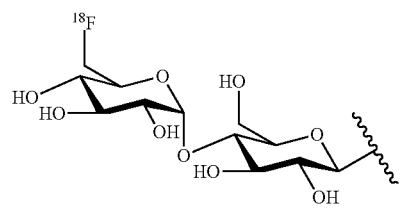

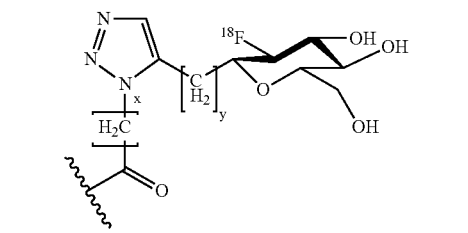

x = 1-5
y = 1-5

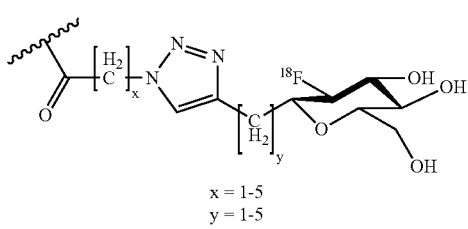

x = 1-5
y = 1-5

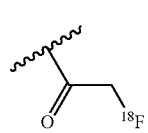 [SMILES: *C(=O)C[18F]]

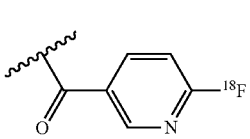 [SMILES: *C(=O)c1ccc([18F])nc1]

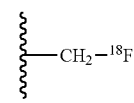

x = 1-10

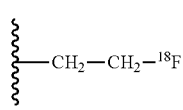

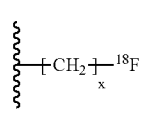

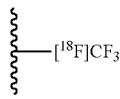

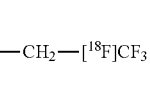

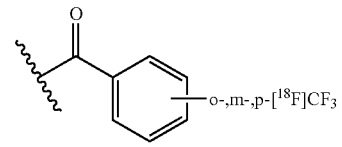

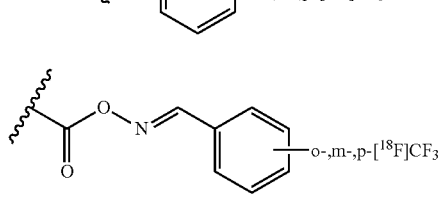

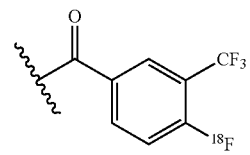 [SMILES: *C(=O)c1ccc([18F])c(C(F)(F)F)c1]

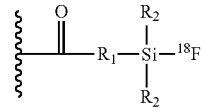

$R_1$: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
$R_2$: Any alkyl or aryl group
especially methyl isopropyl, tert-butyl,
phenyl or 1-naphtyl

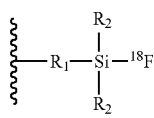

$R_1$: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
$R_2$: Any alkyl or aryl group
especially methyl isopropyl, tert-butyl,
phenyl or 1-naphtyl

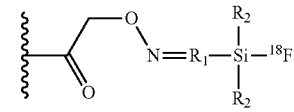

$R_1$: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
$R_2$: Any alkyl or aryl group
especially methyl isopropyl, tert-butyl,
phenyl or 1-naphtyl -continued

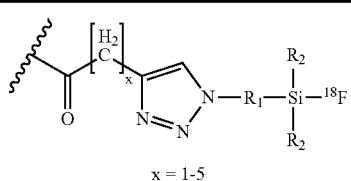

x = 1-5

R₁: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R₂: Any alkyl or aryl group
especially methyl isopropyl, tert-butyl,
phenyl or 1-naphtyl

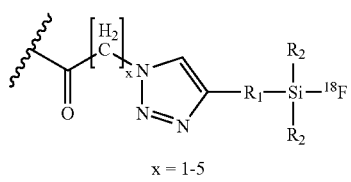

x = 1-5

R₁: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R₂: Any alkyl or aryl group
especially methyl isopropyl, tert-butyl,
phenyl or 1-naphtyl

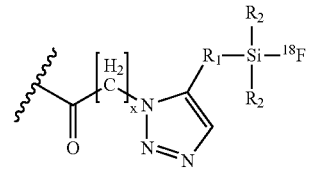

x = 1-5

R₁: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R₂: Any alkyl or aryl group
especially methyl isopropyl, tert-butyl,
phenyl or 1-naphtyl

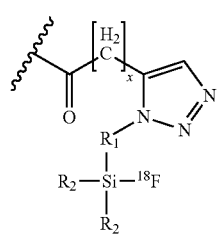

R₁: Any alkyl, aryl or arylalkyl linker
especially methyl, 2-ethyl, 3-propyl,
2-,3-,4-phenyl, 2-,3-,4-phenylmethyl, 2-,3-,4-phenylpropyl
R₂: Any alkyl or aryl group
especially methyl isopropyl, tert-butyl,
phenyl or 1-naphtyl.

2. The compound of claim 1, wherein the non-natural amino acid has the formula

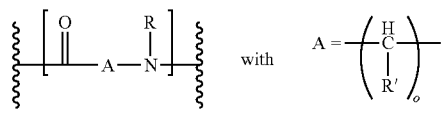

and R'=H, $CO_2H$, $CH_2CO_2H$, $C_2H_4CO_2H$, $CH(CO_2H)_2$, $CH(CH_2CO_2H)_2$, $CH(CO_2H)(CH_2CO_2H)$, $CH_2CH(CO_2H)_2$, $SO_3H$;

o=1-3; R=H, $CH_3$.

3. A pharmaceutical composition comprising the compound of claim 1, or a pharmaceutically acceptable salt or ester thereof, and a pharmaceutically acceptable carrier.

4. The compound of claim 1 having the structure;

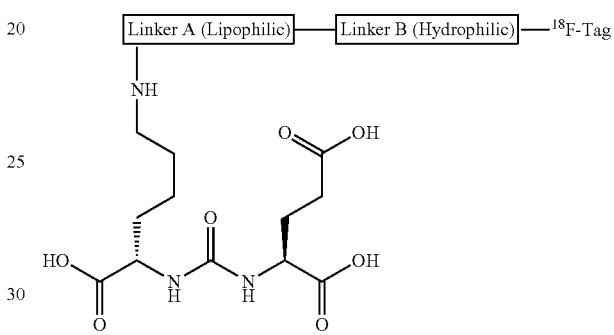

wherein the linker A is selected from the group consisting of:

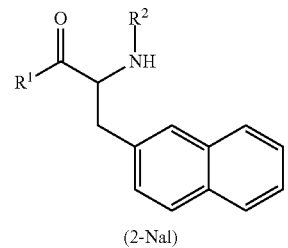

(2-Nal)

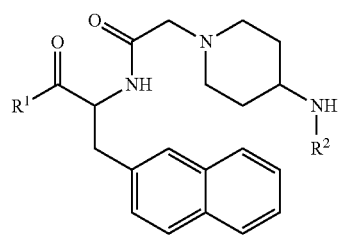

(2-Nal)-(AcAP)

-continued
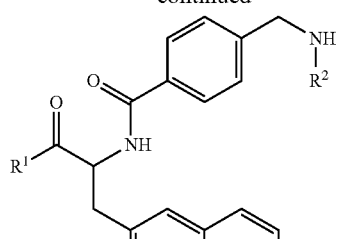
(2-Nal)-(Bn)
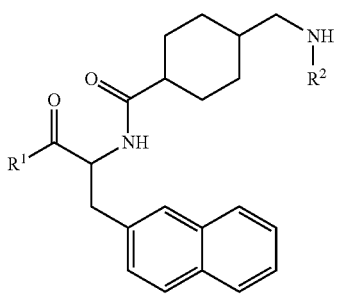
(2-Nal)-(Chx)
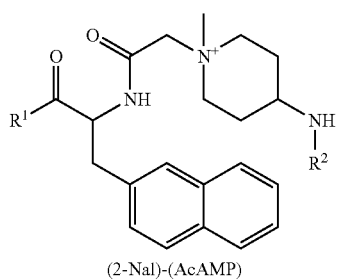
(2-Nal)-(AcAMP)
(In form of any pharmaceutically acceptable salt)
wherein $R^1$=(Glu)-(Urea)-(Lys) and $R^2$=(Linker B)$_m$-$^{18}$F Tag, m=1-5,
and linker B is selected from the group consisting of:
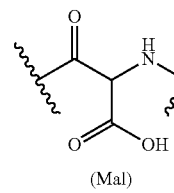
(Mal)
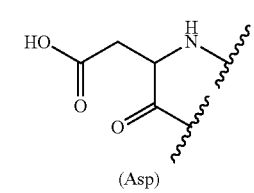
(Asp)
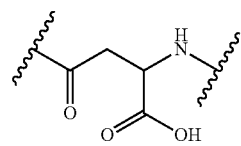
(βAsp)
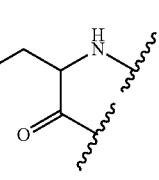
(Glu)
-continued
(γGlu)
(Lym)
(βLym)
(Tri)
(βTri)
(γTri)
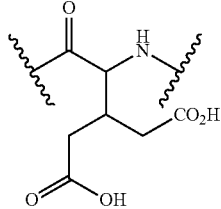
(Gla)
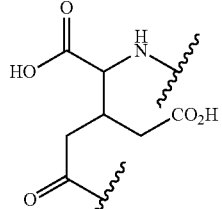
(γGla)
(Glo)
(γGlo)
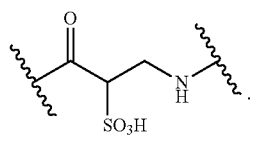
(Sala)

5. The compound of claim 1, selected from the following
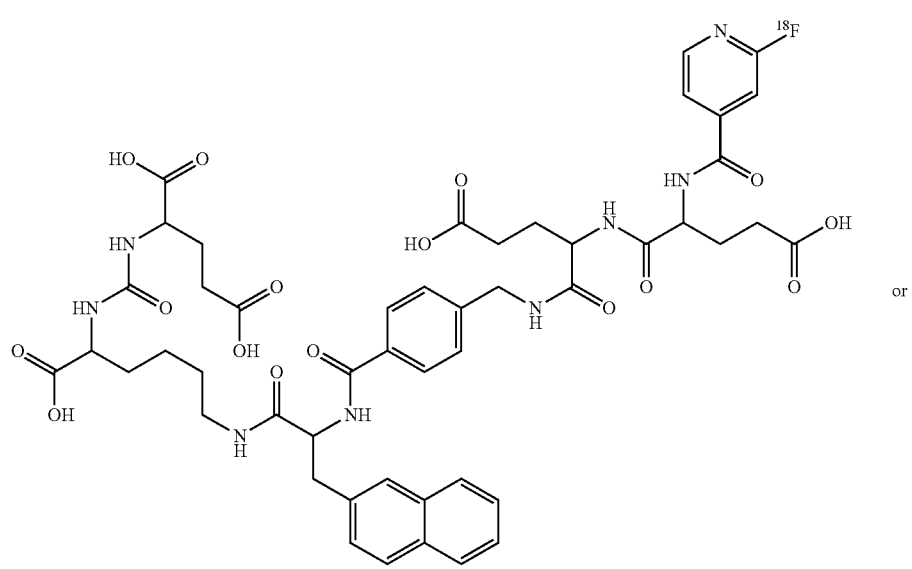
Number: 1a
or
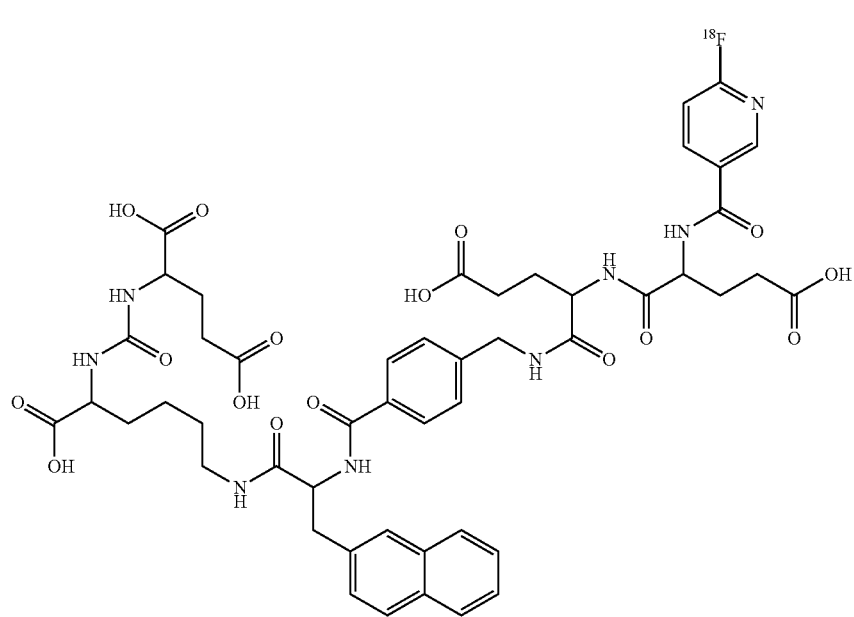
Number: 1

Number: 2a
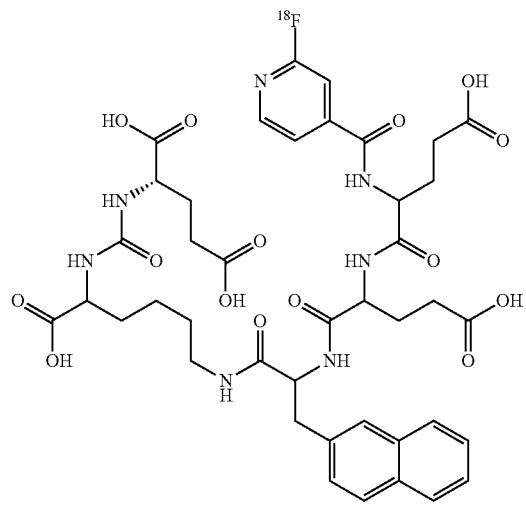
Number: 2
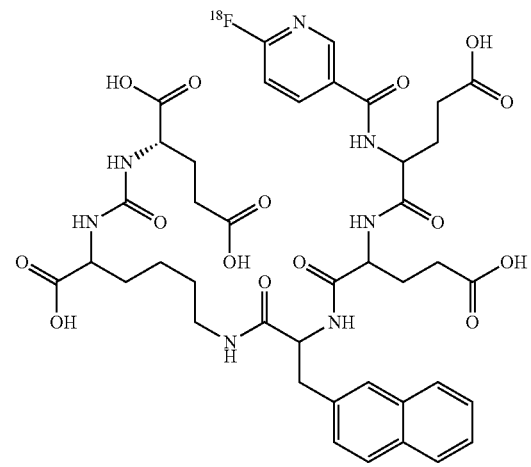
or
Number: 3a
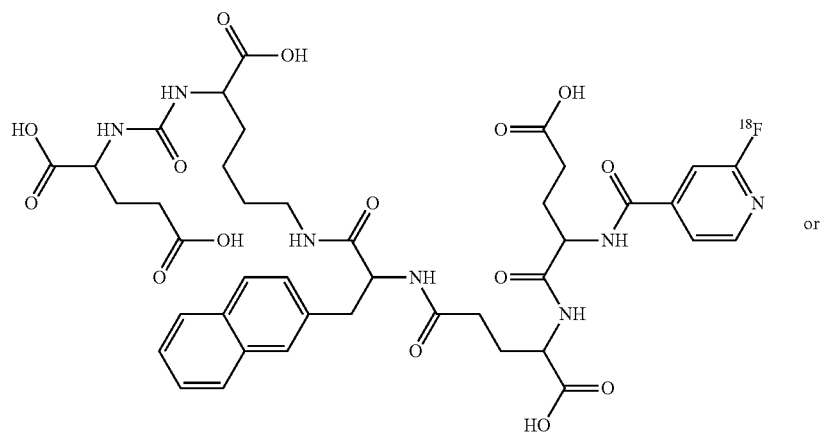
or
Number: 3
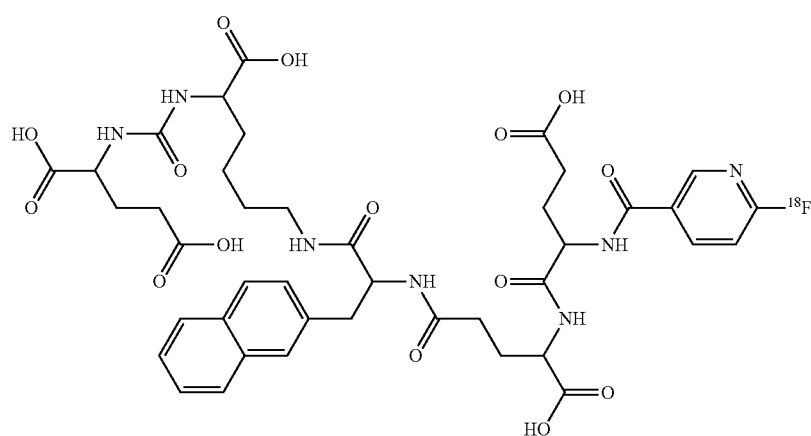

Number: 4
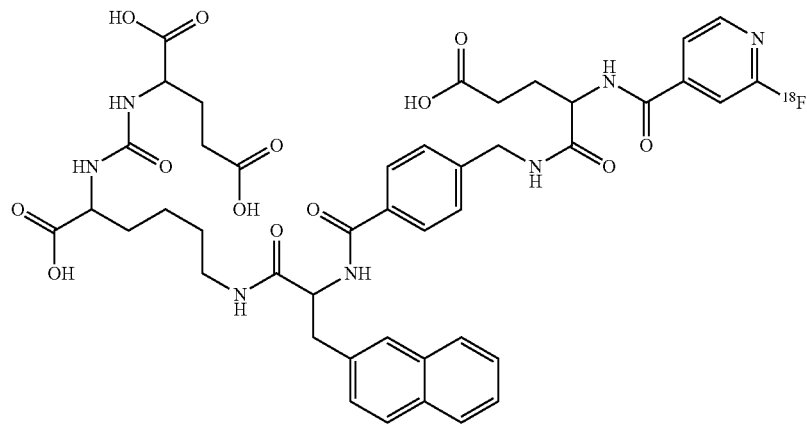
or
Number: 4a
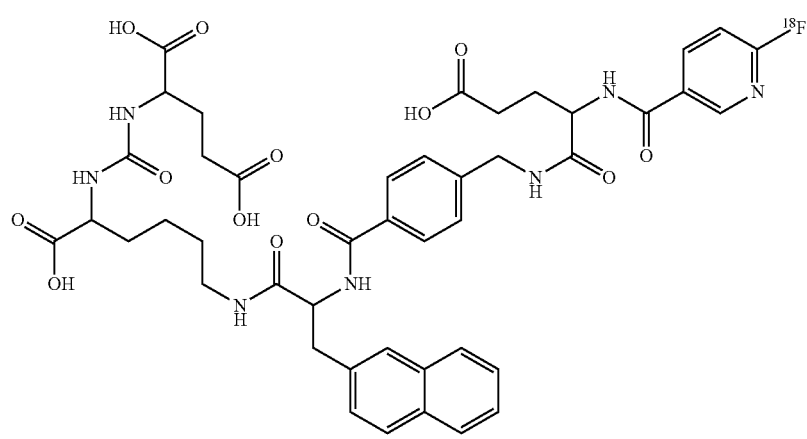
Number: 5a
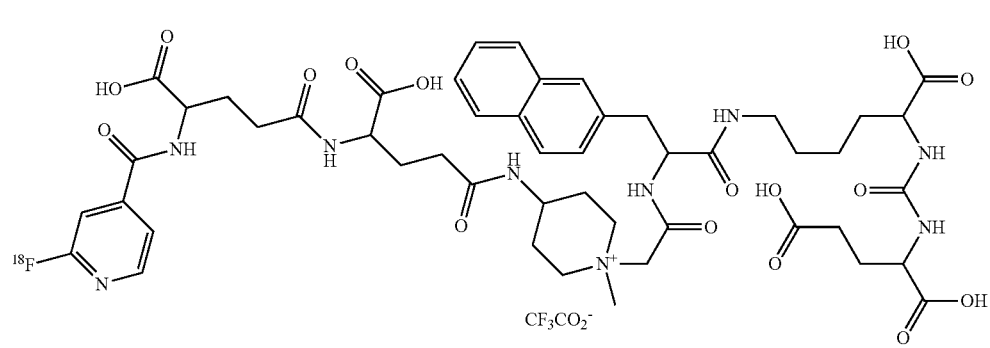
or
Number: 5
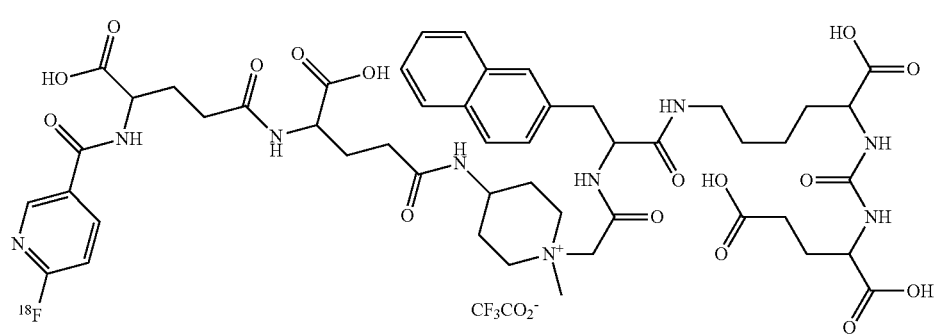

-continued
Number: 6a
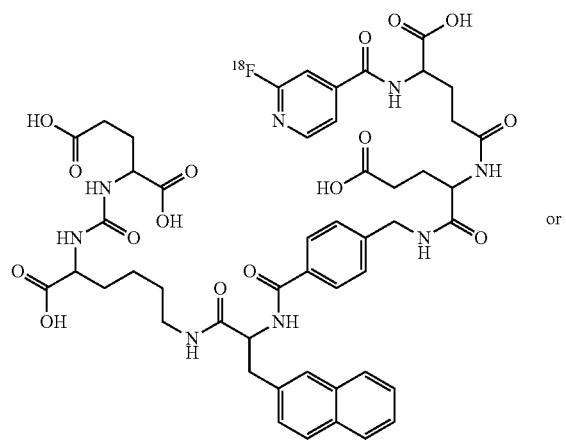
Number: 6
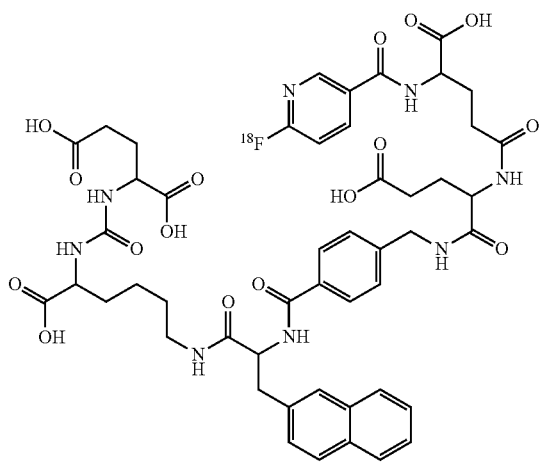
or
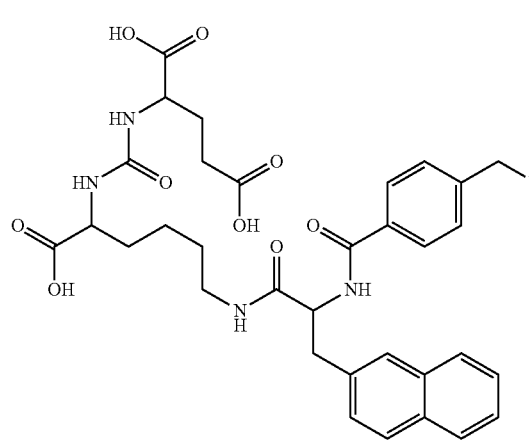
Number: 7a
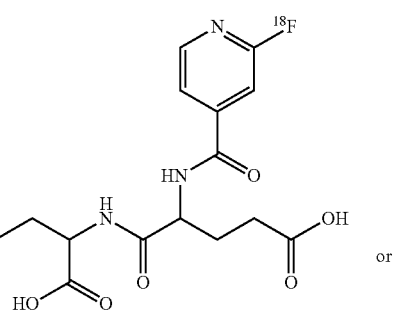
or
Number: 7
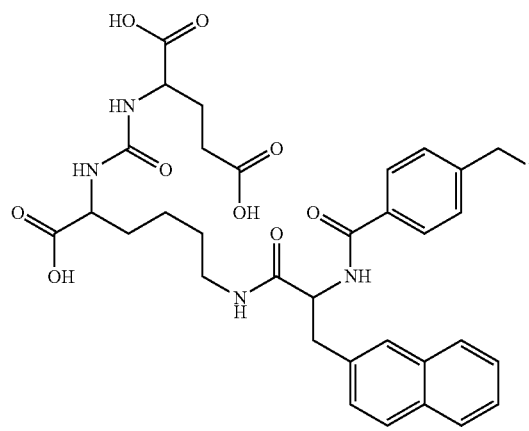
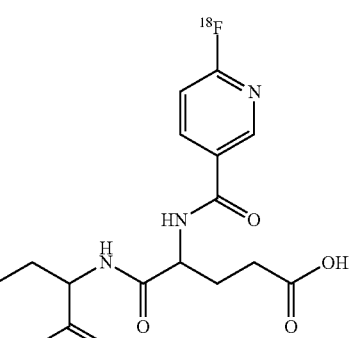

-continued
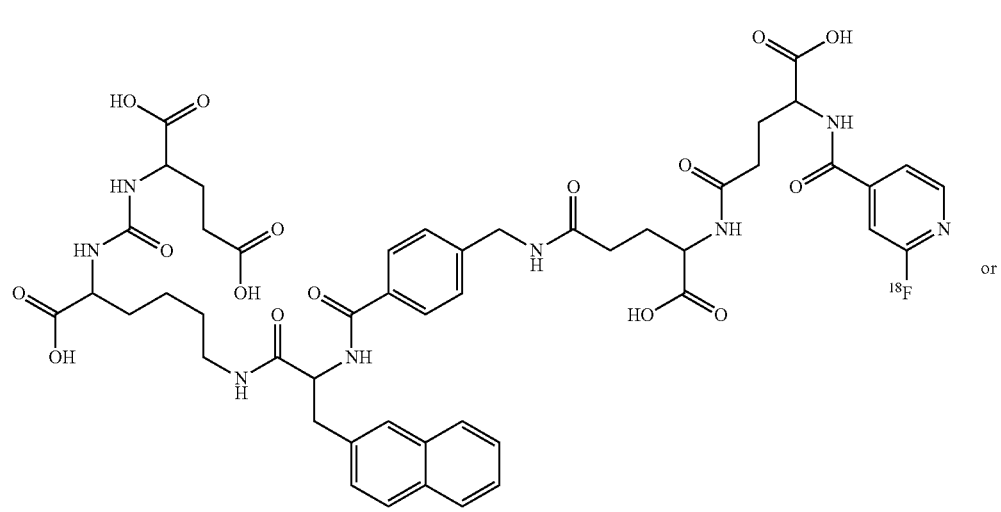
Number: 8a
or
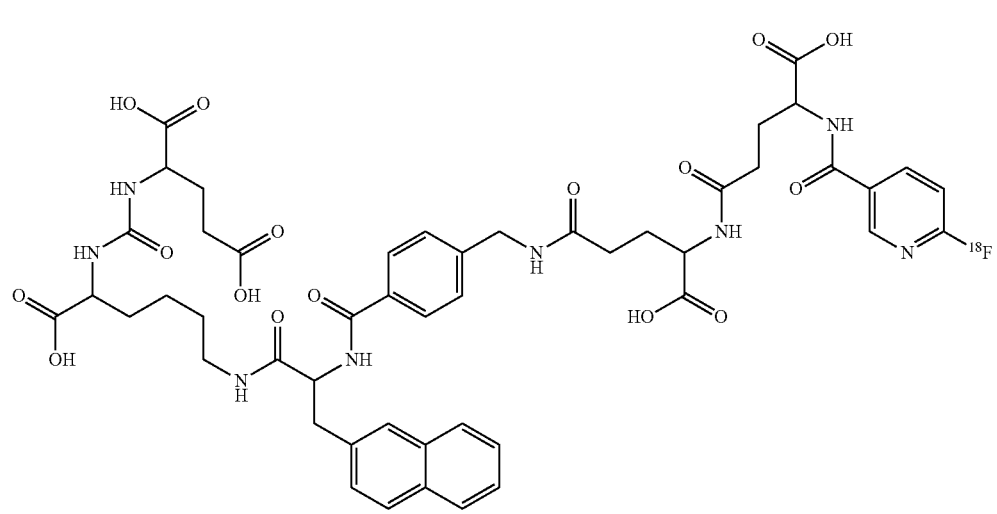
Number: 8
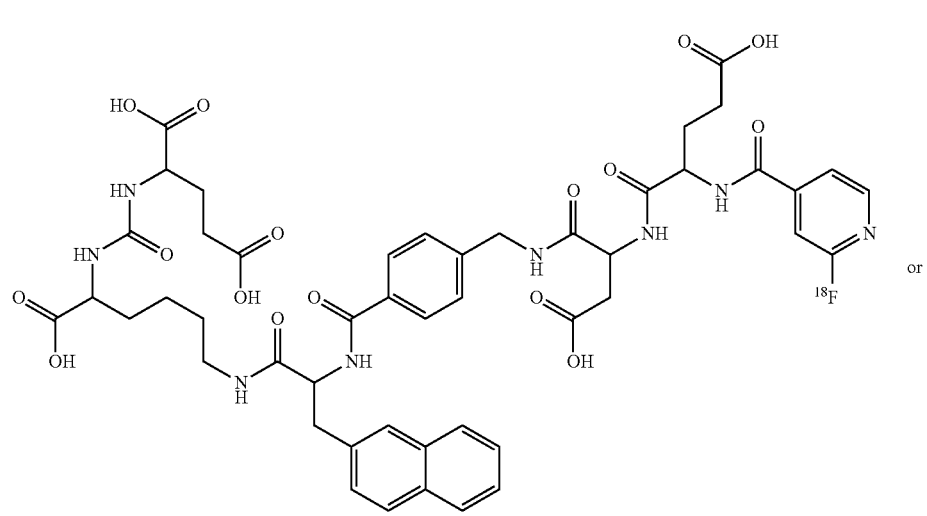
Number: 9a
or

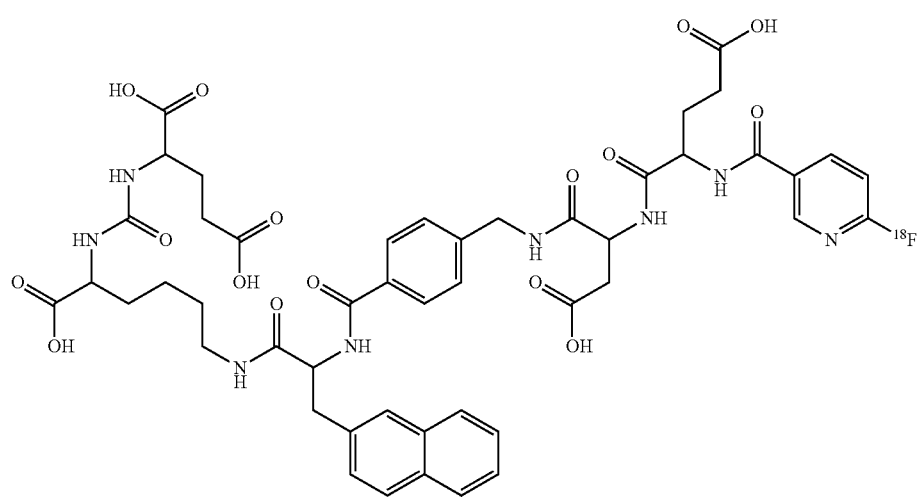
Number: 9
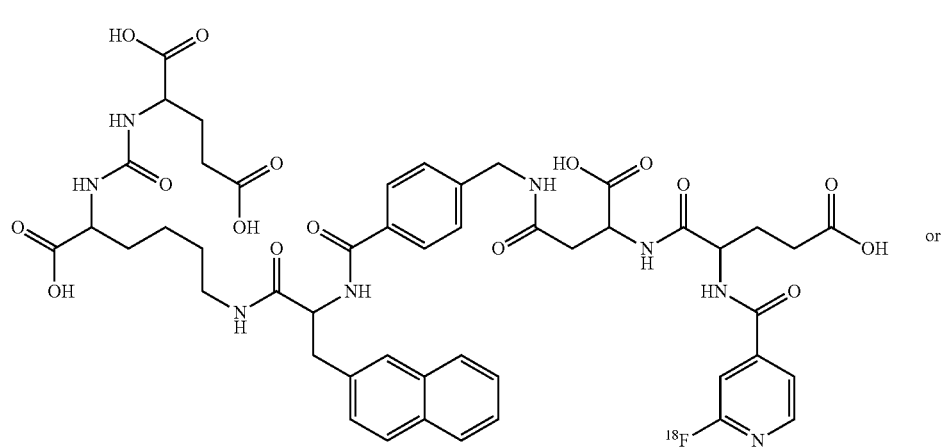
Number: 10a
or
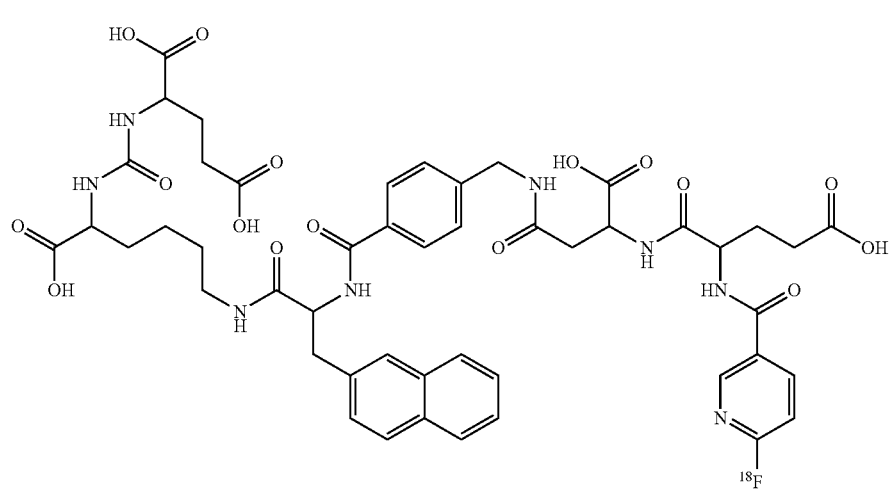
Number: 10

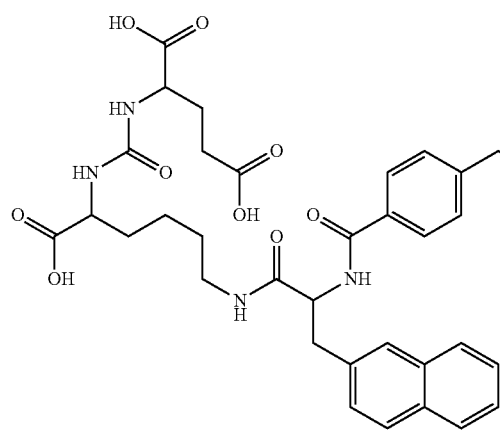 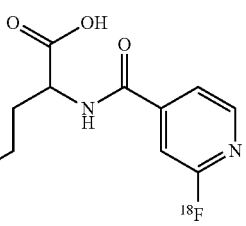
Number: 11a
or
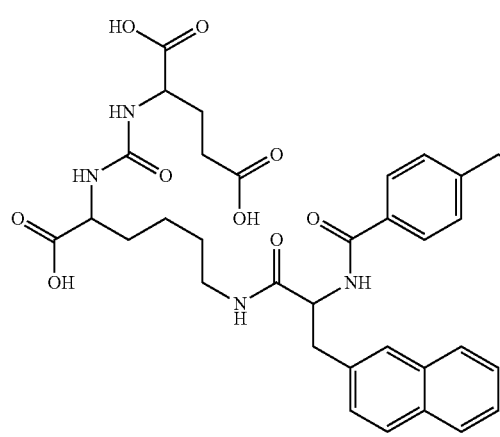 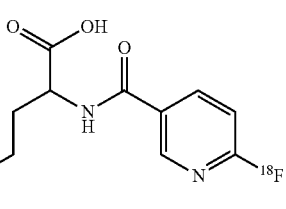
Number: 11
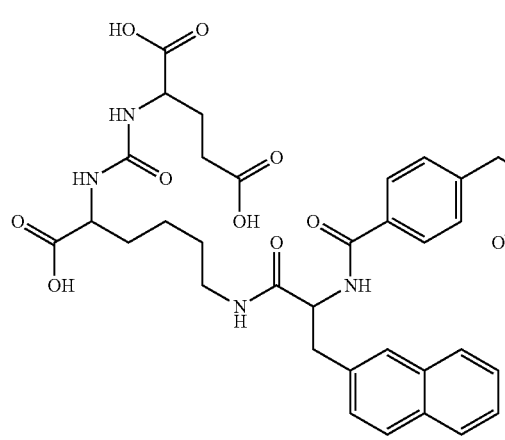 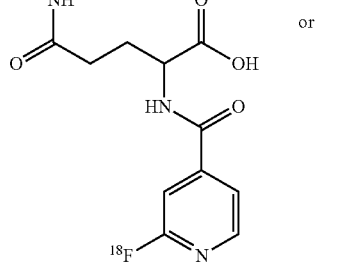
Number: 12a
or -continued
Number: 12
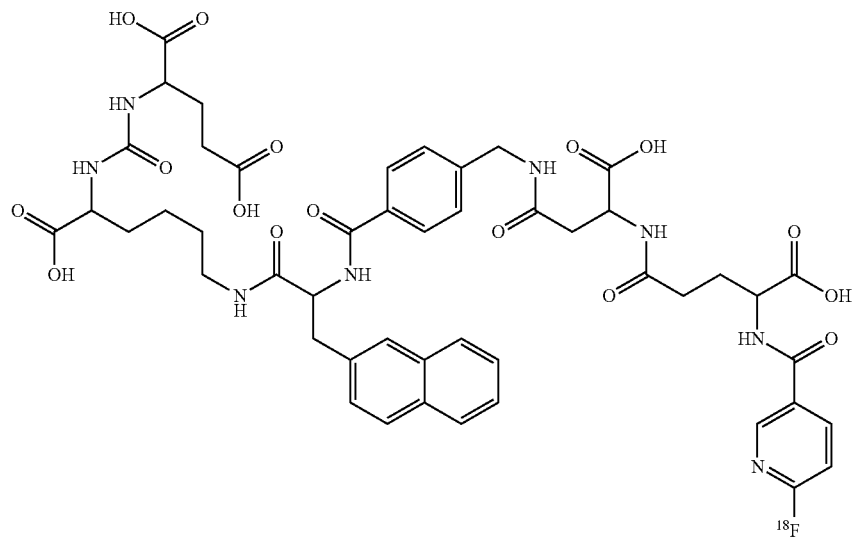
Number: 13a
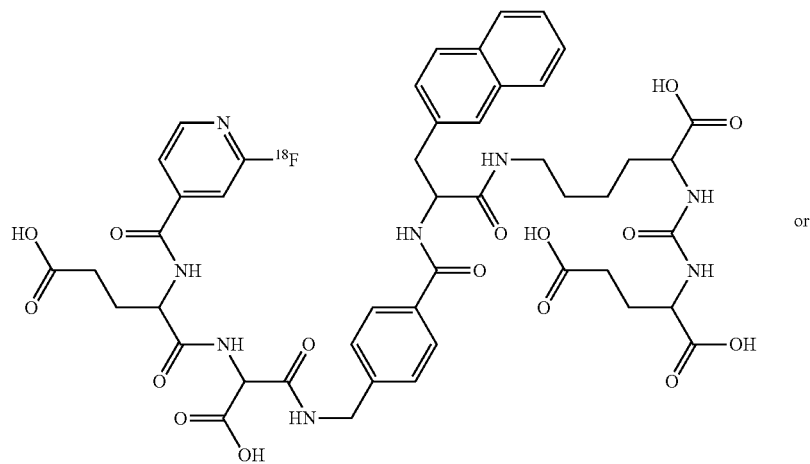
or
Number: 13
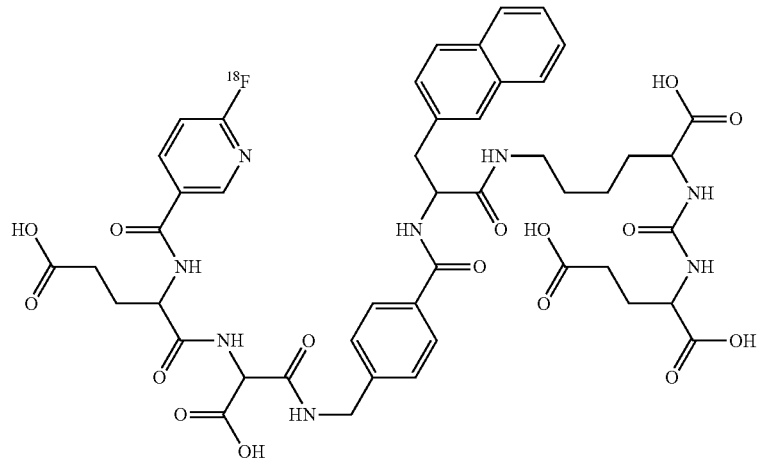

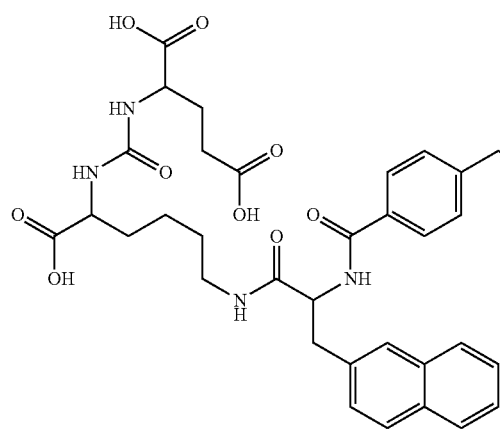
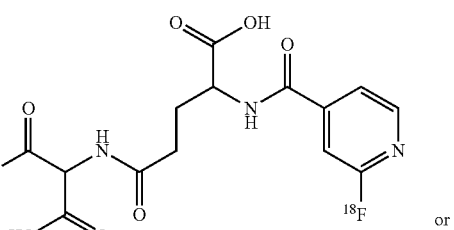
Number: 14a
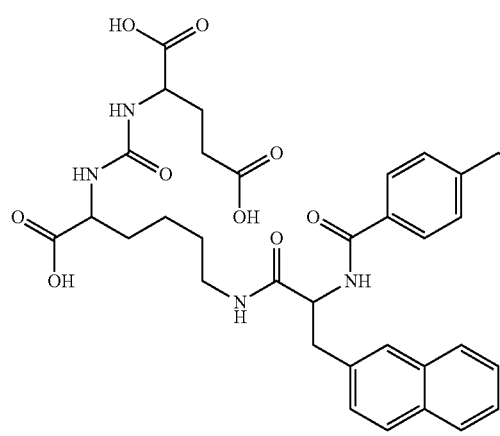
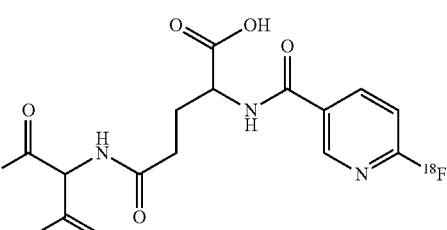
Number: 14
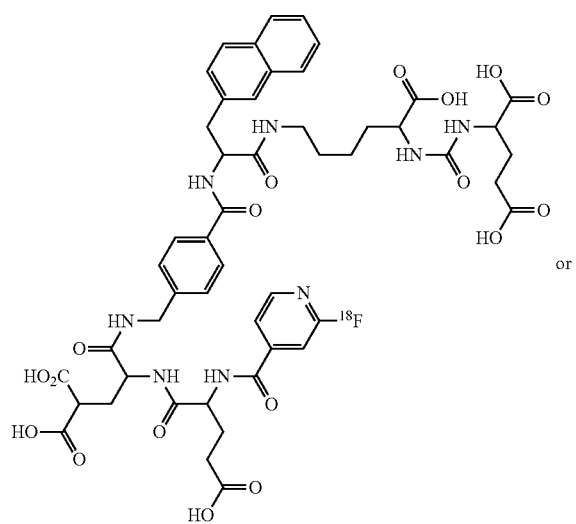
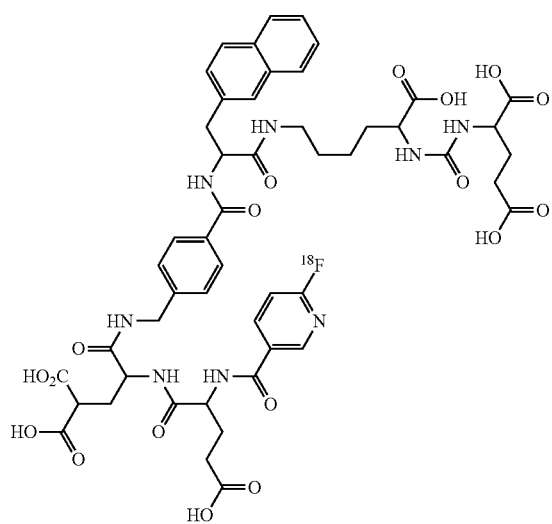
Number: 15a
Number: 15

-continued
Number: 16a
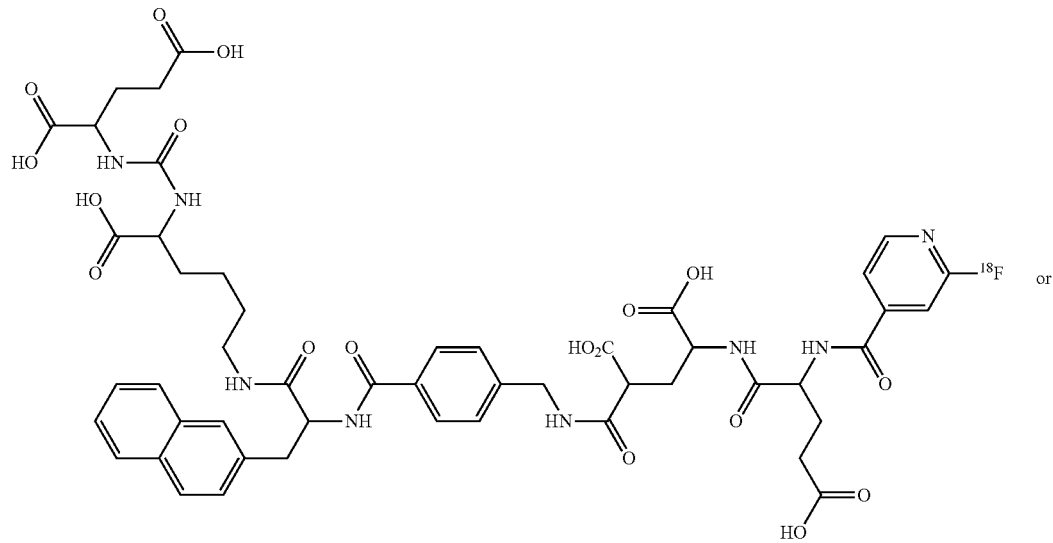
or
Number: 16
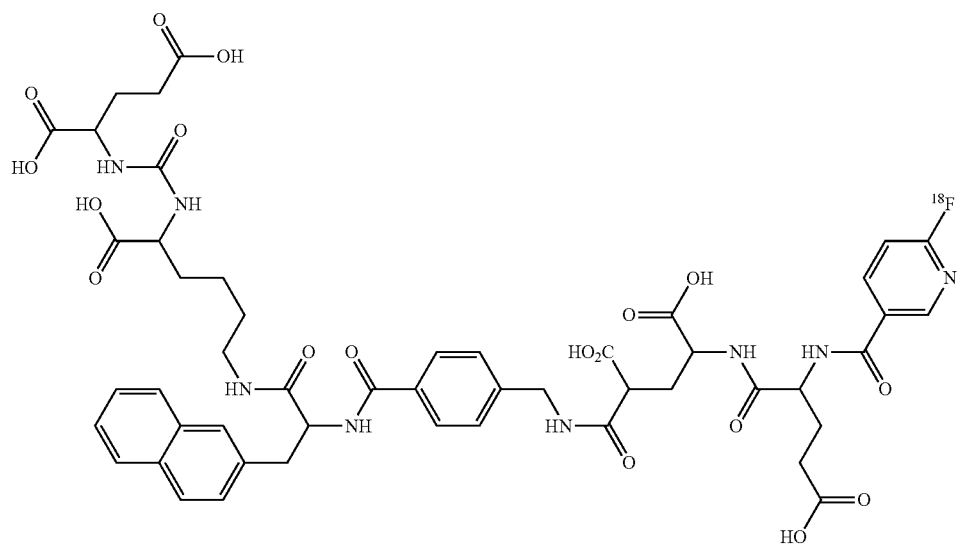

Number: 17a
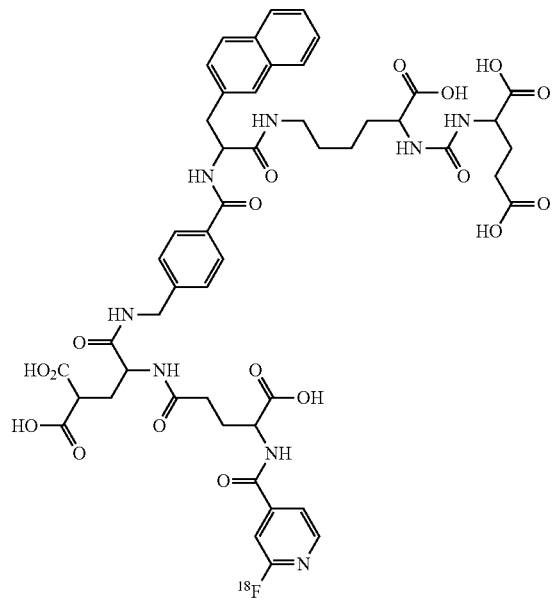
or
Number: 17
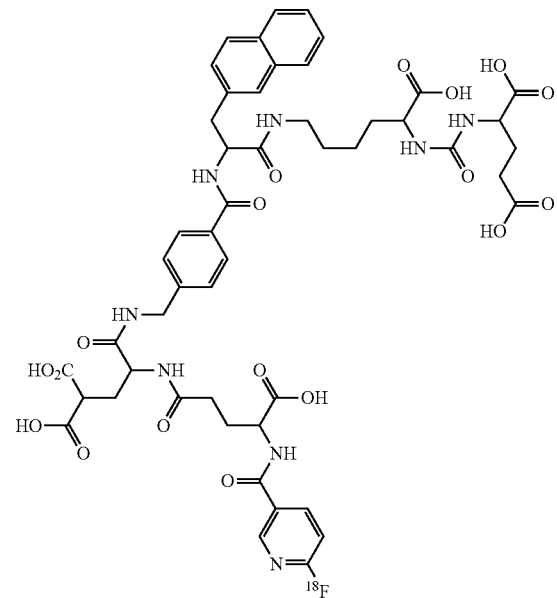
Number: 18a
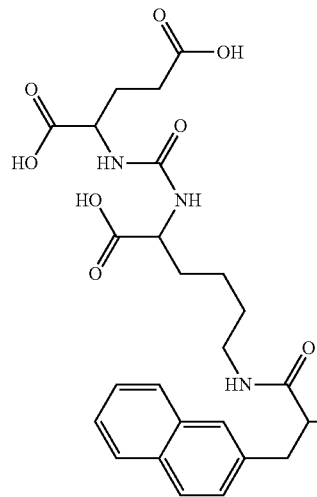
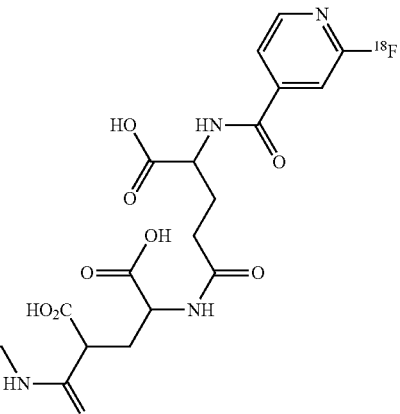
or
Number: 18
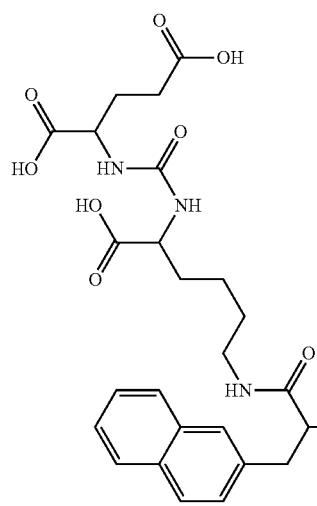
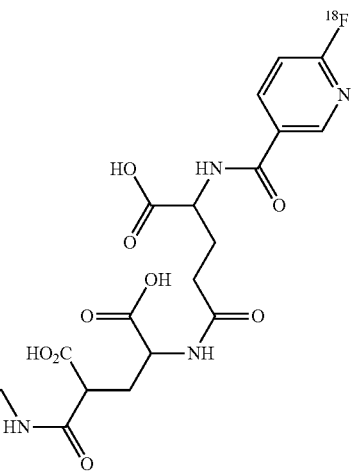

6. The compound of claim 1, wherein $R_1$ is selected from the group consisting of: methyl, 2-ethyl, 3-propyl, 2-,3-,4-phenyl, 2-,3-,4-phenylmethyl, and 2,3-,4-phenylpropyl.

7. The compound of claim 1, wherein $R_2$ is selected from the group consisting of methyl, isopropyl, tert-butyl, phenyl, and 1-naphtyl.

8. A method of imaging a prostate region in a patient comprising the steps of:
   (i) administering to a patient a diagnostically effective amount of the compound of claim 1;
   (ii) exposing the prostate region of the patient to a scanning device to detect the 18F-tag; and
   (iii) obtaining an image of the prostate region of the patient by the scanning device.

* * * * *

UNITED STATES PATENT AND TRADEMARK OFFICE
CERTIFICATE OF CORRECTION

PATENT NO. : 10,815,200 B2
APPLICATION NO. : 15/915978
DATED : October 27, 2020
INVENTOR(S) : Jens Cardinale et al.

It is certified that error appears in the above-identified patent and that said Letters Patent is hereby corrected as shown below:

In the Claims

In Claim 1,
Column 60, Lines 38-39, Lines 50-51, and Lines 61-62; Column 61, Lines 11-12, Lines 26-27, Lines 42-43, and Lines 59-60:
 "especially methyl, 2-ethyl, 3-propyl,
2-, 3-,4-phenyl, 2-, 3-,4-phenylmethyl, 2-, 3-,4-phenylpropyl" should be deleted in each instance.

In Claim 1,
Column 60, Lines 41-42, Lines 53-54, and Lines 64-65; Column 61, Lines 14-15, Lines 29-30, Lines 45-46, and Lines 62-63:
"especially methyl,isopropyl, tert-butyl,
 phenyl or 1-naphtyl" should be deleted in each instance.

Signed and Sealed this
Fifteenth Day of November, 2022

Katherine Kelly Vidal
*Director of the United States Patent and Trademark Office*